United States Patent [19]

Dunlap et al.

[11] Patent Number: 5,250,696
[45] Date of Patent: Oct. 5, 1993

[54] 2-SACCHARINYLMETHYL ARYL CARBOXYLATE

[75] Inventors: Richard P. Dunlap, Penfield; Neil W. Boaz, Waterloo; Albert J. Mura, Rochester; Virendra Kumar, Colonie; Chakrapani Subramanyam, East Greenbush; Ranjit C. Desai, Colonie; Dennis J. Hlasta, Clifton Park; Manohar T. Saindane; Malcolm R. Bell, both of East Greenbush; John J. Court, Colonie, all of N.Y.

[73] Assignee: Sterling Winthrop Inc., New York, N.Y.

[21] Appl. No.: 860,340

[22] Filed: Mar. 30, 1992

Related U.S. Application Data

[60] Division of Ser. No. 782,016, Oct. 24, 1991, Pat. No. 5,128,339, which is a continuation-in-part of Ser. No. 608,068, Nov. 1, 1990, abandoned.

[51] Int. Cl.$^5$ .......................................... C07D 275/06
[52] U.S. Cl. ................................... 548/210; 544/133; 544/368; 546/198
[58] Field of Search ................ 544/133, 368; 546/198; 548/210, 211

[56] References Cited

FOREIGN PATENT DOCUMENTS

| | | |
|---|---|---|
| 253029 | 1/1988 | European Pat. Off. . |
| 446047 | 9/1991 | European Pat. Off. . |
| 48-35457 | 10/1973 | Japan . |
| WO9013549 | 11/1990 | PCT Int'l Appl. . |

OTHER PUBLICATIONS

Yoon et al., J. Korean Agricultural Chemical Society (1986), 29(2), 164–174.

Primary Examiner—Robert W. Ramsuer
Attorney, Agent, or Firm—Michael D. Alexander; Paul E. Dupont

[57] ABSTRACT

4-$R^4$-$R^5$-2-Saccharinylmethyl aryl carboxylates, useful in the treatment of degenerative diseases, are prepared by reacting a 4-$R^4$-$R^5$-2-halomethylsaccharin with an arylcarboxylic acid in the presence of an acid-acceptor.

1 Claim, No Drawings

2-SACCHARINYLMETHYL ARYL CARBOXYLATE

CROSS REFERENCE TO RELATED APPLICATIONS

This application is a division of our prior copending application Ser. No. 07/782,016, filed Oct. 24, 1991 now U.S. Pat. No. 5,128,339 which in turn is a continuation-in-part of our prior copending application Ser. No. 07/608068, filed Nov. 1, 1990 now abandoned.

BACKGROUND OF THE INVENTION (a) Field of the Invention

This invention relates to novel 2-saccharinylmethylaryl carboxylates, which inhibit the enzymatic activity of proteolytic enzymes, to compositions containing the same, to the method of use thereof in the treatment of degenerative diseases and to processes for their preparation.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Japanese Patent Publication 7200419, published Jan. 7, 1972, discloses a number of 2-saccharinylmethylbenzoates, including 2-saccharinylmethyl benzoate per se and 2-saccharinylmethyl 2,4-dichlorobenzoate and 4-nitrobenzoate. The compounds are said to "have strong activity against rice blast, rice sheath blight, rice helminthosporium leaf spot and rice bacterial leaf blight disease".

Sunkel et al., J. Med. Chem., U, 31, 1886-1890 (1988) disclose a series of 2-saccharinyl-lower-alkyl-1,4-dihydropyridine-3-carboxylates having platelet aggregation inhibitory and anti-thrombotic activities.

Chen U.S. Pat. No. 4,263,393, patented Apr. 21, 1981, discloses various 2-aroylmethylsaccharins useful as "photographic elements and film units".

Mulvey et al. U.S. Pat. No. 4,195,023, patented Mar. 25, 1980, discloses $R_1$-2-$R_2$CO-1,2-benzisothiazol-3-ones, where $R_1$ is halogen, alkoxy, alkylamino, dialkylamino, alkoxycarbonyl, amino, nitro or hydrogen in the benzenoid ring and $R_2$ is hydrogen, alkyl, alkenyl, alkynyl, cycloalkyl, halophenyl, heteroaryl or substituted heteroaryl, and $R_1$-2-A-CO saccharins, where $R_1$ has the same meanings as the benzenoid ring substituents in the 1,2-benzisothiazol-3-ones and A is alkyl, alkenyl, alkynyl, cycloalkyl, fluorophenyl, heteroaryl or substitutedheteroaryl. The compounds are said to have elastase inhibitory activity and to be useful in the treatment of emphysema.

Zimmerman et al., J. Biol. Chem., 225(20), 9848-9851 (1980) disclose N-acylsaccharins, where the acyl group is furoyl, thenoyl, benzoyl, cyclopropanoyl, ethylbutyryl and acryloyl, having serine protease inhibitory activity.

Japanese Patent Publication 73/35457, published Oct. 27, 1973, discloses 4-methylphenyl 2-saccharinylcarboxylate which is said to have bactericidal and fungicidal activities.

Several classes of compounds are known to be serine protease inhibitors. For example Powers U.S. Pat. No. 4,659,855 discloses arylsulfonyl fluoride derivatives useful as elastase inhibitors. Doherty et al. U.S. Pat. Nos. 4,547,371 and 4,623,645 disclose cephalosporin sulfones and sulfoxides, respectively, which are stated to be potent elastase inhibitors useful in the treatment of inflammatory conditions, especially arthritis and emphysema.

Teshima et al., J. Biol. Chem., ZU(9), 5085-5091 (1982) report the results of studies on serine proteases (human leukocyte elastase, porcine pancreatic elastase, cathepsin G and bovine chymotrypsin $A_\alpha$) with 4-nitrophenylesters and thioesters of N-trifluoroacetylanthranilates, 2-substituted-4H-3,1-benzoxazin-4-ones, 2-substituted-4-quinazolinones and 2-substituted-4-chloroquinazolines.

Cha, Biochem. Pharmacol., 24, 2177-2185 (1975) discusses kinetic approaches to the study of the binding of inhibitors to macromolecules, such as enzymes, and methods for determination of such parameters as the inhibition constants, reaction rates and bound and unbound enzyme concentrations.

Jones et al., U.S. Pat. No. 4,276,298 discloses 2-R-1,2-benzisothiazolinone-1,1-dioxides, where R is phenyl substituted by fluoro, dinitro, trifluoromethyl, cyano, alkoxycarbonyl, alkylcarbonyl, carboxyl, carbamoyl, alkylacylamino, alkylsulfonyl, N,N-dialkylsulfamoyl, trifluoromethoxy, trifluoromethylthio, trifluoromethylsulfonyl and trifluoromethylsulfinyl, or pyridyl substituted the same as R when R is phenyl except that pyridyl may also be mononitro substituted. The compounds are said to have protease enzyme inhibitory activity, especially elastase inhibitory activity, and to be useful in the treatment of emphysema, rheumatoid arthritis "and other inflammatory diseases".

Powers, Biochem., 2A, 2048-2058 (1985) discloses studies of the inhibitions of four chymotrypsin-like enzymes, cathepsin G, rat mast cell proteases I and II, human skin chymase and chymotrypsin $A_\alpha$, by N-furoylsaccharin and N-(2,4-dicyanophenyl)saccharin.

Svoboda et al., Coll. Czech. Chem. Commun., 51, 1133-1139 (1986) disclose the preparation of 4-hydroxy-2H-1,2-benzothiazine-3-carboxylates by intramolecular Dieckmann condensation of 2H-1,2-benzisothiazol-3-one-2-acetate-1,1-dioxide esters.

Reczek et al. U.S. Pat. Nos. 4,350,752 and 4,363,865 and Vanmeter et al. U.S. Pat. No. 4,410,618 relate to photographic reagents (Reczek U.S. Pat. No. 4,350,752 and Vanmeter et al.) and photographic dyes (Reczek U.S. Pat. No. 4,363,865) and disclose various 2-substituted-saccharins useful for such applications, for example "photographic reagents" bound through a heteroatom to an "imidomethyl blocking" group (Reczek U.S. Pat. No. 4,350,752), "carrier-diffusible photographic dyes" bound to the nitrogen atom of an imide through a 1,1-alkylene group (Reczek U.S. Pat. No. 4,363,865) and N-acylmethylimides which are described as "blocked photographic reagents" and which have a "residue of an organic photographic reagent containing a hetero atom through which it is bound to the blocking group" (Vanmeter).

Freed U.S. Patent 3,314,960 discloses 2-(1,1,3-trioxo-1,2-benzisothiazol-2-yl)glutarimides which are stated to be useful as sedatives.

2-Chloromethylsaccharin is disclosed in French Patent 1,451,417 as an intermediate for the preparation of N-methylsaccharin d,1-trans-chrysanthemate, useful as an insecticide, and Lo U.S. Pat. No. 3,002,884 discloses 2-chloro, 2-bromo and 2-iodomethylsaccharins, useful as fungicidal agents.

SUMMARY OF THE INVENTION

In a composition of matter aspect, this invention relates to 4-$R^4$-$R^5$-2-saccharinylmethyl aryl carboxylates and 4,5,6,7-tetrahydro-2-saccharinylmethyl aryl carboxylates which have protease enzyme inhibitory activity and which are useful in the treatment of degenerative diseases.

In a composition aspect, the invention relates to compositions for the treatment of degenerative diseases which comprise a pharmaceutical carrier and an effective proteolytic enzyme inhibiting amount of a 4-$R^4$-$R^5$-2-saccharinylmethyl aryl carboxylate or a 4,5,6,7-tetrahydro-2-saccharinylmethyl aryl carboxylate.

In a method aspect, the invention relates to a method of use of said 2-saccharinylmethyl aryl carboxylates in the treatment of degenerative diseases which comprises administering to a patient in need of such treatment a medicament containing an effective proteolytic enzyme inhibiting amount of a 4-$R^4$-$R^5$-2-saccharinylmethyl aryl carboxylate or 4,5,6,7-tetrahydro-2-saccharinylmethyl aryl carboxylate.

In process aspects, the invention relates to processes for the preparation of said 4-$R^4$-$R^5$-2-saccharinylmethyl aryl carboxylates and 4,5,6,7-tetrahydro-2-saccharinylmethyl aryl carboxylates which comprise reacting (1) a 2-halomethylsaccharin with an aryl carboxylic acid in the presence of an acid-acceptor, or (2) reacting a saccharin with a chloromethyl ester of an aryl carboxylic acid in the presence of an acid acceptor, or (3) reacting an alkali metal or thallium salt of the appropriate acid with the appropriate halomethyl species.

In a further process aspect, the invention relates to a process for the preparation of 4-$R^4$-$R^5$-saccharins, useful as intermediates for the preparation of the corresponding 4-$R^4$-$R^5$-2-saccharinylmethyl aryl carboxylates, which comprises reacting a 2-$R^4$-$R^5$-N,N-di-lower-alkylbenzamide with a lower-alkyl alkali metal such as an inert organic solvent; reacting the resulting alkali metal salt either with sulfur dioxide followed by hydroxylamine-O-sulfonic acid in the presence of base or with a sulfuryl halide followed by ammonia; heating the resulting 2-$R^4$-$R^5$-6-aminosulfonyl-N,N-di-lower-alkylbenzamide in a lower-alkanoic acid; and treating the resulting 4-$R^4$-$R^5$-saccharin di-lower-alkylammonium salt with aqueous acid.

In a further process aspect, the invention relates to a process for the preparation of 2-chloromethyl saccharins useful as intermediates for the preparation of 2-saccharinylmethyl aryl carboxylates, which comprises reacting a saccharin with a chlorosilane and formaldehyde in the presence of a Lewis acid.

In a further process aspect, the invention relates to a process for preparing 4-n-lower-alkylsaccharins, useful as intermediates, which comprises protecting the benzylic position of a 2-n-lower-alkyl-N,N-dialkylbenzamide with an appropriate trialkylsilane, constructing the isothiazole ring as above, and deprotecting using a source of fluoride anion.

DETAILED DESCRIPTION OF THE PREFERRED EMBODIMENTS

More specifically this invention relates to 4-$R^4$-$R^5$-2-saccharinylmethyl aryl carboxylates having the formula:

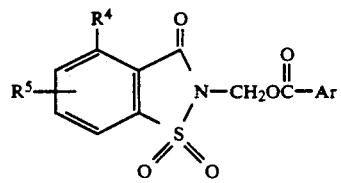

wherein:

Ar is phenyl, naphthyl or anthryl or such groups substituted by from one to three, the same or different, members of the group consisting of lower-alkyl, perfluorolower-alkyl, perchlorolower-alkyl, lower-alkoxy, halogen, nitro, cyano, carboxy, PO(-lower-alkoxy)$_2$, amino, lower-alkylamino, dilower-alkylamino, lower-alkanoylamino, lower-alkoxycarbonyl, hydroxy, benzyloxy, carboxylower-alkoxy, —SO$_2$—N═B, —CO—N═B, —(alkylene)—N═B, —COO(alkylene)—N═B, —NH-(alkylene)—N═B; —N(lower-alkyl)—(alkylene)—N═B, or —O—(alkylene)—N═B, where N═B in each instance is amino, lower-alkylamino, di-lower-alkyl-amino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl, carboxy-lower-alkylamino; or —NR—(alkylene)—N(alkyl)2, where R lower-alkyl $R^4$ is hydrogen, halogen, lower-alkyl, perfluorolower-alkyl, perchlorolower-alkyl, lower-alkenyl, lower-alkynyl, cyano, amino, lower-alkylamino, dilower-alkylamino, lower-alkoxy, benzyloxy, lower-alkoxycarbonyl, phenyl or carboxamido; and $R^5$ is hydrogen or from one to two the same or different substituents in any of the 5-, 6- or 7-positions selected from halogen, cyano, nitro, N═B, 1-lower-alkyl-2-pyrrolyl, lower-alkylsulfonylamino, polyfluoroloweralkylsulfonylamino, polychlorolower-alkylsulfonylamino, aminosulfonyl, lower-alkyl, polyfluorolower-alkyl, polychlorolower-alkyl, cycloalkyl, lower-alkoxy, hydroxy, carboxy, carboxamido, hydroxylower-alkyl, methylenedioxy, cycloalkyloxy, formyl, aminomethyl, lower-alkylsulfonyl, polyfluorolower-alkylsulfonyl, polychlorolower-alkylsulfonyl, lower-alkylsulfonylaminosulfonyl, di(loweralkyl)phosphonoxy, lower-alkoxypoly-loweralkyleneoxy, hydroxylower-alkoxy, polyhydroxylower-alkoxy, or acetal or ketal thereof, poly(lower-alkoxy)lower-alkoxy, —O—(alkylene)—COOR, —O—(alkylene)—N═B, —SR, —SOR, —SO$_2$R or —OCOR, where R is lower-alkyl, phenyl, benzyl or naphthyl, or phenyl or naphthyl substituted by from one to two substituents selected from lower-alkyl, lower-alkoxy or halogen, and —N=B has the meanings given above, or $R^5$ is a 5- or 6-membered saturated ring fused to the saccharin at the 5,6 or 6,7-positions, said ring containing two heteroatoms chosen from the group consisting of nitrogen, oxygen and sulfur, or a methylated derivative of said ring;

or acid-addition salts of basic saccharinylmethyl carboxylates or base-addition salts of acidic saccharinylmethylcarboxylates, with the proviso that, when $R^4$ and $R^5$ are both hydrogen, Ar cannot be either phenyl, 2,4-dichlorophenyl or 4-nitrophenyl.

Preferred compounds of formula I above are those wherein:

Ar is phenyl, naphthyl or anthryl or such groups substituted by from one to three, the same or different, members of the group consisting of lower-alkyl, perfluorolower-alkyl, lower-alkoxy, halogen, nitro, PO(lower-alkoxy)2, lower-alkanoylamino, hydroxy, carboxylower-alkoxy, benzyloxy, —SO₂—N=B or —O—(alkylene)-N=B, where N=B is di-lower-alkylamino, 1-pyrrolidinyl, 1-piperidinyl, 4-morpholinyl, 1-piperazinyl, 4-lower-alkyl-1-piperazinyl, 4-benzyl-1-piperazinyl, carboxylower-alkylamino or —NR—(alkylene)-N(alkyl)₂, where R is lower-alkyl;

$R^4$ is hydrogen, primary or secondary-lower-alkyl, lower-alkoxy or phenyl; and $R^5$ is hydrogen, hydroxy, lower-alkoxy, methylenedioxy, cycloalkyloxy, hydroxylower-alkoxy, polyhydroxylower-alkoxy, or acetal or ketal thereof, poly(-lower-alkoxy)lower-alkoxy, —O—(alkylene)—COOR, or O—(alkylene)-N=B or $R^5$ is a [6,5-fused 1,3-oxazine.

Particularly preferred compounds of formula I are those wherein:

Ar is phenyl or phenyl substituted by from one to three, the same or different, members selected from the group consisting of lower-alkyl, lower-alkoxy, halogen, hydroxy, carboxylower-alkoxy, benzyloxy, —SO₂—N=B or —O— (alkylene)—N=B, where N=B is dilower-alkylamino, 1-pyrrolidinyl, 1-piperidinyl, 4-morpholinyl, 1-piperazinyl, 4-lower-alkyl-1-piperazinyl, 4-benzyl-1-piperazinyl, carboxylower-alkylamino or —NR—(alkylene)-N(alkyl)₂, where R is lower-alkyl;

$R^4$ is primary or secondary lower-alkyl or lower-alkoxy; and $R^5$ is hydrogen, lower-alkoxy, methylenedioxy, cycloalkyloxy, hydroxylower-alkoxy, polyhydroxylower-alkoxy, or acetal or ketal thereof, poly(lower-alkoxy)lower-alkoxy, —O—(alkylene)—COOR, or O—(alkylene)—N=B.

Other preferred compounds of formula I are those wherein:

Ar is phenyl, naphthyl or anthryl, or phenyl substituted by from one to three, the same or different, members selected from the group consisting of lower-alkyl, perfluoro-lower-alkyl, lower-alkoxy, halogen or lower-alkanoylamino;

$R^4$ is hydrogen, primary or secondary lower-alkyl, lower-alkoxy or phenyl; and $R^5$ is hydrogen or lower-alkyl.

Still other preferred compounds of formula I are these wherein:

Ar is phenyl or phenyl substituted by from one to three, the same or different, members selected from the group consisting of lower-alkoxy, halogen or lower-alkyl;

$R^4$ is hydrogen, primary or secondary-lower-alkyl or lower-alkoxy; and $R^5$ is hydroxy in any of the 5-, 6- or 7-positions.

It should be understood that the compounds having the general structural formula I are usually named in the chemical literature as 1,2-benzisothiazol-3(2H)-one 1,1-dioxides. However for the sake of brevity, such compounds are frequently named as saccharin derivatives, and that nomenclature will be used hereinafter in describing the compounds of the invention and their biological properties.

The invention also relates to 4,5,6,7-tetrahydro2-saccharinylmethyl aryl carboxylates of formula VI

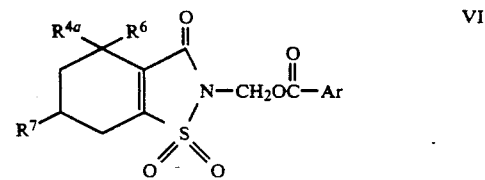

wherein $R^{4a}$ is hydrogen, lower-alkyl or phenyl, $R^6$ is hydrogen or primary lower-alkyl or $R^{4a}$ and $R^6$ together form a spirocyclopropyl ring, $R^7$ is hydrogen or lower-alkoxy, and Ar is as defined for formula I.

Preferred tetrahydrosaccharins of formula VI are those wherein $R^{4a}$ is hydrogen, methyl, ethyl or isopropyl, $R^6$ is hydrogen or methyl, R7 is hydrogen or methoxy and Ar is phenyl substituted by from one to three, the same or different, members of the group consisting of lower-alkyl, lower-alkoxy, halogen, hydroxy and —O—(alkylene)—N=B.

The invention also relates to compounds of the formula

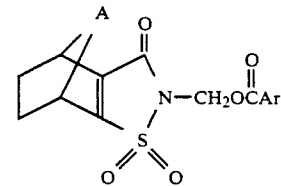

wherein A is methylene, ethylene or dimethylmethylene and Ar is phenyl, naphthyl or anthryl or such groups substituted by from one to three, the same or different, members of the group consisting of lower-alkyl, perfluorolower-alkyl, perchlorolower-alkyl, lower-alkoxy, halogen, nitro, cyan, carboxy, OPO(lower-alkoxy)₂, amino, lower-alkylamino, dilower-alkylamino, lower-alkanoylamino, lower-alkoxycarbonyl, hydroxy, benzyloxy, carboxylower-alkoxy, —SO₂—N=B, —CO—N=B; —(alkylene)—N=B, —COO-(alkylene)—N=B, —NH(alkylene)N=B; —N(lower-alkyl)—(alkylene)—N=B; or —O—(alkylene)—N=B, where N=B in each instance is amino, lower-alkylamino, dilower-alkyl-amino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl or carboxy-lower-alkylamino.

As used herein the terms lower-alkyl, lower-alkoxy and lower-alkane mean monovalent aliphatic radicals, including branched chain radicals, of from one to ten carbon atoms. Thus the lower-alkyl (or lower-alkane)

moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein the term halogen (or halo) means fluorine, chlorine, bromine or iodine.

As used herein the terms lower-alkenyl and lower-alkynyl mean monovalent, unsaturated radicals, including branched chain radicals, of from two to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl), and the like.

As used herein, the term alkylene means divalent, saturated radicals, including branched chain radicals, of from two to ten carbon atoms and having their free valences on different carbon atoms and thus includes 1,2-ethylene, 1,3-propylene, 1,4-butylene, 1-methyl-1,2-ethylene, 1,8-octylene and the like.

As used herein cycloalkyl means $C_3$ through $C_7$ saturated monocyclic hydrocarbon residues and thus includes cyclopropyl, cyclobutyl, cyclopentyl, cyclohexyl and cycloheptyl.

The compounds of the present invention inhibit the activity of serine proteases, specifically human leukocyte elastase and the chymotrypsin-like enzymes, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid and alpha-1-antitrypsin deficiency.

The compounds of formula I and formula VI are prepared by reaction of a 2-halomethylsaccharin or 2-halomethyl-4,5,6,7-tetrahydrosaccharin with an appropriate aryl carboxylic acid, Ar—COOH or by reaction of a saccharin or tetrahydrosaccharin with a chloromethyl ester of an aryl carboxylic acid.

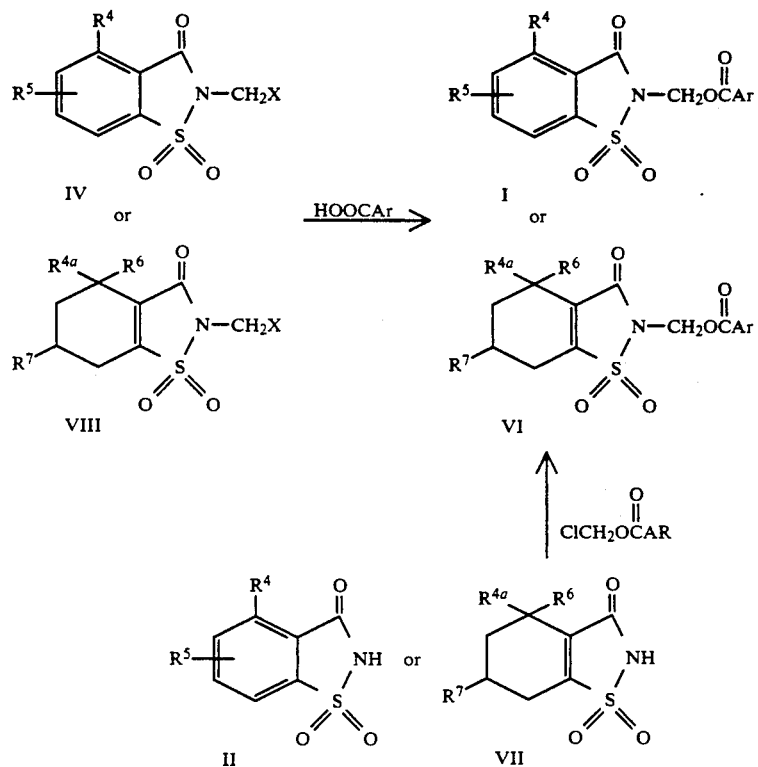

The reaction can either be carried out in the presence of an acid-acceptor, such as an alkali metal carbonate, a trilower-alkylamine or 1,8-diazabicyclo-[5.4.0.]undec-7-ene, hereinafter DBU. Alternatively the salt of an alkali metal or thallous salt of the aryl carboxylic acid can be used (prepared by reaction of the acid with an alkali metal carbonate or thallous lower-alkoxide). The reaction is carried out in an organic solvent inert under the conditions of the reaction, for example acetone, methyl ethyl ketone (MEK), acetonitrile, tetrahydrofuran (THF), diethyl ether, dimethylformamide (DMF), N-methylpyrrolidinone, methylene dichloride (MDC), xylene, toluene or lower-alkanols, at a temperature in the range from ambient up to the boiling point of the solvent used.

The 4-$R^4$-$R^5$-2-halomethylsaccharins required for the preparation of the compounds of formula I are prepared by the methods described by D'Alelio et al., J. Macromol. Sci-Chem., A3(5), 941 (1969) and Saari et al., J. Het. Chem., 23, 1253 (1986)

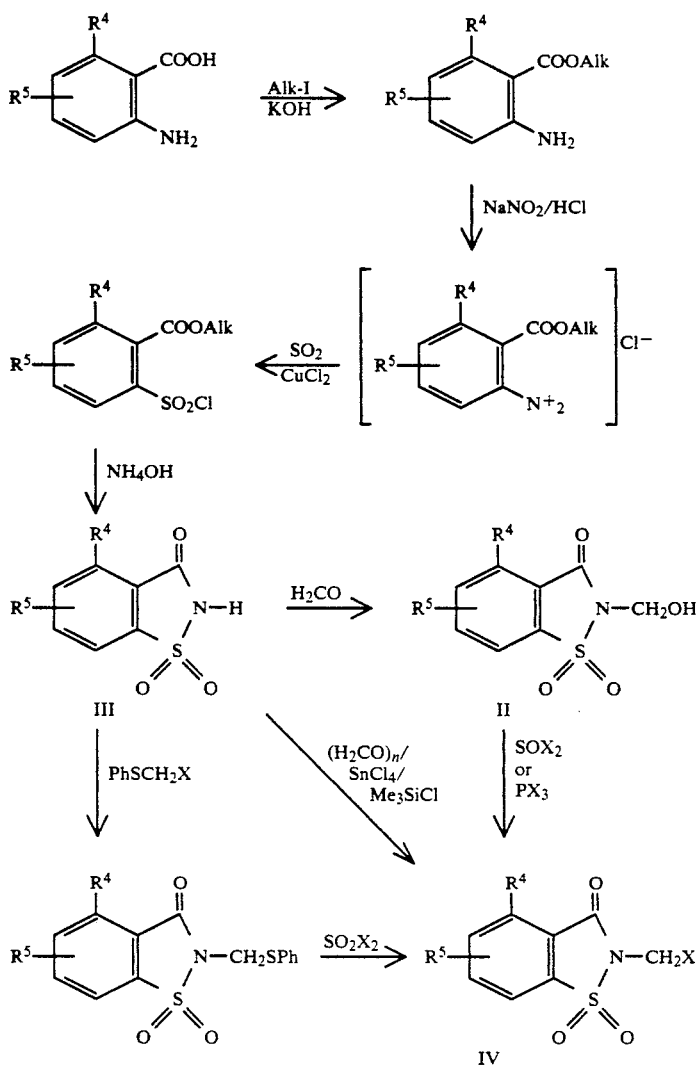

In the method described by Saari, a methyl ester of an appropriate anthranilic acid is prepared by conventional means from the substituted anthranilic acid and the ester diazotized. The diazonium salt is then reacted with sulfur dioxide and cupric chloride to produce a sulfonyl chloride which is then reacted with concentrated ammonium hydroxide to produce the substituted saccharin derivatives of formula II. The latter, on reaction with formaldehyde in a lower-alkanol solvent, affords the 4-$R^4$-$R^5$-2-hydroxymethylsaccharins of formula III, which, on reaction with a thionyl halide or a phosphorus trihalide, afford the corresponding 4-$R^4$-$R^5$-2-halomethylsaccharin derivatives of formula IV.

The 4-$R^4$-$R^5$-2-halomethylsaccharins of formula IV, where X is chlorine or bromine, can also be prepared by reaction of a corresponding 4-$R^4$-$R^5$-2-phenylthiomethylsaccharin with a sulfuryl halide in an inert organic solvent, for example MDC, ethylene dichloride (EDC) or carbon tetrachloride, at a temperature from around 0° C. to around 30° C. The 4-$R^4$-$R^5$-2-phenylthiomethylsaccharins are in turn prepared by reaction of a 4-$R^4$-$R^5$-saccharin of formula II with a halomethylphenyl sulfide in an inert organic solvent, such as toluene, xylene, DMF or MDC at a temperature in the range from ambient up to the boiling point of the solvent used. The reaction can be carried out by reaction of the halomethyl phenyl sulfide with either the thallium salt of the saccharin derivative of formula II (prepared by reaction of the saccharin derivative with a thallium lower-alkoxide in a lower-alkanol); or with a dilower-alkyl ammonium salt of the saccharin derivatives (prepared as described below) in the presence of a tetralower-alkyl ammonium halide, such as tetrabutyl ammonium bromide (hereinafter TBAB); or with the saccharin derivative of formula II per se in the presence of a tetraloweralkyl ammonium halide; or with the saccharin derivative of formula II per se in the presence of a tetraloweralkyl ammonium halide and an alkali metal lower-alkoxide, such as potassium t-butoxide.

The saccharins of formula II may also be converted to the chloromethyl saccharins of formula IV, wherein X is Cl, in one step by reaction with an excess of formaldehyde or a formaldehyde equivalent, such as paraformaldehyde or 1,3,5-trioxane, and a chlorosilane, preferably chlorotrimethylsilane in the presence of a Lewis acid, preferably a catalytic amount of stannic chloride in an inert solvent, preferably 1,2-dichloroethane (ethylene dichloride, EDC).

It will be appreciated that all of the conversions of the saccharins II to the 2-chloromethyl saccharins IV are equally applicable to the conversion of tetrahydrosaccharins VII to 2-chloromethyl tetrahydrosaccharins VIII.

The compounds of formula II can also be prepared by reaction of a 2-R$^4$-R$^5$-N,N-di-lower-alkylbenzamide of formula V with one molar equivalent of a lower-alkylalkalimetal, such as lithium, optionally in the presence of a tetraloweralkylethylenediamine, in an inert organic solvent, for example THF, and reaction of the resulting alkali metal salt either with sulfur dioxide at a temperature in the range from −50° C. to −80° C. followed by reaction of the resulting alkali metal sulfinate with hydroxylamine-O-sulfonic acid in the presence of base, or with a sulfuryl halide followed by ammonia. When the sulfur dioxide-hydroxylamine-O-sulfonic acid route is used, it is particularly advantageous to neutralize the hydroxylamine-O-sulfonic acid with one equivalent of sodium hydroxide prior to addition of the alkali metal sulfinate. The resulting 2-R$^4$-R$^5$-6-aminosulfonylN,N-dilower-alkylbenzamide is thereafter heated in an acid medium to effect cyclization of the latter to produce the dilower-alkyl ammonium salt of the desired 4-R$^4$-R$^5$-saccharin of formula II, which can be used as such in the subsequent reaction or, if desired, can be hydrolyzed in dilute acid and the free saccharin isolated. It is preferred to carry out the cyclization in refluxing glacial acetic acid. The method is illustrated as follows where R$^4$, R$^5$ and Alk have the meanings given above and the alkali metal is lithium.

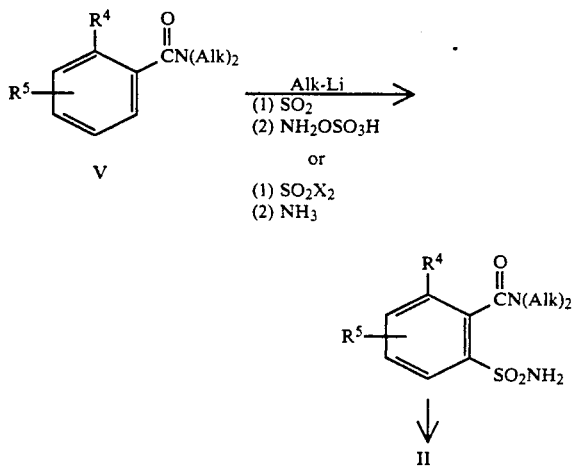

The compounds of formula II where R$^4$ is either primary or secondary lower-alkyl, and which are useful as intermediates for the preparation of the compounds of formula I as described above, are prepared by one of two methods. The compounds of formula II where R$^4$ is primary lower-alkyl are prepared by reacting a 4-methyl-R$^5$-saccharin (formula II, R$^4$ is CH$_3$) with two molar equivalents of a lower-alkyl lithium in an inert organic solvent, for example THF, and reacting the resulting lithium salt with one molar equivalent of a lower-alkyl halide, both reactions being carried out at a temperature in the range from about −50° C. to −80° C.

Another method for preparing the compounds of formula II where R$^4$ is either primary or secondary lower-alkyl comprises reaction of a 2-primary-lower-alkyl-R$^5$-N,N-di-lower-alkylbenzamide (formula V, R$^4$ is primary-lower-alkyl) with one molar equivalent of a lower-alkyl lithium or a lithium dilower-alkylamide, optionally in the presence of a tetralower-alkylethylenediamine, in an inert organic solvent, for example THF, and reaction of the resulting lithium salt with one molar equivalent of a lower-alkyl halide at a temperature in the range from about −50° C. to −80° C. The resulting 2-primary or secondary-lower-alkyl-R$^5$-N,N-di-lower-alkyl-benzamide is thereafter converted to the compounds of formula 11, where R$^4$ is primary or secondary lower-alkyl, by the same sequence of reactions described above, i.e. by reaction of the 2-primary or secondary-lower-alkyl-R$^5$-N,N-di-lower-alkylbenzamide with one molar equivalent of a lower-alkyl alkali metal, such as lithium; reaction of the resulting alkali metal salt either with sulfur dioxide followed by hydroxylamine-O-sulfonic acid in the presence of base or with a sulfuryl halide followed by ammonia; and cyclization of the product to the desired 4-primary or secondary-lower-alkyl-R$^5$-saccharin of formula II. When the 2-lower-alkyl group in the 2-lower-alkyl-R$^5$-N,N-di-lower-alkyl-benzamide starting material is methyl, alkylation affords species where the 2-lower-alkyl group is either straight or branched depending upon whether a straight or branched chain loweralkylhalide is used for the alkylation. On the other hand, when the 2-lower-alkyl group in the starting material contains more than one carbon atom, alkylation takes place on the carbon atom adjacent the benzene ring and affords products having a sec.-lower-alkyl group at the 2-position.

A particularly useful method for the preparation of compounds II where R$^4$ is n-lower-alkyl and R$^5$ is hydrogen involves the protection of the benzylic protons of the starting material V with a trialkylsilyl group, thereby permitting lithiation at the 6-position and formation of the sulfonamide as described above.

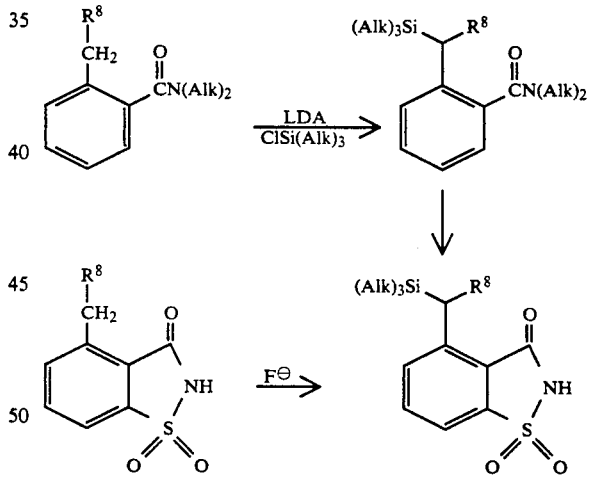

A 2-n-lower-alkylbenzamide wherein R$^8$ is lower-alkyl is silylated by forming the benzylic anion using an alkyllithium or, preferably, a lithium dialkylamide in an inert solvent, preferably THF, and treating with a suitable chlorotrialkylsilane, preferably chlorotrimethylsilane. The saccharin is synthesized as before, and the silyl group is removed by treatment with a source of fluoride anion, preferably cesium fluoride in DMF or tetra-n-butylammonium fluoride in an inert solvent.

Access to certain of the required intermediates in some cases requires building up the two rings making up the saccharin or tetrahydrosaccharin nucleus. Thus to prepare saccharins where R$^4$ is lower-alkoxy and R$^5$ is 7-hydroxy, or tetrahydrosaccharins where R$^7$ is lower-alkoxy, the following synthesis may be used:

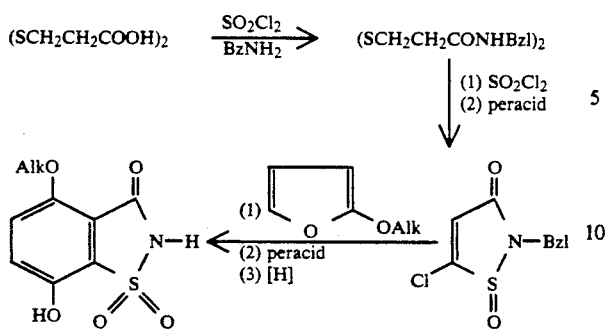

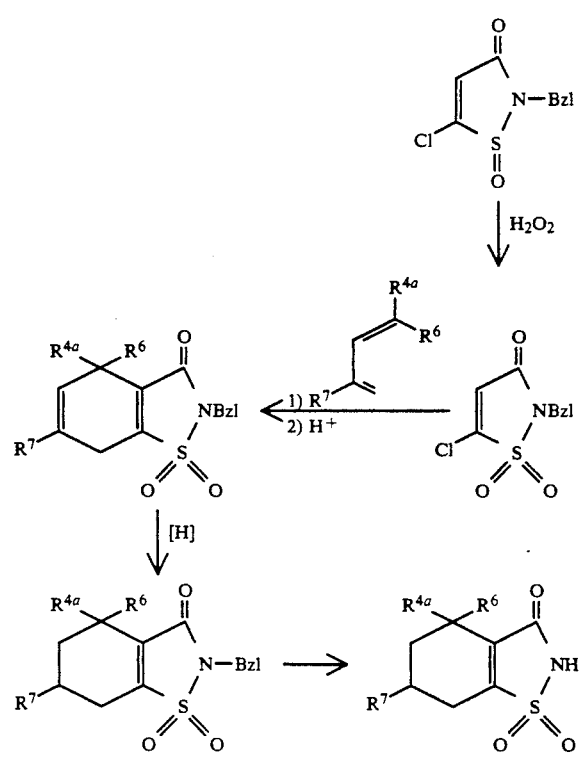

3,3-Dithiobispropionic acid is converted to the bis acid chloride by reaction of the acid with thionyl chloride, and the acid chloride is then reacted with two molar equivalents of benzylamine to produce the bis N-benzylamide. The latter, on reaction with sulfuryl chloride in an organic solvent, such as MDC, EDC or carbon tetrachloride, affords 5-chloro-2-benzyl-2H-isothiazol-3-one, which is oxidized with one molar equivalent of a peracid, such as perbenzoic acid or 3-chloroperbenzoic acid, to 5-chloro-2-benzyl-2H-isothiazol-3-one-1-oxide. The latter, on heating under pressure with a 2-lower-alkoxyfuran in an organic solvent, such as benzene, toluene or xylene, affords a 4-loweralkoxy-7-hydroxy-2-benzyl-1,2-benzisothiazol-2H-3-one-1-oxide. The 7-hydroxy group can, if desired, then be reacted with a lower-alkyl halide or a lower-alkoxypoly-lower-alkoxy-lower-alkyl halide to give the corresponding 4,7-dilower-alkoxy or 4-lower-alkoxy-7-lower-alkoxypoly-lower-alkoxy-2-benzyl-1,2-benzisothiazol-2H-3-one-1-oxide. Further oxidation of the product with one molar equivalent of a peracid as described above followed by catalytic debenzylation by transfer hydrogenation affords the corresponding 4-lower-alkoxy-7-hydroxysaccharins.

When a tetrahydrosaccharin is desired, the following modification is used:

The 5-chloro-2-benzyl-2H-isothiazole-3-one-1-oxide may be oxidized with a suitable oxidizing agent, preferably hydrogen peroxide in acetic acid, to the 1,1-dioxide which is then reacted under typical Diels Alder conditions with the appropriate diene and reduced to provide the 2-benzyl tetrahydrosaccharin which is hydrogenolyzed as before to the tetrahydrosaccharin.

Compounds of formula II wherein $R^4$ is lower-alkyl or phenyl and $R_5$ is hydrogen may be synthesized by an alternate route from 2-cyclohexenone:

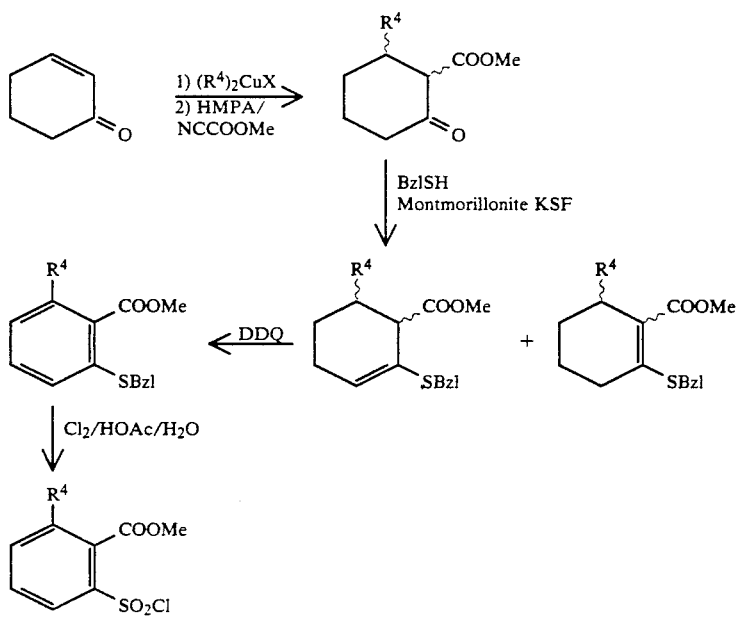

2-Cyclohexenone is reacted with the appropriate cuprate followed by methyl cyanoformate according to the method of Winkler et al. [*Tet. Lett.* 1987, 1051 and *J. Org. Chem.* 54, 4491 (1989)]. The resulting β-ketoester is reacted with benzylmercaptan in the presence of the acidic clay Montmorillonite KSF to produce a mixture of regioisomers of the benzylthioenol ether. The mixture is aromatized by treatment with dichlorodicyanobenzoquinone (DDQ) and oxidized with chlorine gas in aqueous acid to provide the sulfonyl chloride ester, which may then be converted to the intermediate II as shown earlier.

The 4,5,6,7-tetrahydrosaccharins which are the starting materials for the compounds of formula VI wherein $R^7$ is hydrogen are synthesized by a route similar to the preceding one:

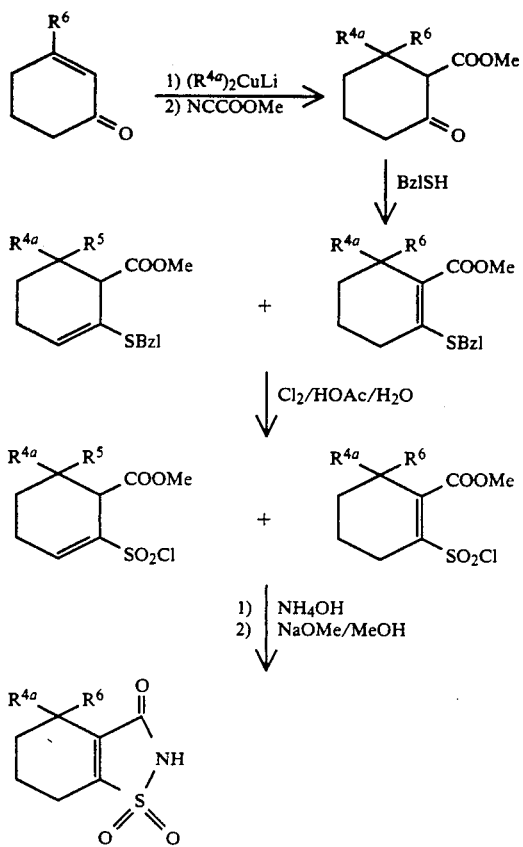

A 3-alkyl-2-cyclohexenone is reacted with the appropriate alkyl lithium cuprate in an ethereal solvent, preferably diethyl ether, at −50° to +20°, preferably about 0°, and the resulting adduct is treated in situ with methyl cyanoformate and hexamethylphosphoramide, The 6,6-dialkyl-2-oxocyclohexane carboxylate so produced is reacted with benzyl mercaptan as described above and the mixture of 2-(benzylthio)cyclohexane carboxylates is oxidatively chlorinated as described above to provide a mixture of chlorosulfonyl esters that are treated with ammonia as before to yield the desired 4,4-dialkyl-4,5,6,7-tetrahydrosaccharins.

The aryl carboxylic acids, Ar-COOH, used to prepare the final products of formula I and VI are members of a known class and can be prepared by well-known, conventional synthetic methods.

Chloromethyl esters of the aryl carboxylic acid may be prepared by treating the carboxylic acid with formaldehyde or a formaldehyde equivalent, preferably paraformaldehyde, in the presence of (1) a chloro acid, preferably zinc chloride or hydrochloric acid, or (2) trimethylsilyl chloride plus stannic chloride.

Simple chemical transformations which are conventional and well known to those skilled in the art of chemistry can be used for effecting changes in functional groups in the compounds of the invention. For example, catalytic reduction of nitro groups to produce the corresponding amino substituted compounds, acylation of amino-substituted species to prepare the corresponding amides, oxidation of sulfides or sulfoxides to prepare the corresponding, respective sulfoxides or sulfones, saponification of esters to produce the corresponding carboxylic acids, catalytic debenzylation of phenolic ethers or of benzylamines to produce the corresponding phenols or debenzylated amines or reaction of phenols with an alkylating agent in the presence of base to produce ethers as desired can be carried out.

In standard biological test procedures, the compounds of formula I and VI have been found to possess human leukocyte elastase (HLE) and chymotrypsin inhibitory activities, and are thus useful in the treatment of degenerative diseases, such as emphysema, rheumatoid arthritis, pancreatitis, cystic fibrosis, chronic bronchitis, adult respiratory distress syndrome, inflammatory bowel disease, psoriasis, bullous pemphigoid and alpha-1-antitrypsin deficiency.

The compounds of formula I and VI having basic functions can be converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the bases and all of their acid-addition salts are readily interconvertible.

Likewise certain compounds of formula I and VI having acid, i.e. carboxylic acid, functions can be converted to salt forms thereof by reaction of the acid with a base, such as alkali metal or ammonium hydroxides or with organic bases such as alkyl, dialkyl or trialkylamines, and the acids can be regenerated from the salts by treatment of the salts with aqueous acids.

It will thus be appreciated that formulas I and VI not only represent the structural configuration of the bases and acids, but are also representative of the structural entities which are common to all of the compounds of formulas I and VI whether in the form of the free base, the free acids or in the form of the salts of the bases and acids. It has been found that, by virtue of these common structural entities, the compounds of formulas I and VI and their salts have inherent pharmacological activity of a type to be more fully described hereinbelow. This inherent pharmacological activity can be enjoyed in useful form for pharmaceutical purposes by employing the free bases or free acids themselves or the salts formed from pharmaceutically acceptable acids and bases; that is, acids or bases whose anions or cations are innocuous to the animal organism in effective doses of the salts so that beneficial properties inherent in the common structural entity represented by the free bases and free acids are not vitiated by side effects ascribable to the anions or cations.

In utilizing this pharmacological activity of the salt, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base or aqueous acid as explained above, or alternatively they can be converted to any desired pharmaceutically acceptable salt by double decomposition reactions involving the anion or cation, for example by ionexchange procedures.

Moreover, apart from their usefulness in pharmaceutical applications, the salts are useful as characterizing or identifying derivatives of the free bases or free acids or in isolation or purification procedures. Like all of the salts, such characterization or purification salt derivatives can, if desired, be used to regenerate the pharmaceutically acceptable free bases or free acids by reaction of the salts with aqueous base or aqueous acid, or alternatively they can be converted to a pharmaceutically acceptable salt by, for example, ion-exchange procedures.

The novel feature of the compounds then resides in the concept of the 2-saccharinylmethyl aryl carboxylates of formulas I and VI not in any particular acid or base moiety or acid anion or base cation associated with the salt forms of the compounds.

The compounds of formulas I and VI of the invention can be prepared for pharmaceutical use by incorporating them in unit dosage form as tablets or capsules for oral administration either alone or in combination with suitable adjuvants such as calcium carbonate, starch, lactose, talc, magnesium stearate, gum acacia and the like. Still further, the compounds can be formulated for oral, parenteral or aerosol inhalation administration either in aqueous solutions of water soluble salts of the compounds or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and using his best judgment on the patient's behalf.

The molecular structures of the compounds of the invention were assigned on the basis of study of their infrared and NMR spectra. The structures were confirmed by the correspondence between calculated and found values for elementary analyses for the elements or by analysis of the high-resolution mass spectra.

The following examples will further illustrate the invention without, however, limiting it thereto. All melting points are uncorrected.

PREPARATION OF STARTING MATERIALS

Preparation 1

Powdered Potassium hydroxide (7.4 g, 0.132 mol) was admixed with dimethyl sulfoxide (DMSO) (100 ml), and the mixture was stirred for 5 minutes. 6-Methylanthranilic acid (10.0 g, 0.066 mol) was then added to the mixture and iodomethane (4.52 ml, 0.073 mol) added dropwise. The reaction mixture was stirred for 30 minutes at room temperature, then diluted with 250 ml of ether, washed with water (3×100 ml), dried over magnesium sulfate and concentrated. The crude product was filtered through a pad of flash grade (32-63) silica gel and eluted with 1:9 ether:hexane to afford 4.23 g (39%) of methyl 6-methylanthranilate as an oil.

The methyl 6-methylanthranilate so prepared (4.23 g, 0.026 mol) was dissolved in 25 ml of acetic acid and the solution cooled to 0° C. Concentrated hydrochloric acid (45 ml) was added to produce a tan slurry, A solution of 1.89 g (0.027 mol) of sodium nitrite in 8 ml water was added dropwise with stirring, the resulting orange solution was stirred at 0° C. for 1 hour and then added in 6 portions to a mixture of 2.18 g (0.013 mol) of cupric chloride dehydrate and sulfur dioxide (6.3 g) in 33 ml of acetic acid and 6 ml of water at 0° C. The dark green solution was stirred at room temperature overnight, poured into 300 ml of ice-water, and the solid which separated was collected and dried by suction to provide 1.11 g of methyl 2-chlorosulfonyl-6-methylbenzoate which was immediately added to 100 ml of ice cold ammonium hydroxide and stirred at room temperature overnight. The solution was acidified to pH 1 with concentrated hydrochloric acid, and the resulting precipitate was collected and air-dried to provide 729 mg (12%) of 4-methylsaccharin, mp 224°-2260 C.

A mixture of 1.0 g (0.005 mol) of 4-methylsaccharin, 0.33 g (0.001 mol) of TBAB and 1.2 g (0.0075 mol) of chloromethyl phenyl sulfide in 25 ml of toluene was heated under reflux for about sixteen hours and then cooled, diluted with ethyl acetate and the solution washed with aqueous bicarbonate and water. The organic layer was dried and taken to dryness to give 0.74 g of 2--phenylthiomethyl-4-methylsaccharin.

The latter (0.74 g, 0.002 mol) was dissolved in 25 ml of MDC and the solution treated dropwise over a period of about two hours with stirring with a solution of 0.47 g (0.003 mol) of sulfuryl chloride in MDC and the reaction mixture taken to dryness. The yellow residual solid was triturated with hexane and filtered and dried to give 0.46 g of 2-chloro-methyl-4-methylsaccharin as a pale yellow solid.

Preparation 2

Using the procedure described above in Preparation 1, 5.0 g (0.029 mol) of 6-chloroanthranilic acid and 2.75 ml (0.044 mol) of iodomethane were reacted in the presence of 4.08 g (0.073 mol) of powdered potassium hydroxide to give 4.22 g (78%) of methyl 6-chloroanthranilate as an oil.

4-Chlorosaccharin was prepared by the same method asused for the preparation of 4-methylsaccharin using 4.22 g (0.023 mol) of methyl 6-chloroanthranilate in 22 ml of acetic acid and 40 ml of concentrated hydrochloric acid and 1.68 g (0.024 mol) of sodium nitrite in 7 ml of water to prepare the diazonium salt which was added to 1.93 g (0.011 mol) of cupric chloride dehydrate and 6.5 g of sulfur dioxide in 30 ml of acetic acid and 5 ml of water. The resulting methyl 2-chlorosulfonyl-6-chlorobenzoate was treated with 150 ml of ammonium hydroxide as described above to afford 3.07 g (62%) of 4-chlorosaccharin as a pale yellow solid, mp 245°-246° C.

2-Hydroxymethyl-4-chlorosaccharin was prepared by heating a solution of 1.00 g (0.0046 mol) of 4-chlorosaccharin and 3.22 ml of aqueous 37% formalin in ethanol. All attempts to crystallize the viscous oily product resulted in decomposition to the starting material, and the product was thus used in the next step without characterization.

The crude 2-hydroxymethyl-4-chlorosaccharin so prepared (609 mg, 0.0025 mol) was admixed with 5 ml of diethylether, and 3 ml of thionyl chloride was added. The resulting mixture was heated to effect complete solution, stirred at room temperature overnight, diluted with 20 ml of ether and filtered through a pad of celite topped with sand and eluted with ether. Removal of the solvent afforded 430 mg of crude chloromethyl derivative. A portion (225 mg) was removed for further reactions. The remainder (205 mg) was flash chromatographed on silica gel and eluted with 40% ether/pentane to provide 137 mg of 2-chloromethyl-4-chlorosaccharin, mp 135°-1360° C.

Preparation 3A

To a suspension of 6.0 g (0.03 mol) of cuprous iodide in 100 ml of THF was added 25 ml of dimethyl sulfide, and the resulting yellow solution was cooled to −78° C. and treated dropwise with a solution of 23 ml (0.06 mol) of a 3.0M solution of phenyl magnesium bromide in diethyl ether. The resulting pale yellow-orange solution was stirred at −780° C. under nitrogen for one hour and then treated with 3.02 g (0.03 mol) of 2-cyclohexenone in 10 ml of THF. The resulting mixture was allowed to warm to 0° C. over a two hour period, recooled to −780° C., treated with 15 ml of hexamethylphosphoramide, stirred for thirty minutes, treated with 8.0 g (0.09 mol) of methyl cyanoformate and allowed to warm to ambient temperature overnight. The reaction mixture was poured into 100 ml of 2N hydrochloric acid, and the organic phase was separated and the aqueous phase backextracted with MDC. The combined organic extracts were taken to dryness in vacuo and the residue triturated with saturated ammonium chloride, then with water, then with brine and taken to dryness once again to give 3.2 g of methyl 2-phenylcyclohexan-6-one carboxylate as an oil.

The latter (3.0 g, 0.013 mol), 4.8 g (0.039 mol) of benzyl mercaptan and 1.0 g of Amberlyst ®15 resin (Rohm and Haas) in chloroform was heated under reflux for twenty hours, the mixture treated with an additional 1.5 g of the resin and heated for an additional four hours. The mixture was then cooled to ambient temperature, filtered, the filtrate taken to dryness in vacuo, the residue triturated with hexane and the solid collected by filtration to give 0.85 g (19%) of a mixture of methyl 2-benzylthio-6-phenylcyclohex-2-ene carboxylate and methyl 2-benzylthio-6-phenylcyclohex-1-ene carboxylate, 0.6 g (0.0018 mol) of which was heated with 2.0 g of 2,3-dichloro-5,6-dicyanobenzoquinone in 25 ml of toluene with stirring under nitrogen for twenty-four hours. The mixture was filtered through a pad of silica gel, eluting with 2:1 MDC:hexane, and the eluate was taken to dryness to give 0.3 g (67%) of methyl 2-benzylthio-6-phenylbenzoate.

The latter (0.52 g, 0.0016 mol) dissolved in 10 ml of MDC was diluted with 20 ml of acetic acid and 5 ml of water, the mixture cooled to −100° C., and chlorine gas was bubbled through the mixture until the exothermic reaction subsided. The mixture was then stirred for ten minutes and taken to dryness in vacuo to give 0.41 g (85%) of methyl 2-chlorosulfonyl-6-phenylbenzoate which was dissolved in 10 ml of THF and added to 25 ml of a solution of concentrated ammonium hydroxide while cooling in an ice/acetone bath. The reaction mixture was extracted with MDC, the organic phase discarded, and the aqueous layer acidified to pH 1 with concentrated hydrochloric acid and extracted with MDC. The organic extracts, on washing with brine, drying and evaporation to dryness, afforded 0.33 g (97%) of 4-phenylsaccharin.

Following a procedure similar to that described in Preparation 1, the latter (0.33 g, 0.0012 mol) was reacted with 0.3 g (0.0019 mol) of chloromethyl phenyl sulfide in 15 ml of toluene in the presence of 0.08 g (0.0025 mol) of TBAB and the product, 2-phenylthiomethyl-4-phenylsaccharin (0.48 g, 100%), treated with sulfuryl chloride in MDC to give 0.36 g (95%) of 2-chloromethyl-4-phenylsaccharin.

Preparation 3B

To a suspension of anhydrous CuCN (2.16 g, 0.025 mol) in anhydrous ether (100 mi) at −780° C. was added tert butyllithium (29.0 mL of 1.7M solution in pentane, 0.05 mol). After being stirred at −780° C. for 1 hr and at −450° C. for 30 minutes, the reaction mixture was recooled to −78° C. A solution of cyclohexenone (2.4 g, 0.025 mol) in ether (25 mL) was added and stirring continued for 15 minutes at −78° C. and at −45° C. for 30 minutes. The resulting mixture was recooled to −78° C., and HMPA (10 mi) in ether (25 mL) was added. After 5 min, methyl cyanoformate (2.55 g, 0.03 mol) in ether (25 mL) was added and the reaction warmed to 0° C. over a 2 hr period. The resulting mixture was quenched with 2N HCl (100 mL), the layers were separated, and the organic phase was washed with saturated NH$_4$Cl solution (3×50 mi), water (2×50 mi), brine (1×50 mi) and dried (Na$_2$SO$_4$). Removal of the solvent in vacuo and purification by Kugelrohr distillation (bath temperature 100°-1150° C. at 0.6 mm) afforded 4.7 g (88%) of methyl 2-(1,1-dimethylethyl)cyclohexan-6-one-carboxylate.

The cyclohexanone (4.6 g, 0.022 mol) was mixed with benzylmercaptan (2.95 g, 0.024 mol) and the acidic clay montmorillonite, KSF (7.5 g) in anhydrous toluene (7.5 mL). The mixture was refluxed under nitrogen with azeotropic removal of water for 6 hr, cooled to room temperature and let stand overnight. The solids were filtered off and washed with ether. The combined filtrate was washed with 10% Na$_2$CO$_3$, water, brine and dried. Removal of the solvent in vacuo and purification of the residue by flash chromatography on silica gel (10% ether in hexanes) gave 4.4 (66% of a mixture of methyl 2-benzylthio-6-(1,1-dimethylethyl)cyclohex-2-ene carboxylate and 2-benzylthio-6-(1,1-dimethylethyl)cyclohex-1-ene carboxylate, which was stirred with DDQ (17.5 g, 0.077 mol) in toluene (50 mL) for 16 hr. The red reaction mixture was filtered through a 15 cm pad of silica gel, eluting with 6:3:1 hexanes:MDC:ether (1000 mL). The eluents were washed with 10% NaOH solution, water, brine and dried. Removal of the solvent in vacuo and purification by chromatography on silica gel (5% ether in hexanes) gave 1.6 g (40%) of methyl 2-benzylthio-6-(1,1-dimethyl)benzoate.

The benzylthiobenzoate (1.3g, 0.004 mol) dissolved in MDC (5 mL) was diluted with acetic acid (25 mL) and water (2 mL), the mixture cooled to −10° C., and chlorine gas was bubbled until the exothermic reaction subsided. the mixture was then stirred for 10 minutes and taken to dryness in vacuo. Purification of the residue by flash chromatography on silica gel (1:1 hexanes:MDC) gave 0.8 g (67%) of 2-chlorosufonyl-6(1,1-dimethylethyl)benzoate, which was dissolved in THF (5 mL) and added to a solution of concentrated ammonium hydroxide (25 mL) while cooling in an ice/acetone bath. After stirring at room temperature for 16 hr, the reaction mixture was concentrated in vacuo and acidified to pH 1 with 2N HCl. The separated solids were collected by filtration and cystallized from ether to give 0.64 g (95%) of 4-(1,1-dimethylethyl)saccharin, mp 185°-187° C.

The 4-(1,1-dimethylethyl)saccharin (0.025 g 1.0 mmol) was mixed with chloromethyl phenyl sulfide (0.25 g, 1.5 mmol) and tetrabutyl ammonium bromide (0.2 g, 0.6 mmol) in toluene (25 mL) and refluxed under nitrogen for 16 hr. The resulting mixture was cooled to room temperature, evaporated to dryness and purified by chromatography on silica gel (80%) MDC in hexanes) to give 0.35 g (98%) of 2-phenylthiomethyl-4-(1,1-dimethylethyl)saccharin, which was treated with sulfuryl chloride (0.25 g, 1.8 mmol) in MDC to give 0.21 g (75%) of 2-chloromethyl-4-(1,1-dimethylethyl)saccharin.

Preparation 4

A mixture of 3.22 g (0.012 mol) of 4-bromosaccharin (Japanese Pat. Publcn. 58/79,034, published May 12, 1983; C.A. 100, 7773w (1984)), 1.63 g (0.015 mol) of potassium t-butoxide, 0.39 g (0.0012 mol) of TBAB and 3.0 ml (0.022 mol) of chloromethyl phenyl sulfide in 100 ml of toluene was heated under reflux under a nitrogen atmosphere for eight hours and then stirred at ambient temperature for about sixteen hours. The reaction mixture was then diluted with ethyl acetate, and the organic layer was washed with dilute potassium carbonate, water and brine, dried over magnesium sulfate and taken to dryness in vacuo. The residual solid was recrystallized from toluene-hexane to give 3.86 g (84%) of 4-bromo-2-phenyl-thiomethylsaccharin, mp 174.5°-178° C.

To a solution of the latter (3.27 g, 0.0085 mol) in 85 ml of MDC was added, dropwise with stirring, 1.02 ml (0.0127 mol) of sulfuryl chloride. The mixture was stirred at ambient temperature for an hour and a half, concentrated in vacuo and the residue triturated with hexane and filtered to give 2.61 g of crude product which was recrystallized from toluene-hexane to give 2.24 g (85%) 2-chloromethyl-4-bromosaccharin, 157°-159° C.

Preparation 5

To a solution of 8.0 ml (0.053 mol) of tetramethylethylenediamine (TMEDA) in 350 ml of THF at −70° C. was added 42 mi (0.055 mol) of a 1.3M solution of s-butyl lithium in cyclohexane and the mixture was stirred for fifteen minutes. To the solution was added dropwise with stirring a solution of 10.36 g (0.050 mol) of 2-methoxy-N,N-diethylbenzamide in 150 ml of THF while maintaining the temperature at −60° C. or below. After stirring for 20 minutes sulfur dioxide was bubbled into the reaction mixture, keeping the reaction temperature below −50° C., until the reaction mixture was acid to wet litmus paper. The mixture was stirred at ambient temperature for two hours, diluted with 450 ml of hexane, and the solid material which had separated was collected, dissolved in 200 ml of water and the mixture treated with 65 g of sodium acetate and 21.5 g (0.19 mol) of hydroxylamine-O-sulfonic acid in portions with stirring. The white solid which separated was collected and dried to give 7.04 g (49%) of 2-aminosulfonyl-6-methoxy-N-,N-diethylbenzamide, mp 190°-194.5° C.

A mixture of the product (4.3 g, 0.015 mol) in 75 ml of dioxane and 25 ml of concentrated hydrochloric acid was heated on a steam bath for 70 hours, then cooled, concentrated in vacuo, diluted with water and ice and rendered strongly basic with concentrated sodium hydroxide. The mixture was washed with MDC, and the aqueous layer was acidified with dilute hydrochloric acid and extracted with MDC. The extracts were dried over magnesium sulfate and taken to dryness to give 1.29 g (40%) of 4-methoxysaccharin. In an alternative, and preferred, procedure, cyclization of 2-aminosulfonyl-6-methoxy-N,N-diethylbenzamide to 4-methoxysaccharin in 65% yield was carried out in refluxing glacial acetic acid for six and a half hours.

Following a procedure similar to that described in Preparation 4 above, 1.14 g (0.0053 mol) of the latter was reacted with 1.31 ml (0.0097 mol) of chloromethyl phenylsulfide in toluene in the presence of 0.72 g (0.0064 mol) of potassium t-butoxide and 174 mg (0.00054 mol) of tetrabutylammonium bromide to give 1.23 g (69%) of 4-5methoxy-2-phenylthiomethylsaccharin, mp 152.5°-154.50° C. (from ethyl acetate-hexane), 1.02 g (0.003 mol) of which was treated with 0.36 ml (0.0045 mol) of sulfuryl chloride in MDC to give 282 mg (36%)of 2-chloromethyl-4-methoxy-saccharin, mp 169°-1740° C.

Preparation 6A

To a solution of 4.74 ml (0.031 mol) of tetramethylethylenediamine in 300 ml of THF (passed through alumina prior to use) was added 5.8 g (0.03 mol) of 2-ethyl-N,N-diethyl-benzamide. The solution was cooled to −78° C. and treated with 34.9 ml (0.031 mol) of a 0.9 M solution of s-butyl lithium in cyclohexane. When addition was complete, the mixture was stirred for twenty minutes and then treated with a solution of 3.2 ml (0.04 mol) of ethyl iodide while maintaining the temperature at −78° C. The temperature was then allowed to rise to ambient temperature and the mixture stirred for about sixteen hours and then poured into water. The resulting oil was separated and chromatographed on silica gel, eluting with 10% ethyl acetate/hexane to give 2.86 g (43%) of 2-sec.-butyl-N,N-diethylbenzamide as a yellow oil.

Following a procedure similar to that described in Preparation 5 above, the latter (10.45 g, 0.045 mol), dissolved in 70 ml of THF, was added to a solution of 39.2 ml (0.047 mol) of a 1.2 M solution of s-butyl lithium in cyclohexane and 7.1 ml (0.047 mol) of tetramethylethylenediamine in 250 ml of THF while maintaining the temperature at −78° C. When addition was complete the mixture was stirred for an additional one half hour at −78° C. and then treated with sulfur dioxide at −70° C. and then allowed to warm to room temperature. The mixture was taken to dryness in vacuo, and the residue was dissolved in water and added with stirring to a cold solution of 15.2 g (0,134 mol) of hydroxylamine-O-sulfonic acid and 15.4 ml (0.134 mol) of 35% sodium hydroxide to give 10.1 g (72%) of 2-aminosulfonyl-6-sec.-butyl-N,N-diethylbenzamide.

The latter (6.83 g, 0.22 mol) was dissolved in 100 ml of glacial acetic acid and the solution heated under reflux for thirteen hours and then taken to dryness. The residue was triturated with diethyl ether and collected by filtration to give 5.7 q (83%) of the diethylammonium salt of 4-sec.-butylsaccharin.

The latter (3.0 g, 0.0096 mol), on reaction with 1.13 ml (0.012 mol) of chloromethyl phenyl sulfide in toluene, afforded 3.47 g (100%) of 2-phenylthiomethyl-4-sec.-butylsaccharin.

Reaction of the latter (3.2 g, 0.0097 mol) with 2.3 ml (0.029 mol) of sulfuryl chloride in 20 ml of MDC afforded 2.4 g (87%) of 2-chloromethyl-4-sec.-butylgarcharin.

Preparation 6B

By a procedure analogous to that described for Preparation 6A, 9.2 g (32.9 mmol) of 3,4,dimethoxy-2-propyl-N,N-diethylbenzamide was reacted with sulfur dioxide and 5.6 g (49.4 mmol) of hydroxylamine-O-sulfonic acid to provide 7.4 q (63%) of 2-aminosulfonyl-4,5-dimethoxy-6-propyl-N,N-dimethylbenzamide which was cyclized in quantitative yield in acetic acid and phenylthiomethylated with 1.42 mL (15 mmol) of chloromethyl phenyl sulfide to provide 4.07 g of 5,6-dimethoxy-2-phenylthiomethyl-4-propylsaccharin. Reaction of 3.59 g (8.8 mmol) of the phenylthioether with 2.12 mL (26.4 mmol) sulfuryl chloride provided 2.84 g (97%) of 2-chloromethyl-5,6-dimethoxy-4-propylsaccharin.

The 3,4-dimethoxy-2-propyl-N,N-diethylbenzamide was obtained by the following procedure:

To a solution of .216 moles of n-butyllithium in 250 mL of ether at ambient temperature was added dropwise 138.2 g (0.216 mol) of veratrol in 100 mL of ether and 32.6 mL (0.216 mol) of TMEDA. The reaction was stirred at 5ambient temperature 14 hours and 21.9 mL (0.225 mol) of n-propyl iodide was added with cooling. The reaction was stirred 1 hour at RT and worked up with aqueous 1N HCl to give 14 g (36%) of 2.3-dimethoxybenzenepropane which was brominated with 14.52 g (81.6 mmol) of N-bromosuccinimide on 36 g of Kieselgel in 400 mL of CCl$_4$ according to the method of Hisatoshi et al. [*Bull. Chem. Soc. Jap.*32, 591–593 (1989)] to give 19.6 g (98%) of 6-bromo-2,3-dimethoxybenzenepropropane.

The bromobenzene (14.2g, 54.8 mmol) was dissolved in 200 mL ether, cooled to −78°, and 25.2 mL (63 mmol) of 2.5 N n-butyllithium in hexane was added. The reaction was warmed to 0°, held for an hour, and cooled to −70°, and 9 mL (71.2 mmol) of diethyl carbamyl chloride was added. The reaction was allowed to come to RT and was quenched with saturated ammonium chloride. After extraction and drying, the product was crystallized from hexane to provide 9.5 g (62%) of 3,4-dimethoxy-2-propyl-N,N-diethylbenzamide, mp 65°–67°.

Preparation 6C

By a process analogous to that of preparation 6B, 10.75 g (30 mmol) of 6-aminosulfonyl-3,4-dimethoxy-2-isopropyl-N,N-diethylbenzamide was cyclized to provide 6.43 g of 5,6-dimethoxy-4-isopropyl saccharin (mp 186–188 from ether-hexane), 5 g (17.5 mmol) of which was phenylthiomethylated with 2.48 mL (26.3 mmol) of phenylthiomethylchloride according to the procedure of Preparation 5, and chlorinated with 3 equivalents of sulfuryl chloride to provide an 85% yield of 2-chloromethyl-5,6-dimethoxy-4-isopropylsaccharin, mp 117°–119° from ethyl acetate-hexane.

The requisite benzamide was obtained from 2,3-dimethoxy-α-methylbenzeneethane by bromination followed by carbamylation as in Preparation 6B, to provide the intermediate 3,4-dimethoxy-2-isopropyl-N,N-diethylbenzamide. A solution of 66 mL of 0.96M sec-butyllithium was added to 16.1 g (57.6 mmol) of the benzamide in 400 mL of THF at −78° under nitrogen. After stirring 2 hours the orange anion was cannulated into excess sulfur dioxide at −60°. The reaction was allowed to come to room temperature and stirred for 18 hrs to remove SO$_2$. Ten milliliters of sulfuryl chloride was added at 0° and the reaction was stripped. The sulfonyl chloride was extracted into EtOAc-ether, washed with water, dried and stripped. The residue was dissolved in 80 mL of THF and 17 mL of conc. NH$_4$OH was added at 0°. The reaction was stirred briefly at RT, stripped, and triturated in 2:1 ether-hexane to provide 12.89 g (62%) of 6-aminosulfonyl-3,4-dimethoxy-2-isopropyl-N,N-diethylbenzamide, mp 138°–140°.

Preparation 7

To a solution of 9.3 ml (0.058 mol) of tetramethylethylenediamine in 340 ml of THF at −78° C. was added 52 ml of a 1.1 M solution (0.057 mol) of s-butyl lithium in cyclohexane. The solution was then treated with a solution of 11.37 g (0.052 mol) of 2-propyl-N,N-diethylbenzamide in 75 ml of THF at −78° C. and the solution stirred for fifteen minutes and then treated with a solution of 8.3 ml (0.104 mol) of ethyl iodide in THF. The solution was stirred for an hour and a half at −78° C. and then quenched by the addition of saturated ammonium chloride added dropwise at −78° C. The mixture was then allowed to warm to ambient temperature, diluted with diethyl ether, washed first with dilute hydrochloric acid, then with water, then with saturated sodium bicarbonate, then with brine, dried and taken to dryness to give 12.91 g of crude product which was chromatographed on silica gel, eluting with 10% ethyl acetate/hexane to give 3.23 g (25%) of 2-(3-pentyl)-N,N-diethylbenzamide as a yellow oil.

Following a procedure similar to that described in Preparation 5 above, the latter (3.05 g, 0.0115 mol) in THF was reacted with 10.5 ml (0.126 mol) of a 1.2 M solution of s-butyl lithium in cyclohexane in the presence of 2.1 ml (0.014 mol) of tetramethylethylenediamine. The resulting lithium salt was then reacted first with sulfur dioxide and then with sodium hydroxylamine-O-sulfonate to give 1.97 g (52%) of 2-aminosulfonyl-6-(3-pentyl)-N,N-diethylbenzamide as pale yellow crystals, mp 118°–120° C. (soft 102°), 1.84 g (0.0056 mol) of which was cyclized in 22 ml of refluxing glacial acetic acid to give 1.28 g (70%) of the diethylammonium salt of 4-(3-pentyl)saccharin, mp 107.5°–109.5° C.

The latter (0.0037 mol), on reaction with 0.74 ml (0,0055 mol) of chloromethyl phenyl sulfide in the presence of 116 mg (0.0004 mol) of TBAB in 45 ml of toluene, afforded 1.93 g of 2-phenylthiomethyl-4-(3-pentyl)-saccharin as a pale yellow oil, 1.93 g (0.0037 mol) of which, on reaction with 0.59 ml (0.0073 mol) of sulfuryl chloride in 37 ml of MDC, afforded 1.2 g of 2-chloromethyl-4-(3-pentyl)saccharin as a pale yellow oil.

Preparation 2

A solution of 50.0 g (0.27 mol) of 2,4-dimethoxybenzoic acid in 60 ml (98.0 g, 0.82 mol) of thionyl chloride was heated under reflux for three hours, then cooled, and the excess thionyl chloride distilled off. The resulting 2,4-dimethoxybenzoyl chloride was dissolved in 150 ml of MDC and the solution treated with a solution of 68 ml (48 g, 0.66 mol) of diethylamine in 500 ml of MDC, cooled to 0° C. When addition was complete the mixture was stirred for fifteen hours at ambient temperature, then washed with saturated sodium bicarbonate, water and brine and taken to dryness and the residue distilled in vacuo to give 44.78 g (69%) of 2,4-dimethoxy-N,N-diethylbenzamide, b.p. 155°-163° C./0. 4 mm.

Following a procedure similar to that described in Preparation 5 above, 10.0 g (0.042 mol) of the product in 250 ml of THF was reacted with 40.57 ml of a 1.1 M solution (0.044mol) of s-butyl lithium in cyclohexane and 6.35 ml (0.042 mol) of tetramethylethylenediamine in THF. The resulting lithium salt was then reacted first with about 40 ml of sulfur dioxide and then with an aqueous solution (0.13 mol) of sodium hydroxylamine-O-sulfonate to give 8.26 g of 2-aminosulfonyl-4,6-dimethoxy-N,N-diethylbenzamide, 7.0 g of which (0.022 mol) was cyclized in 80 ml of refluxing glacial acetic acid to give 6.6 g (94%) of the diethylammonium salt of 4,6-dimethoxy-saccharin which was used as such in the next step without further purification.

The latter (6.0 g, 0.019 mol), on reaction with 3.82 ml (0.028 mol) of chloromethyl phenyl sulfide in the presence of 0.611 g (0.0019 mol) of TBAB in 200 ml of toluene, afforded 6.2 g (89%) of 2-phenylthiomethyl-4,6-dimethoxysaccharin, 5.82 g of which (0.016 mol), on reaction with 3.23 g (0.0019 mol) of sulfuryl chloride in 100 ml of MDC, afforded 4.63 g (100%) of 2-chloromethyl-4,6-dimethoxysaccharin, m.p. 185°-187° C.

Preparation 9A-9G

Following a procedure similar to that described above in Preparation 5, substituting for the 2-methoxy-N,N-diethylbenzamide used therein an appropriate 2-$R^4$-$R^5$-substituted-N,N-diethylbenzamide, the following 2-halomethyl-4-$R^4$-$R^5$-saccharins listed in TABLE A were prepared via the corresponding 2-phenylthiomethylsaccharins. Wherever available, the melting point, recrystallization solvent and yield are given for each of the 2-unsubstituted saccharins, the 2-phenylthiomethylsaccharins and the 2-chloromethylsaccharins in columns headed "mp/Solv." and "Yield". In all instances, the intermediate 2-phenylthiomethylsaccharins were used directly in the subsequent step without further characterization or purification.

(70%) of 2-hydroxymethylsaccharin. The latter (25 g, 0.117 mol) was reacted with 63.3 g (0.234 mol) of phosphorus tribromide in diethyl ether to give 29.8 g (92%) of 2-bromomethylsaccharin, mp 155°-157° C.

Preparation 11

To a solution of 4 g (0.0175 mol) of 6-nitrosaccharin in 240 ml of ethanol was added 4.4 g (0.0175 mol) of thallium ethoxide, and the mixture was allowed to stand at room temperature for one hour, cooled for about 16 hours and the precipitated solid collected and dried to give 7.6 g (100%) of the thallium salt of 6-nitrosaccharin. The product was suspended in 50 ml of DMF and the mixture treated with 3.07 g (0.0194 mol) of chloromethyl phenyl sulfide, the mixture warmed at about 63°°C. for five hours, allowed to stand at ambient temperature for about 16 hours, and then poured into ice water. The crude product, obtained by filtration, was stirred in MDC and filtered to remove thallium salts, The filtrate was freed of solvent, and the resultant pale yellow solid was sonicated with warm ethanol and once again collected and dried to give 4.6 g (75%) of 6-nitro-2-phenylthiomethylsaccharin, mp 161°-163° C. The latter, on reaction with sulfuryl chloride in MDC using the procedure described above in Preparation 4, afforded 3.7 g of 2-chloromethyl-6-nitrosaccharin.

Preparation 12

A solution of 49.8 g (0.199 mol) of 2-hydroxy-5-(1,1,3,3-tetramethylbutyl)benzoic acid in 200 ml of methanol was heated to 50° C. and then treated dropwise with about 80 g of sulfuric acid at a rate to maintain the reaction under reflux. The reaction mixture was heated under reflux for an additional 11 hours, then cooled and partitioned between water and ethyl acetate. The organic layer was washed with saturated sodium bicarbonate, then with brine, dried over sodium sulfate and taken to dryness to give 48.6 g (92%) of methyl 2-hydroxy-5-(1,1,3,3-tetramethylbutyl)benzoate.

The latter dissolved in 250 ml of DMF was treated first with 40.4 g (0.36 mol) of 1,4-diazabicyclo[2.2.2]octane followed by 33.4 g (0.27 mol) of N,N-dimethylchlorothiocarbamate and 100 ml of DMF. The reaction

TABLE A

| | | Sacc | | 2-$C_6H_5SCH_2$-Sacc | | 2-$ClCH_2$-Sacc | |
|---|---|---|---|---|---|---|---|
| Prep | $R^4/R^5$ | mp/Solv | Yield | mp/Solv | Yield | mp/Solv | Yield |
| 9A | H<br>7-Cl | 260–262 | 93 | — | 100 | 158.0–160.0<br>i-PrOH | 51 |
| 9B | CH(CH$_3$)$_2$<br>H | 177.0–178.0<br>MeOH | 88 | — | 100 | 93.0–96.0<br>i-PrOH-Cyc hex | 100 |
| 9C | CH$_3$O<br>5-CH$_3$O | (a) | 64 | — | 100 | 190.0–192.0 | 76 |
| 9D | COOCH$_3$<br>H | (b)<br>EtOAc-hex | 76 | — | 65 | 186.0–187.0 | |
| 9E | C$_2$H$_5$O<br>H | (a) | 96 | — | 95 | 139.0–140.0 | 97 |
| 9F | (CH$_3$)$_2$CHO<br>H | | 87 | — | 75 | 142.5–143.5 | 94 |
| 9G | C$_2$H$_5$<br>5,7-(CH$_3$O)$_2$ | i-PrOH | 67 | — | 52 | — | 99 |

(a) Isolated and used in the next step as the diethylammonium salt.
(b) The 2-unsubstituted-saccharin was prepared by cyclization of dimethyl 3-aminosulfonylphthalate in methanol in the presence of a molar equivalent of sodium methoxide. The phthalate ester was prepared by diazotization of dimethyl 3-aminophthalate, decomposition of the diazonium salt with sulfur dioxide in the presence of cupric chloride and reaction of the resulting dimethyl 2-chlorosulfonylphthalate with ammonia. (84% yield overall).

Preparation 10

Following a procedure similar to that described in Preparation 2, reaction of 18.3 g (0.1 mol) of saccharin with 70 ml of 37% formalin in ethanol afforded 3.58 g mixture was heated at 450C for about eight hours, cooled, poured into ice/water-and concentrated hydrochloric acid and then extracted with ethyl acetate. The combined organic extracts were washed with dilute hydrochloric acid, then with sodium bicarbonate and then with brine, dried and taken to dryness to give 48.2 g (76%) of methyl 2-(N,N-dimethylthiocarbamyloxy)-5-(1,1,3,3-tetramethylbutyl)benzoate which was heated at 220° C. for 15 hours, then cooled, dissolved in toluene and chromatographed on silica, eluting with 1:9 ethyl acetate:toluene, to give 3.6 g (14%) of methyl 2-(N,N-dimethylcarbamylthio)-5-(1,1,3,3-tetramethyl)benzoate.

A solution of the latter (0.025 mol) in 40 ml of MDC was treated, with stirring, with 80 ml of glacial acetic acid, followed by 16 ml of water. The reaction mixture was cooled to 0° C., and chlorine was bubbled through the reaction mixture for about five minutes while maintaining the temperature between 5° and 24° C. The reaction was stirred for an additional 30 minutes, concentrated in vacuo, and the remaining solution poured into ice water. Extraction of the mixture with ethyl acetate and isolation of the product from the combined organic extracts afforded 6.8 g (78%) of methyl 2-chlorosulfonyl-5-(1,1,3,3-tetramethylbutyl)benzoate.

The product (9.0 g, 0.026 mol) was dissolved in THF and added to 100 ml of concentrated ammonium hydroxide with cooling in an ice bath. The resulting solution was stirred for about 16 hours, then concentrated in vacuo and the concentrated solution acidified to pH 3 with concentrated hydrochloric acid. The mixture was stirred for several hours, and the separated solid collected, washed with water and dried to give 9.0 g of 5-(1,1,3,3-tetramethylbiatyl)saccharin, mp 213°–215° C.

Following a procedure similar to that described in Preparation 11, 9.0 g (0.30 mol) of the product was reacted with thallium ethoxide in ethanol and the resulting thallium salt reacted with 3.33 g (0.021 mol) of chloromethyl phenylsulfide in DMF to give 5.76 g (66%) of 2-phenylthiomethyl-5 (1,1,3,3-tetramethyl-butyl)saccharin, 3.3 g (0.007 mol) of which was treated with 0.944 g of sulfuryl chloride in MDC to give 1 g (41%) of 2-chloromethyl-5-(1,1,3,3-tetramethyl-butyl)-saccharin.

Preparation 13

Following a procedure similar to that described in Preparation 12 above, 15.5 g (0.086 mol) of ethyl 2-hydroxy-6-methylbenzoate was reacted with 15.9 g (0.129 mol) of N,N-dimethylchlorothiocarbamate in the presence of 19.3 g (0.172 mol) of 1,4-diazabicyclo(2.2.2)octane in DMF to give 22.1 g (96%) of ethyl 2-(N,N-dimethylthiocarbamyloxy)-6-methylbenzoate which was heated at 220° C. for about 10 hours. The product was purified by chromatography on silica gel in MDC to give ethyl 2-(N,N-dimethylcarbamylthio)-6-methylbenzoate as a red-brown oil.

A solution of the latter (22.6 g, 0.0844 mol) in 170 ml of MDC was treated with 340 ml of glacial acetic acid and 68 ml of water while cooling in an ice/acetone bath, and chlorine was bubbled through the reaction mixture for 10-15 minutes. The reaction vessel was evacuated to remove excess chlorine and MDC and the mixture poured into water and partitioned between MDC and water. The organic layer, on drying and evaporation to dryness, afforded 19 g of ethyl 2-chlorosulfonyl-6-methylbenzoate, 5 g (0.019 mol) of which was reacted with concentrated ammonium hydroxide in THF to give 6.1 g (67%) of 4-methylsaccharin.

Following a procedure similar to that described in Preparation 11 above, the product (10.1 g, 0.0512 mol) was converted to the thallium salt by reaction with 12.8 g (0,0512 mol) of thallium ethoxide in ethanol and the thallium salt reacted with 6.7 g (0.0427 mol) of chloromethyl phenyl sulfide in DMF to give 6.85 g (50%) of 2-phenylthiomethyl-4-methylsaccharin.

Reaction of the latter (6.7 g, 0.021 mol) with sulfuryl chloride in MDC afforded 4.9 g (95%) of 2-chloromethyl-4-methylsaccharin.

Preparation 14A

A mixture of 75 g (0.36 mol) of 3,3-dithiobispropionic acid, 102 ml of thionyl chloride and a catalytic amount of pyridine was stirred for about 24 hours and then evaporated to dryness in vacuo, The residue was treated with MDC and evaporated to dryness again to remove residual thionyl chloride and pyridine to give 87 g (98%) of the corresponding bis acid chloride, 44.8 g (0.18 mol) of which was dissolved in THF and added dropwise to a solution of 77.16 g (0.72 mol) of benzylamine in THF. The mixture was stirred for two hours at 40°–45° C., cooled and the precipitated solid collected, washed with water and dried to give 59 g (84%) of 3.3-dithiobis-propionic acid N,N'-dibenzylcarboxamide, mp 162°–165° C.

Reaction of 7.0 q (0.018 mol) of the latter with 10.25 g (0.076 mol) of sulfuryl chloride in MDC gave a mixture of 2-benzyl-2H-isothiazol-3-one and 5-chloro-2-benzyl-2H-isothiazol-3-one which were largely separated from one another by sonication in MDC (which solubilized most of the former). The insoluble material was collected by filtration and chromatographed on silica gel with MDC. There was thus obtained 5-chloro-2-benzyl-2H-isothiazol-3-one, mp 58°–680° C.

A solution of 10 g (0.044 mol) of the latter in MDC was cooled to 0° C. and the solution treated with 7.6 g (0.044 mol) of 3-chloroperbenzoic acid, the mixture stirred for 10 minutes and then treated with a second 7.6 g portion of the perbenzoic acid. The reaction mixture was filtered, the filter washed with MDC and the filtrate washed with saturated sodium bicarbonate, then with brine, dried over sodium sulfate and taken to dryness and the residue chromatographed in MDC on silica gel, the product being eluted with 50:50 hexane:MDC, to give 7.15 g (46%) of 5-chloro-2-benzyl-2-H-isothiazol-3-one-1-oxide.

A solution of 1.1 g (0.0045 mol) of the latter in 8 ml of benzene was treated with 0.55 g (0.0051 mol) of 2methoxyfuran and the solution heated in a pressure bottle at 70° C. for 1.5 hours and then cooled and the solid collected, washed with benzene and dried to give 2-benzyl-7-hydroxy-4-methoxybenzisothiazol-3-one-1-oxide, mp 235°–237° C.

A mixture of the product (1.85 g, 0.006 mol), 2,48 g (0.018 mol) of potassium carbonate and 1.70 g (0.012 mol) of methyl iodide in acetone was heated under reflux for 1.5 hours and then cooled and poured into water. The solid which separated was collected by filtration, washed with water and dried to give 1.70 g (89%) of 2-benzyl-4,7-dimethoxybenzisothiazol-3-one-1-oxide, 1.13 g (0.0035 mol) of which was oxidized with 1.20 g (0.007 mol) of 3-chloroperbenzoic acid in MDC using the procedure described above to give 1.03 g (88%) of 2-benzyl-4.7-dimethoxysaccharin.

A mixture of 2.07 g (0.0062 mol) of the product, 1.37 g (0.02 mol) of ammonium formate and 1.5 g of 10% palladium-on-charcoal catalyst in 80 ml of methanol was heated under reflux for one hour, then cooled and filtered, and the filtrate taken to dryness to give 0.92 g (57%) of the ammonium salt of 4,7-dimethoxysaccharin.

A solution of 1.11 g (0.0042 mol) of the ammonium salt was dissolved in DMF, 0.67 g (0.0042 mol) of chloromethyl phenyl sulfide was added, and the solution heated under reflux for eight hours and then cooled and poured into ice water. The solid which separated was collected, washed with water and dried to give 0.50 g (33%) of 2-]phenyl -4,7-dimethoxysaccharin, Reaction of the latter (0.5 g, 0.0013 mol) with sulfuryl chloride in MDC using the procedure described above in Preparation 4 afforded 0.22 g (58%) of 2-chloromethyl-4,7-dimethoxysaccharin.

Preparations 14B and 14C

Following a procedure similar to that described in Preparation 14A, other 2-chloromethylsaccharin derivatives were prepared as follows:

Preparation 14B

Reaction of 5.8 g (0.024 mol) of 5-chloro-2-benzyl-2H-isothiazol-3-one-1-oxide with 3.76 g (0.0335 mol) of 2-ethoxyfuran afforded 3.05 g (40%) of 2-benzyl-4-ethoxy-7-hydroxybenzisothiazol-3-one-1-oxide, 5.7 g of which was reacted with 3.6 g 10.0197 mol) of 2-[2-methoxyethoxy]ethyl bromide in the presence of 4.95 g (0.0358 mol) of potassium carbonate in 125 ml of methyl ethyl ketone and 25 ml of DMF to give 7.0 g (93%) of 2-benzyl-A-ethoxy-7-[2-(2-methoxyethoxy]benzisothiazol-3-one-1-oxide, which was oxidized as before with 3-chloroperbenzoic acid in MDC to give 2-benzyl -f2-(2-methoxyethoxy)ethoxylsaccharin. Debenzylation of 6.6 g (0.015 mol) of the latter with 3.34 g (0.053 mol) of ammonium formate in the presence of 6.4 g of 10% palladium-on-charcoal catalyst in methanol afforded the ammonium salt of 4-ethoxy-7-r2-(2-methoxyethoxy)ethoxy]saccharin, which was reacted with 2.38 g (0.015 mol) of chloromethyl phenyl sulfide in 100 mL of DMF to give 1.46 g (21%) of 2-phenylthiomethyl-4-ethoxy-7-[2-(2-methoxyethoxy)-ethoxy]saccharin, mp 73°-75° C. (from isopropanol). Treatment of 1.4 g (0.0029 mol) of the product with 0.4 g (0.0029 mol) of sulfuryl chloride in MDC afforded 1.16 g (100%) 2-chloromethyl-4-ethoxy-7-[2-(2-methoxyethoxy)ethoxy]-saccharin.

Preparation 14C

Reaction of 3.03 g (0.01 mol) of 2-benzyl-7-hydroxy-4-methoxybenzisothiazol-3-one-l-oxide (Preparation 14A) with 2.01 g (0.011 mol) of 2-(2-methoxyethoxy)ethyl bromide in methyl ethyl ketone in the presence of 2 g (0.015 mol) of potassium carbonate afforded 2.58 g (64%) of 2-benzyl-4-methoxy-7-[2-(2-methoxyethoxy)ethoxy]benzisothiazol-3-one-1-oxide, which, on oxidation with 1.1 g (0.0063 mol) of 3-chloroperbenzoic acid in MDC, gave 2-benzyl-4-methoxy-7-[2-(2-methoxyethoxy)ethoxy]saccharin. Debenzylation of 0.25 g (0.0006 mol) of the product with 0.13 g (0.0021 mol) of ammonium formate in methanol in the presence of 0.25 g of 10% palladium-on-charcoal gave 0.21 g (100%) of the ammonium salt of 4-methoxy-7-[2-(2-methoxyethoxy)ethoxy]saccharin. Reaction of 1.4 g (0.004 mol) of the ammonium salt with 0.63 g (0.004 mol) of chloromethyl phenyl sulfide in DMF afforded 2-phenylthiomethyl-4-methoxy-4-[2-(2-methoxyethoxy)ethoxy]saccharin, which, on reaction with sulfuryl chloride in MDC, afforded 0.53 g (35%) of 2-chloromethyl-4-methoxy-7-[2-(2-methoxyethoxy) ethoxylsaccharin.

Preparation 15

A solution of 1.89 g (0.011 mol) of diethylamino sulfur trifluoride (DAST) in 20 ml of MDC was added to a suspension of 2.13 g (0.01 mol) of 2-hydroxymethylsaccharin in 25 ml of MDC while maintaining the reaction mixture at −78° C.

The reaction mixture was stirred at −78° C. for one hour, the temperature allowed to slowly rise to ambient temperature, the mixture stirred for 16 hours and then poured into ice-water. The organic layer was separated and washed with water, dried over magnesium sulfate and taken to dryness to give 2.2 g of product which was recrystallized from ethyl acetate to give 1.6 g (74%) of 2-fluoromethylsaccharin, mp 96°-98° C.

Preparation 16A

To a solution of 0.5 g (0.0025 mol) of 4-methylsaccharin in THF cooled to −78° C. by a dry ice/acetone bath was added, dropwise with stirring, a solution of 5.2 ml of 10 a 1.3 M solution of s-butyl lithium in cyclohexane. The mixture was stirred an additional hour at −78° C. and then treated with 0.16 ml (0.025 mol) of methyl iodide over a 1½ hour period. The mixture was stirred for an hour and 45 minutes, quenched in 25 ml of 1N hydrochloric acid, the reaction mixture rendered basic, the aqueous mixture extracted with chloroform and then acidified and extracted with ethyl acetate. The combined organic extracts were washed with 10% sodium thiosulfate, then with brine, dried over sodium sulfate and taken to dryness to give a product, whose PMR spectrum indicated a mixture consisting of 74% of 4-ethylsaccharin and 21% of 4,7-dimethylsaccharin.

Following a procedure similar to that described in Preparation 4 above, the crude material (0.47 g, 0.0022 mol) was reacted with 0.24 ml (0.0028 mol) of chloromethyl phenylsulfide in toluene in the presence of tetrabutylammonium bromide, and the product chromatographed on silica gel, eluting with MDC, 5 ml fractions being collected. The first 420 ml of eluate were discarded. The next 20 fractions, on evaporation, afforded 0.07 g of material, predominantly 2-phenylthiomethyl-4,7-dimethylsaccharin, which was set aside. The next 25 fractions afforded 0.37 g of 2-Rhenyl 1-4-ethylsaccharin, which was reacted with sulfuryl chloride in MDC to give 0.19 g (66%) of 2-chloromethyl-4-ethylsaccharin,

Preparation 16B

Following a procedure similar to that described in Preparation 16A, 10 g (0.051 mol) of 4-methylsaccharin in THF was reacted with 86 ml (0.10 mol) of a 1.18 M solution of s-butyl lithium in cyclohexane and the resulting solution treated with 4.5 ml (0.050 mol) of ethyl iodide to give 10.15 g (89%) of 4-prolpylsaccharin, which, on reaction with '5.32 ml (0.056 mol) of chloromethyl phenyl sulfide in toluene in the presence of tetrabutylammonium bromide, afforded a crude mixture from which was isolated by flash chromatography on silica gel 2-Rhenylthiomethyl-4-propylsaccharin as an oil, 1.8 g (0.0052 mol) of which, on reaction with 1.25 ml (0.016 mol) of sulfuryl chloride in MDC, afforded 0.94 g (66%) of 2-chloromethyl-4-propylsaccharin.

Preparation 16C

A preferred alternative to preparation 16A is as follows:

To a solution of 5.13 g (25 mmol) of N,N,2-triethylbenzamide in THF (50 ml) at −78° was added a solution of LDA (Aldrich 2.0M, 15.63 mL, 31.25 mmol). The solution was warmed to −10° C. with ice water over 1 hr, then cooled to −78° C. with dry ice-acetone. TMSCl (6.34 mL, 50 mmol) was added neat at −78° C. and then reaction brought to room temperature after 1 hr. The reaction was quenched with saturated $NH_4Cl$ and extracted with ether (2×100 mL), dried over $MgSO_4$, stripped and the residue distilled in a Kugelrohr (130°-140° C., 0.65 mm) to obtain 6.51 g (94%) of N,N-diethyl-2-[1-(trimethylsilyl)ethyl]benzamide.

To a solution of sec-BuLi (0.97M, 5.10 mL, 4.96 mmol) and TMEDA (0.75 mL, 4.96 mmol) in THF at −78° C. was added the amide (1.25 g, 4.50 mmol) in THF. Excess $SO_2$ in THF was added quickly at −78° C. then warmed to room temperature. The THF was removed in vacuo and the residue treated at 0° C. with two equivalents of a 1:1 solution of sodium hydroxide (0.36 g, 9.0 mmol) and hydroxylamine-O-sulfonic acid (1.0 g, 9.0 mmol) in $H_2O$. The reaction was stirred at room temperature for 4 hrs, extracted with EtOAc, dried over $MgSO_4$, concentrated and flash chromatographed on silica gel with 20% ethyl acetate/hexane to give 0.62 g (41%) of 2-aminosulfonyl-N-N-diethyl-6-[1-(trimethylsilyl)ethyl]benzamide. The benzamide (0.95 g, 2.66 mol) was refluxed in glacial acetic acid (20 ml) for 18 hr, stripped to dryness, triturated with hot cyclohexane (30 ml) and a trace of EtOAc (3 ml), cooled with scratching and filtered. There was obtained 0.81 g (85%) of 4-[1-(trimethylsilyl)ethyl]saccharin, mp 123°-125° C.

To the trimethylsilylethylsaccharin (0.25 g, 0.70 mmol) in DMF (9 ml) at room temperature was added $H_2O$ (1 mL) and cesium fluoride (0.75g 4.94 mmol, 7 equivalents). After 7 hr the reaction was poured into 5% NAOH and extracted with EtOAc. The aqueous layer was acidified with 12N HCl and extracted with $Et_2O$-EtOAc (1:1), dried over $Na_2SO_4$, filtered and stripped to give a colorless solid in quantitative yield. It was recrystallized from 5% $Et_2O$-hexanes to give 0.091 q (64%) of 4-ethylsaccharin, mp 183°-185° C.

Preparation 17

The 0.07 g sample of material obtained in the early fractions from the chromatographic separation described above in Preparation 16A consisting predominantly of 2-phenylthiomethyl-4,7-dimethylsaccharin was reacted with 0.05 ml of sulfuryl chloride in MDC and the product recrystallized from cyclohexane-ethyl acetate to give 20 mg (51%) of 2-chloromethyl-4,7-dimethylsaccharin, mp 107°-108° C.

Preparation 18A

To a solution of 40.0 g (0.174 mol) of 2-isopropyl-4-methoxybromobenzene in 600 ml of diethyl ether at 0° C. was added 103.68 ml (0.175 mol) of a 1.69 M solution of butyl lithium in diethyl ether. When the addition was complete the solution was cooled to 0° C. for one hour and stirred for an additional five hours at ambient temperature, then recooled to −78° C. and treated with a solution of 23.68 g (0.175 mol) of N,N-diethylcarbamyl chloride in 80 ml of diethyl ether. The resulting solution was stirred for about 12 hours while the reaction temperature was allowed to rise and then quenched with saturated ammonium chloride solution. The aqueous and organic layers were separated, the aqueous layer back extracted with ethyl acetate and the combined organic extracts washed once with brine, then dried and the solution taken to dryness to give a crude product which was flash chromatographed on silica gel, eluting with 30% ethyl acetate/hexane to give 34.4 g (79%) of 2-isopropyl-4-methoxy-N,N-diethylbenzamide as an oil which was used as such in the next step without further purification. The oil can be distilled, if desired, and boils at 123-129/0.2-0.3 mm.

Following a procedure similar to that described in Preparation 5 above, the latter (15.0 g, 0.060 mol) in 100 ml of diethyl ether was reacted with 77.8 ml (0.784 mol) of a 1.2M solution of s-butyl lithium in cyclohexane in the presence of 6.98 g (0.06 mol) of tetramethylethylenediamine. The resulting lithium salt was then reacted first with 50 ml of sulfur dioxide and then with 0.181 mol of sodium hydroxylamine-O-sulfonate to give 11.6 g (59%) of 2-aminosulfonyl-6-isopropyl-4-methoxy-N,N-diethylbenzamide, m.p. 103°-105° C. (from ethyl acetate/hexane). Eleven grams (0.034 mol) of the benzamide was cyclized in 200 ml of refluxing glacial acetic acid to give 10.3 g of the diethylammonium salt of 4-isopropyl-6-methoxysaccharin, m.p. 132°-135° C.

The latter (0.030 mol), on reaction with 6.14 ml (7.25 g, 0.046 mol) of chloromethyl phenyl sulfide in the presence of 0.98 g (0.003 mol) of TBAB in 250 ml of toluene, afforded 10.1 g (88%) of 2-phenylthiomethyl-4-isopropyl-6-methoxysaccharin as an oil, 9.7 g (0.026 mol) of which, on reaction with 3.1 ml (5.21 g, 0.039 mol) of sulfuryl chloride in MDC, afforded 6.9 g (88% of 2-chloromethyl-4-isopropyl-6-methoxysaccharin, mp 151°-152° C.

Preparation 18B

An alternative procedure was also followed:

To a solution of 300 mL of N,N,N',N'-tetramethylethylenediamine (TMEDA) (1.99 moles) in 4 L of anhydrous ether was added 1550 mL of sec-BuLi (1.3 M) and the system was cooled to −70° C. under a nitrogen atmosphere. A solution of 454.2 g of 2-isopropyl-4-methoxy N,N-diethylbenzamide (1.82 moles) in 300 mL of anhydrous ether was added dropwise over 30 minutes (the temperature was maintained at or below −60° C. during the addition). After the addition was complete, the reaction was stirred at −70° C. for one hour and allowed to warm to −50° C. After holding the temperature at −50° C. for 30 minutes, the mixture was cooled back to −70° C. To this stirred solution was added via cannulating tube a solution of 200 g of $SO_2$ in 200 mL of dry ether precooled to −40° C. under positive nitrogen pressure over a 20-minute period. The temperature of the reaction mixture during the addition was maintained below −40° C. (A white powdery precipitate of aryllithium sulphinate separated out almost immediately). After the addition, the icebath was removed and the reaction was allowed to stir at ambient temperature for two hours. It was cooled to −50° C. and to this stirred solution was added 190 mL of sulfuryl chloride (2.36 moles) dropwise over a 15-minute period maintaining the temperature below 10° C. during the addition. After further stirring for 30 minutes at 0°-50° C., a white insoluble precipitate was filtered off and washed with 2 L of anhydrous ether. Removal of the solvent at atmospheric pressure afforded the sulfonyl chloride as a crude dark oil. This crude sulfonyl chloride was dissolved in 1.4 L of THF, cooled to −10° C., and 540 mL of concentrated $NH_4OH$ (28%) was added in portions over 15 minutes (the temperature was kept at 15° C. or below throughout the addition). After stirring for 15 minutes at ambient temperature, the THF and excess ammonia were removed under vacuum to give a dark oil, which was diluted with 6.0 L of water and acidified with 3N HCl to pH 1. The light yellow solid was collected by filtration and washed with 800 mL of water. The solid was dried at 60° C. under vacuum for 18 hours and recrystallized from a mixture of 800 mL of ethyl acetate and 3 L of hexane to give 429 q (72%) of 2-aminosulfonyl-6-isopropyl-4-methoxy-N,N-diethylbenzamide, mp 122°-125° C.

A solution of 429.6 g of the diethylbenzamide (1.31 mole) in 1.5 L of acetic acid was refluxed for 20 hours. It was cooled to room temperature and the solvent removed under vacuum. The oily residue was dissolved in 6 L of water and adjusted to pH 1 with 6N HCl. The crude product was collected by filtration and washed with 2 L of water. The solid was dried at 60° C. under vacuum for 18 hours and recrystallized from ethyl acetate/hexane to give 303 g (91%) 4-isopropyl-6-methoxysaccharin, mp 188°.

To a suspension of 24 g of paraformaldehyde (0.8 mole) and 86.4 g of chlorotrimethylsilane (1.6 moles) in 200 mL of 1,2-dichloroethane was added 0.8 ml anhydrous tin(IV) chloride and the resulting solution stirred on a steam bath for one hour. At the end of this period, 51 g of 4-isopropyl-6-methoxysaccharin (0.2 mole) was added to the clear solution and the reaction mixture was further refluxed for 18 hours. It was cooled to room temperature, poured into water, the organic layer separated and washed with 50 mL of 2N sodium hydroxide solution. The organic layer was dried over anhydrous magnesium sulfate and concentrated under vacuum to give crude product. It was purified by crystallization from ethyl acetate/hexane to give 57 g (87%) of 2-chloromethyl-4-isopropyl-6-methoxysaccharin, mp 151.

Preparation 19

To a solution of 1.0 g (0.0039 mol) of 4-isopropyl-6-methoxysaccharin in 15 ml of MDC was added at ambient temperature 1.28 g (5.12 ml) of a 1 M solution of boron tribromide in MDC. When addition was complete the reaction mixture was heated under reflux for about five hours, cooled, taken to dryness in and the residue treated with ice and saturated sodium bicarbonate. The aqueous solution was extracted once with ethyl acetate and then acidified to pH 1 with concentrated hydrochloric acid. Extraction of the mixture with ethyl acetate/.diethyl ether (8:2), drying the organic extracts and removal of the solvent in vacuo afforded 0.9 g (96%) of 6-hydroxy-4-isopropylsaccharin as a white crystalline solid which was used as such in the next step.

An alternative procedure was also used. To a stirred suspension of 62.74 g (0.47 mol) of AlCl$_{13}$ in 500 mL of chloroform at 0° was added 43.9 g (0.7 mol) of ethanethiol. Within minutes a clear solution formed. To this a solution of 20.0 g (0.078 mol) of 4-isopropyl-6-methoxysaccharin in 550 mL of chloroform was added over a 30-min period. This solution was allowed to warm to RT and stirred for 3-4 hr at 60°. After cooling, the mixture was poured into ice-water and acidified with dilute HCl. The solid which separated was collected by filtration, washed with water and dried to give 18.4 g (97%) of 6-hydroxy-4-isopropylsarcharin.

Following a procedure similar to that described in Preparation 4 above, the latter (0.004 mol) was reacted with 0.61 ml (0.0046 mol) of chloromethyl phenyl sulfide in toluene in the presence of 0.133 g (0.004 mol) of TBAB to give 0.32 q (21%) of 4-isopropyl-6-hydroxy-2-phenylthiomethylsaccharin, m.p. 127°-129.5, 1.78 g of which was treated with 0.43 ml (0.73 g) of sulfuryl chloride in MDC to give 1.2 g (84%) of 2-chloromethyl-4-isopropyl-6-hydroxysaccharin, m.p. 149°-150° C.

Preparation 22

Five grams (0.0207 mol) of 6-hydroxy-4-isopropylsaccharin was dissolved in 150 ml of methanol and 3.4 g (0.0104 mol) of $Cs_2CO_3$ was added. The mixture was stirred for 3-4 hr at RT. The excess methanol was removed under reduced pressure and the residue was dried for 2 hr under high vacuum. The residue was then dissolved in 110 mL of DMF and 0.32 g (0.0209 mol) of chloromethyl phenyl sulfide was added. The stirred mixture was heated at 70°-750° for 12 hr, cooled, treated with ice water and extracted with 600 mL of 4:1 ethyl acetate:ether. The organic layer was washed with water and saturated NaCl and dried. The solvent was removed under reduced pressure. The residue was purified by flash chromatography with 20% ether in MDC. There was obtained 4.5 g (60%) of 4-isopropyl-6-hydroxy-2-phenylthiomethylsaccharin, mp 150°-151.5° C. which, on reaction with sulfuryl chloride as described in Preparation 19, yielded 2-chloromethyl-4-isopropyl-6-hydroxysaccharin as before.

Preparation 23

To a solution of 5-chloro-2-benzyl-4-isothiazolin-3-one (*J. Het. Chem.* 8, 571, 1971) (9.4 g, 0.04 mol) in MDC (100 mL) was added in one portion 80-85% 3-chloroperoxybenzoic acid (10.8 g, 0.06 mol) and the resulting mixture stirred at room temperature overnight under nitrogen. The precipitated solids were filtered off and washed with MDC (50 mi). The combined filtrate was evaporated to near dryness and the residue partitioned between ethyl acetate (300 mi) and saturated NaHCO$_3$ (100 mL). The layers were separated and the organic phase washed with saturated NaHCO$_3$ (2×100 mL), brine (1×100 mL) and dried. Removal of the solvent in vacuo afforded 10.0 g (99%) of 5-chloro-2-benzyl4-isothiazolin-3(2H)-one 1-oxide as a pale yellow oil.

The 1-oxide (10.0 g, 0.04 mol) in glacial acetic acid (200 mi) was treated with 30% $H_2O_2$ (100 mL, 0.88 mol) and heated on a steam bath for 2 hr during which time an additional 30 mL (0.26 mol) of 30% $H_2O_2$ was added. After heating on a steam bath for an additional hour, the reaction mixture was cooled to room temperature and poured into ice cold water (1L) and stirred. The precipitated solids were collected by filtration, washed with water (2×100 mL), hexanes and air dried to give 4.8 q (45%) of 5-chloro-2-benzyl-4-isothiazolin-3(2H)-one 1,1-dioxide as a colorless solid.

The dioxide (1.2 g 4.7 mmol) was mixed with 2,02 (11 mmol) of 2-trimethylsiloxy-5-methyl-hexa-1,3-diene (prepared from 5-methyl-hex-3-ene according to the method of E. J. Corey et al., *Tet. Lett.* 495, 1984) in toluene (50 mL) and refluxed for a period of 20 hr under nitrogen. The 15 resulting mixture was cooled to room temperature and concentrated in vacuo. The residue was dissolved in THF (25 mi) and treated with 2N HCl (10 mi). After stirring under nitrogen at room temperature for 10 min, ether (100 mi) was added and the layers separated. The organic phase was washed with water, brine, dried and evaporated to dryness to give a pale yellow foam. The foam was dissolved in toluene (30 mi), DBN (1.5 mi) was added and stirred at room temperature for 2 hr. MDC (100 mi) and 2N HCl (50 mL) were added and stirring continued for 5 min. The layers were separated and the organic phase washed with water, brine and dried. Removal of the solvent in vacuo and purification of the residue by flash chromatography on silica gel (5:4:1, hexanes:MDC:ether) gave 0.6 g (39%) of 2-benzyl-4-isopropyl6-oxo-tetrahydro-Saccharin as a pale yellow foam.

The tetrahydrosaccharin (0.59 g, 1.7 mmol) was dissolved in toluene (50 mi), dimethylamine hydrochloride (1.5 g, 18.0 mmol) and 4 A sieves (2.0 g) were added. The resulting mixture was refluxed with azeotropic removal of water for 96 hr. It was necessary to add additional dimethylamine hydrochloride (0.8 g, 10.0 mmol) and 4 A sieves every 12 hr during this 96 hr period at the end of which time, the reaction mixture was cooled to room temperature and filtered. The filter cake was washed with diethyl ether (100 mi) and the combined filtrates were concentrated in vacuo to give 0.63 g (99% of 2-benzyl4-isopropyl-6-dimethyl as a pale yellow solid.

To a solution of the dihydrosaccharin (0.63 g, 1.7 mmol) in refluxing chloroform (50 mi) was added activated manganese dioxide (4.3 g, 49.5 mmol) in portions over a period of 4 hr, After the addition of the last portion of manganese dioxide, the reaction was refluxed for an additional hr, cooled to room temperature and filtered through a pad of super cel, eluting with ethyl acetate. The combined eluents were concentrated in vacuo and the residue purified by flash chromatography on silica gel (5:4:1, hexanes:MDC:ether) to give 0.32 g (50%) of 2-benzyl-4-isopropyl-6-dimethylaminosaccharin as a colorless solid.

The 2-benzylsaccharin (0.32 g, 0.9 mmol) in methanol (20 mi) was treated with ammonium formate (0.24 g, 3.8 mmol) and 10% Pd on Carbon (0.25 g) and refluxed for 1 hr, cooled to room temperature and filtered through a pad of super cel, eluting with methanol (100 mi). The combined eluents were concentrated in vacuo. The residue was dissolved in MDC (10 mi), glacial acetic acid (0.25 mi) was added, stirred for 5 min. and evaporated to dryness in vacuo to give 0.25 g (100%) of 4-isopropyl-6-dimethylamino-saccharin as a colorless foam.

Following a procedure similar to that described in Preparation 1, a mixture of 4-isopropyl-6-dimethylaminosaccharin (0.27 g, 1.0 mmol), chloromethyl phenylsulfide (0.32 g, 2.0 mmol) and tetrabutyl ammonium bromide (0.1 g, 0.2 mmol) in toluene was converted to 0.22 g (56%) of 2-phenylthiomethyl-4-isopropyl-6-dimethylamino-saccharin which was treated with sulfuryl chloride (1.86 mL of 0.31 M solution, 0.6 mmol) to give 0.15 g of a yellow gum that contained 25% (by NMR) of 2-chloromethyl-4-isopropyl-6dimethylamino-7-chloro saccharin.

Preparation 28A

Thirty-one grams of 4-isopropyl-1,2-dimethoxybenzene was treated with N-bromosuccinimide followed by butyllithium and diethyl carbamyl chloride as in preparation 6B 5to yield 15.2 g of 2-isopropyl-4,5-dimethoxy-N,N-diethylbenzamide as a viscous oil. The benzamide was treated according to preparation 18B with butyllithium and sulfur dioxide followed by sulfuryl chloride then ammonia to provide 4.5 g of the sulfonamide, mp 181-1820 from ether. This was cyclized in acetic acid as in preparation 18B to obtain 2.86 g of 6,7-dimethoxy-4-isopropylsaccharin, mp 210°–212° from ethyl acetate-hexane.

To a solution of 0.5 g of 4-isopropyl-6,7-dimethoxysaccharin in 3 mL of DMF was added 0.5 mL of diisopropylethylamine at room temperature. After 15 min, 0.35 g chloromethyl phenyl sulfide was added and the mixture heated at 80° for 16 hrs. The reaction mixture was poured into EtOAc and washed with aqueous Na$_2$CO$_3$ solution, aqueous 2N HCl solution, saturated aqueous NaCl solution. The organic layer was dried over Na$_2$SO$_4$ and the solvents removed. Chromatography with MDC gave 0.35 g of desired product, which was used immediately. Treatment of the 0.35 g sample of phenylthiomethyl saccharin in 3 mL of MDC with 0.1 mL of sulfuryl chloride for 30 min at 20° followed by removal of solvents and trituration with hexane gave 0.3 g of 2-chloromethyl-6,7-dimethoxy-4-isopropylsaccharin.

Preparation 28B

To a solution of 5.7 g of methyl piperonylate in 20 mL of dry ether was added 30 mL of 3.0 methyl magnesium bromide in ether at 0° over 20 min, The mixture was stirred for 20 hrs then diluted with 200 mL of ether and washed with water. The organic layer was dried with Na$_2$SO$_4$ and the solvents removed to yield 5.6 g of crude 3,4-dimethoxy-(1'-hydroxy-1'-methylethyl)benzene. This material was immediately treated in 50 mL of acetic acid with 1 g of 10% Pd/C under 50 psi of hydrogen for 20 hrs. Filtration to remove catalyst and removal of solvent yielded 4.5 g of 5-isopropyl-1,3-benzodioxole. The isopropyldioxole was brominated, amidated, sulfonated and cyclized as in 28A to yield 700 mg of 4-isopropyl-6,7-methylenedioxysaccharin, mp 226°–228° from ethyl acetate/hexane. Five hundred milligrams of the saccharin was chloromethylated as in 28A to provide 300 mg of 2-chloromethyl-4-isopropyl-6,7-methylenedioxysaccharin, mp 174°–176°.

Other 4-R$^4$-R$^5$-saccharins of formula II useful as intermediates for the preparation of the compounds of formula I can be prepared as follows.

Reaction of 2-trifluoromethylbenzoic acid with thionyl chloride affords 2-trifluoromethylbenzoyl chloride, which, on reaction with diethylamine, affords 2-trifluoromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 2-trifluoromethyl-6-aminosulfonyl-N,N-diethylbenzamide, which, on heating in glacial acetic acid, affords 4-trifluoromethylsaccharin.

Similarly, reaction of 2-trichloromethylbenzoicacid with thionyl chloride affords 2-trichloromethylbenzoylchloride, which, on reaction with diethylamine, affords 2-trichloromethyl-N,N-diethylbenzamide. Following a procedure similar to that described in Preparation 5, reaction of the latter with s-butyl lithium and reaction of the resulting lithium salt with sulfur dioxide followed by sodium hydroxyl-amine-O-sulfonate affords 2-trichloromethyl-6-aminosulfonyl-N,N-diethylbenzamide, which, on heating in glacial acetic acid, affords 4-trichloromethylsaccharin.

Reaction of 4-cyclohexylbenzoic acid with thionylchloride affords 4-cyclohexylbenzoyl chloride, which, on reaction with diethylamine, affords 4-cyclohexyl-N,N-diethyl-benzamide. Following a procedure similar to that described in Preparation 5, reaction of the latter with s-butyl lithium and reaction of the resulting lithium salt with sulfur dioxide followed by sodium hydroxylamine-O-sulfonate affords 4-cyclohexyl-2-aminosulfonyl-N,N-diethylbenzamide, which, on heating in glacial acetic acid, affords 6-cyclohexyl saccharin.

Reaction of a 2-benzyl-6-aminosaccharin with methanesulfonyl chloride, trifluoromethylsulfonyl chloride or trichloro-methylsulfonyl chloride in MDC in the presence of pyridine followed by transfer hydrogenolysis of the 2-benzyl protecting group, affords, respectively, 6-methylsulfonylaminosaccharin, 6-trifluoromethylsulfonylaminosaccharin or 6-trichloromethyl-sulfonylaminosaccharin.

Diazotization of 6-aminosaccharin with nitrous acid in an acid medium and decomposition of the resulting diazonium salt in the presence of cupric cyanide or cupric chloride and sulfur dioxide, or cupric chloride and an alkali metal salt of methyl mercaptan or trifluoromethyl mercaptan affords, respectively, 6-cyanosaccharin, 6-chlorosulfonylsaccharin, 6-methylthiosaccharin or 6-trifluoromethylthiosaccharin. Reaction of the 6-chloro-sulfonylsaccharin in situ with ammonia or methanesulfonyl-amide affords, respectively, 6-aminoslilfonylsaccharin and 6-methanesulfonylaminosulfonylsaccharin. Oxidation of 6-methylthiosaccharin and 6-trifluoromethylthiosaccharin with two molar equivalents of 3-chloroperbenzoic acid affords 6-methylsulfonylsaccharin and 6-trifluoromethylsulfonylsaccharin, respectively.

Hydrolysis of 6-cyanosaccharin by heating with aqueous sodium hydroxide affords saccharin-6-carboxylic acid. Reaction of 6-cyanosaccharin by heating with a catalytic amount of sulfuric acid in ethanol solution affords ethyl saccharin-6-carboxylate, which, on reduction with lithium borohydride, affords 6-hydroxymethylsaccharin. Oxidation of the latter with pyridine:-chromium trioxide (2:1) complex (Collins reagent) in MDC affords 6-formylsaccharin, which, on reductive amination with ammonia and sodium cyanoborohydride, affords 6-aminomethylsaccharin.

Reaction of 4-trifluoromethylbenzoic acid with thionyl chloride affords 4-trifluoromethylbenzoyl chloride, which, on reaction with diethylamine, affords 4-trifluoromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 4-trifluoromethyl-2-aminosulfonyl-N,N-diethylbenzamide, which on heating in glacial acetic acid, affords 6-trifluoromethylsaccharin.

Reaction of 4-trichloromethylbenzoic acid with thionyl chloride affords 4-trichloromethylbenzoyl chloride, which, on reaction with diethylamine, affords 4-trichloromethyl-N,N-diethylbenzamide. Following a procedure similar to that described in Preparation 5, reaction of the latter with s-butyl lithium and reaction of the resulting lithium salt with sulfur dioxide followed by sodium hydroxylamine-O-sulfonate affords 4-trichloromethyl-2-aminosulfonyl-N,N-diethylbenzamide, which on heating in glacial acetic acid, affords 6-trichloromethylsaccharin.

Reaction of 2-ethenylbenzoic acid with thionyl chloride affords 2-ethenylbenzoyl chloride, which on reaction with diethylamine, affords 2-ethenyl-N,Ndiethylbenzamide. Reaction of the latter with s-butyl lithium and reaction of the resulting lithium salt with sulfur dioxide followed by sodium hydroxylamine-O-sulfonate affords 2-ethenyl-6-aminosulfonyl-N,N-diethylbenzamide, which, on heating in glacial acetic acid, affords 4-ethenylsaccharin.

Reaction of 2-ethenyl-6-aminosulfonyl-N,N-diethylbenzamide with bromine affords 2-(1,2-dibromoethyl)-6-aminosulfonyl-N,N-diethylbenzamide which, on reaction with sodium amide in ammonia affords 2-ethynyl-6-aminosulfonyl-N,N-diethylbenzamide, which, on heating in glacial acetic acid, affords 4-ethynylsaccharin.

Reaction of ethyl 2-aminobenzoate with two molar equivalents of benzyl chloride in acetone in the presence of potassium carbonate affords ethyl 2-(N,N-dibenzylamino)benzoate which, on saponification in aqueous ethanolic potassium hydroxide and isolation of the product from a neutral medium, affords 2-(N,N-dibenzylamino)benzoic acid, Reaction of the latter with thionyl chloride affords 2-(N,N-dibenzylamino)benzoyl chloride, which, on reaction with diethylamine, affords 2-(N,N-dibenzylamino)N,N-diethyl-benzamide. Reaction of the latter with s-butyl lithium and reaction of the resulting lithium salt with sulfur dioxide followed by sodium hydroxylamine-O-sulfonate affords 2-(N,N-dibenzyl)-6-aminosulfonyl-N,N-diethyl-benzamide, which, on heating in glacial acetic acid, affords 4-(N,N-dibenzylamino)saccharin which, on catalytic debenzylation with hydrogen over palladium-on-charcoal, affords 4-aminosaccharin. Reductive alkylation of the latter with one molar equivalent of formaldehyde in formic acid affords 4-methylaminosaccharin.

Reaction of 4-isopropyl-6-hydroxysaccharin (Preparation 19) with N,N-diethylthiocarbamyl chloride in DMF using the procedure described above in Preparation 12 affords 4-isopropyl-6-(N,N-diethylthiocarbamyloxy)saccharin which, on heating, rearranges to 4-isopropyl-6-(N,N-diethylcarbamyl-thio)saccharin.

The latter, on hydrolysis with alkali, affords 4-isopropyl-6-mercaptosaccharin which, after benzylation, reaction with methyl iodide, and transfer hydrogenolysis affords 4-isopropyl-6-methylthiosaccharin. Oxidation of the latter with one or two molar equivalents of 3-chloroperbenzoic acid affords 4-isopropyl-6-methylsulfinylsaccharin and 4-isopropyl-6-methylsulfonylsaccharin.

Reaction of 2-isopropyl-4-fluorobenzoic acid with thionyl chloride affords 2-isopropyl-4-fluorobenzoylchloride, which, on reaction with diethylamine, affords 2-isopropyl- 4-fluoro-N,N-diethylbenzamide. Reaction of the latter with s-butyl lithium and reaction of the resulting lithium salt with sulfur dioxide followed by sodium hydroxylamine-O-sulfonate affords 2-isopropyl-4-fluoro-6-aminosulfonyl-N,N-diethylbenzamide, which, on heating in glacial acetic acid, affords 4-isopropyl-6-fluorosaccharin.

Reaction of the latter with thiophenol, 4-methylphenylthiophenol, 4-methoxyphenylthiophenol, 4-chlorophenylthiophenol, 1-mercapto-4-methylnaphthalene or 1-mercaptonaphthalene by heating the reactants in DMF affords, respectively, 4-isopropyl-6-phenylthiosaccharin, 4-isopropyl-6-(4-methylphenylthio)saccharin, 4-isopropyl-6-(4-methoxyphenylthio)saccharin, 4-isopropyl-6-(4-chloro-phenylthio)saccharin, 4-isopropyl-6-(4-methyl-1-naphthylthio)saccharin, 4-isopropyl-6-(4-methyl-1-naphthylthio)saccharin and 4-isopropyl-6-(1-naphthylthio)saccharin. Oxidation of the latter with one or two molar equivalents of 3-chloroperbenzoic acid affords 4-isopropyl-6-phenylsulfinylsaccharin, 4-isopropyl-6-pehnylsulfonylsaccharin, 4-isopropyl-6-(4-methylphenylsulfinyl)saccharin, 4-isopropyl-6-(4- methylphenylsufonyl)saccharin, 4-isopropyl-6-(4-methoxyphenylsulfinyl)saccharin, 4-isopropyl-6-(4-methoxyphenylsulfonyl)saccharin, 4-iso-propyl-6-(4-chlorophenylsulfinyl)saccharin, 4-isopropyl-6-(4-chlorophenylsulfonyl)saccharin, 4-isopropyl-6-(4-methyl-1-naphthylsulfinyl)saccharin, 4-isopropyl-6-(4-methyl-1-naphthylsulfonyl)saccharin, 4-isopropyl-6-(1naphthylsulfinyl)saccharin and 4-isopropyl-6-(1-naphthylsulfonyl)saccharin.

Reaction of 4-isopropyl-6-hydroxysaccharin (Preparation 19) with one molar equivalent of acetic anhydride, benzoyl chloride or 1-naphthyl carboxylic acid chloride affords, respectively, 4-isopropyl-6-acetoxysaccharin, 4-isopropyl-6-benzoyloxysaccharin and 4-isopropyl-6-(1-naphthylcarbonyloxy)saccharin.

Heating 4-isopropyl-6-fluorosaccharin in DMF with azetidine, pyrrolidine, piperidine, morpholine, 1-benzylpiperazine, 1-methylpiperazine, imidazole, t-butyl alphaamino-acetate or ammonia affords, respectively, 4-isopropyl6(1-azetidinyl)saccharin, 4-isopropyl-6-(1-pyrrolidinyl)saccharin, 4-isopropyl-6-(1-piperidinyl)-saccharin, 4-isopropyl-6-(4-morpholinyl)saccharin, 4-isopropyl-6-(4-benzyl-1-piperazinyl)saccharin, 4-isopropyl-6-(4-methyl-1-piperazinyl)saccharin, 4-isopropyl-6-(1-1H-imidazolyl)-saccharin, 4-isopropyl-6-(carbo-t-butoxymethylamino)saccharin and 4-isopropyl-6-aminosaccharin.

Catalytic debenzylation of 4-isopropyl-6-(4-benzyl-1-piperazinyl)saccharin with hydrogen over palladium on charcoal affords 4-isopropyl-6-(1-piperazinyl)saccharin.

Hydrolysis of 4-isopropyl-6-(carbo-t-butoxycarbonylmethylamino)saccharin with dilute hydrochloric acid and isolation of the product from a neutral medium affords 4-isopropyl-6-carboxymethylaminosaccharin.

Reaction of 4-isopropyl-6-aminosaccharin with one molar equivalent of acetyl chloride affords 4-isopropyl-6-acetylaminosaccharin.

Saponification of 4-carbomethoxysaccharin (Preparation 9D) to the corresponding saccharin-4-carboxylic acid by alkaline hydrolysis, conversion of the acid to the corresponding acid chloride by reaction of the acid with thionyl chloride and reaction of the acid chloride with ammonia affords saccharin-4-carboxamide.

Reaction of each of the 4-$R^4$-$R^5$-saccharins sopreperated with paraformaldehyde and chlorotrimethylsilane in the presence of stannic chloride in ethylene dichloride affords the 4-$R^4$-$R^5$-2-chloro-methylsaccharins of formula IV listed in TABLE B where, in each instance, X is Cl.

TABLE B

| Preparation | $R^4$ | $R^5$ |
|---|---|---|
| 19A | CF$_3$ | H |
| 19B | CCl$_3$ | H |
| 19C | H | 6-cyclohexyl |
| 19D | H | 6-CH$_3$SO$_2$NH |
| 19E | H | 6-CF$_3$SO$_2$NH |
| 19F | H | 6-CCl$_3$SO$_2$NH |
| 19G | H | 6-CN |
| 19H | H | 6-NH$_2$SO$_2$ |
| 19I | H | 6-CH$_3$SO$_2$NHSO$_2$ |
| 19J | H | 6-CH$_3$SO$_2$ |
| 19K | H | 6-CF$_3$SO$_2$ |
| 19L | H | 6-HOOC |
| 19M | H | 6-HOCH$_2$ |
| 19N | H | 6-OHC |
| 19-O | H | 6-NH$_2$CH$_2$ |
| 19P | H | 6-CF$_3$ |
| 19Q | H | 6-CCl$_3$ |
| 19R | CH=CH$_2$ | H |
| 19S | C≡CH | H |

TABLE B-continued

| Preparation | $R^4$ | $R^5$ |
|---|---|---|
| 19T | NH$_2$ | H |
| 19U | CH$_3$NH | H |
| 19V | (CH$_3$)$_2$N | H |
| 19W | CH(CH$_3$)$_2$ | 6-CH$_3$S |
| 19X | CH(CH$_3$)$_2$ | 6-CH$_3$SO |
| 19Y | CH(CH$_3$)$_2$ | 6-CH$_3$SO$_2$ |
| 19Z | CH(CH$_3$)$_2$ | 6-F |
| 19AA | CH(CH$_3$)$_2$ | 6-C$_6$H$_5$S |
| 19AB | CH(CH$_3$)$_2$ | 6-(4-CH$_3$C$_6$H$_4$S) |
| 19AC | CH(CH$_3$)$_2$ | 6-(4-CH$_3$OC$_6$H$_4$S) |
| 19AD | CH(CH$_3$)$_2$ | 6-(4-ClC$_6$H$_4$S) |
| 19AE | CH(CH$_3$)$_2$ | 6-(4-CH$_3$-1-naphthyl-S) |
| 19AF | CH(CH$_3$)$_2$ | 6-(1-naphthyl-S) |
| 19AG | CH(CH$_3$)$_2$ | 6-C$_6$H$_5$SO |
| 19AH | CH(CH$_3$)$_2$ | 6-C$_6$H$_5$SO$_2$ |
| 19AI | CH(CH$_3$)$_2$ | 6-(4-CH$_3$C$_6$H$_4$SO) |
| 19AJ | CH(CH$_3$)$_2$ | 6-(4-CH$_3$C$_6$H$_4$SO$_2$) |
| 19AK | CH(CH$_3$)$_2$ | 6-(4-CH$_3$OC$_6$H$_4$SO) |
| 19AL | CH(CH$_3$)$_2$ | 6-(4-CH$_3$OC$_6$H$_4$SO$_2$) |
| 19AM | CH(CH$_3$)$_2$ | 6-(4-ClC$_6$H$_4$SO) |
| 19AN | CH(CH$_3$)$_2$ | 6-(4-ClC$_6$H$_4$SO$_2$) |
| 19AO | CH(CH$_3$)$_2$ | 6-(4-CH$_3$-1-naphthyl-SO) |
| 19AP | CH(CH$_3$)$_2$ | 6-(4-CH$_3$-1-naphthyl-SO$_2$) |
| 19AQ | CH(CH$_3$)$_2$ | 6-(1-naphthyl-SO) |
| 19AR | CH(CH$_3$)$_2$ | 6-(1-naphthyl-SO$_2$) |
| 19AS | CH(CH$_3$)$_2$ | 6-CH$_3$COO |
| 19AT | CH(CH$_3$)$_2$ | 6-C$_6$H$_5$COO |
| 19AU | CH(CH$_3$)$_2$ | 6-(1-naphthyl-COO) |
| 19AV | CH(CH$_3$)$_2$ | 6-(1-azetidinyl) |
| 19AW | CH(CH$_3$)$_2$ | 6-(1-pyrrolidinyl) |
| 19AX | CH(CH$_3$)$_2$ | 6-(1-piperidinyl) |
| 19AY | CH(CH$_3$)$_2$ | 6-(4-morpholinyl) |
| 19AZ | CH(CH$_3$)$_2$ | 6-(4-benzyl-1-piperazinyl) |
| 19BA | CH(CH$_3$)$_2$ | 6-(4-methyl-1-piperazinyl) |
| 19BB | CH(CH$_3$)$_2$ | 6-(1-1H-imidazolyl) |
| 19BC | CH(CH$_3$)$_2$ | 6-(NHCH$_2$COOC$_4$H$_9$-t) |
| 19BD | CH(CH$_3$)$_2$ | 6-NH$_2$ |
| 19BE | CH(CH$_3$)$_2$ | 6-(1-piperazinyl) |
| 19BF | CH(CH$_3$)$_2$ | 6-(NHCH$_2$COOH) |
| 19BG | CH(CH$_3$)$_2$ | 6-(CH$_3$CONH) |
| 19BH | CONH$_2$ | H |

Preparation 19BI

Reaction of isothiazole-5-carboxaldehyde with lithium 3-(triphenylphosphoranylidene)propanoate under standard Wittig conditions provides 4-(5-isothiazolyl)-3-butenoic acid which is reduced and cyclized with aluminum chloride to provide 4-oxo-4,5,6,7-tetrahydrobenzisothiazole. The 4-oxo compound is reacted with methylenetriphenyl phosphorane under standard Wittig conditions and a methylene is inserted into the resulting 4-methylene compound via a Simmons Smith reaction to provide 6,7dihydrospiro[benzisothiazol-4(5H),1'-cyclopropane] which is oxidized with hydrogen peroxide in acetic acid to give 6,7-dihydrospiro[-benzisothiazol-4(5H), 1'-cyclopropane 1,1-dioxide (4-spiro-cyclopropyl tetrahydrosaccharin). This is chloromethylated according to the procedure of Preparation 1A to give 2-chloromethyl-4-spirocyclopropyl-4,5,6,7-tetrahydrosaccharin.

Preparation 19BJ

2-Benzyl-4-isopropyl-6-oxo-tetrahydrosaccharin of preparation 23 is reduced with sodium borohydride and methylated with methyl iodide in the presence of sodium hydride to provide 2-benzyl-4-isopropyl-6-methoxy-tetrahydrosaccharin. This is debenzylated and chloromethylated as in preparation 23 to provide 2-chloromethyl-4-isopropyl-6-methoxy-4,5,6,7-tetrahydrosaccharin.

Preparation 20A

A mixture of 10.0 g (0.063 mol) of 2,6-difluorobenzoic acid and 66.0 g (0.57 mol) of chlorosulfonic acid was heated at 155°-160° C. and then poured carefully into 100 ml of ice water. The solids which separated were collected by filtration, air dried and recrystallized from chloroform to give 7.0 g of 3-chlorosulfonyl-2,6-difluorobenzoic acid, 0.64 g (0.0025 mol) of which was dissolved in MDC and treated at −10° C. with a solution of 0.25 g (0.0025 mol) of 1-methyl-piperazine and 0.33 g (0.0026 mol) of diisopropylethylamine. The product which separated was collected by filtration, washed with MDC and dried to give 0.4 g (50%) of 2,6-difluoro-3-(4-methyl-1-piperazinyl)sulfonylbenzoic acid.

Preparations 20B-20G

Following a procedure similar to that described in Preparation 20A above, 3-chlorosulfonyl-2,6-dichlorobenzoic acid, m.p. 172°-175° C. (from chloroform) was prepared in 56% yield by heating a mixture of 2,6-dichlorobenzoic acid with chlorosulfonic acid at 150°-160° C.

Reaction of the latter with an appropriate amine (N=B) afforded the 3-aminosulfonyl-2,6-dichlorobenzoic acids listed in TABLE C below. In each instance products were not further purified but were used as such in the next step.

TABLE C

| Preparation | N=B | Yield |
|---|---|---|
| 20B | 4-morpholinyl | 86 |
| 20C | NHCH$_2$COO—C$_4$H$_9$-(t) | 36 |
| 20D | 4-CH$_3$-1-piperazinyl | 40 |
| 20E | 4-C$_6$H$_5$CH$_2$-1-piperazinyl | 59 |
| 20F | N(CH$_3$)CH$_2$CH$_2$N(CH$_3$)$_2$ | 82 |
| 20G | NHCH$_2$COOBzl | 50 |

To a mixture of 1.0 g (0.003 mol) of benzyl 2,6-dichloro-3-hydroxybenzoate and 0.18 g of 60% dispersion of sodium hydride in mineral oil in 30 ml of DMF was added a solution of 0.008 mol of 4-(2-chloroethyl)-morpholine in 20 ml of t-butyl methyl ether and the mixture heated at 70° C. for three hours. The reaction mixture was then taken to dryness and the residue taken up in ethyl acetate and the organic solution washed with water and brine, then dried and concentrated in vacuo to dryness to give 1.25 g (83%) of benzyl 2,6-dichloro-3-[2-(4-morpholinyl)ethoxy]benzoate which was dissolved in 1:1 ethyl acetate:methanol (50 ml) and reduced with hydrogen over 0.25 g of 10% palladium-oncharcoal. When reduction was complete, the catalyst was removed by filtration, washed with DMF and the combined filtrates taken to dryness in vacuo to give 0.75 g (75%) of 2,6-dichloro-3-[2-(4-morpholinyl)ethoxy]-benzoic acid.

Preparation 21B

Following a procedure similar to that described in Preparation 21A, 1.0 q (0.003 mol) of benzyl 2,6-dichloro-3-hydroxybenzoate was reacted with 0.092 mol of N-(2-chloroethyl)-N,N-dimethylamine in 30 ml of DMF and 20 ml of t-butyl methyl ether in the presence of 0.18 g of a 60% mineral oil dispersion of sodium hydride to give a quantitative yield of benzyl 2,6-dichloro-3-[2-(dimethylamino)ethoxy]benzoate which was reduced catalytically in a 5:2 solution of ethyl acetate:methanol over 0.2 g of 10% palladium-on-charcoal. There was thus obtained 0.2 g (22%) of 2,6-dichloro-3-[2-(dimethylamino)ethoxy]benzoic acid.

Preparation 21C

To a solution of methyl 2,6-dichloro-4-methoxybenzoate (J. Org. Chem., 50, 408 1985) (5.5 g, 0.023 mol) in methanol (50 ml) was added 5N sodium hydroxide (20 mL). The resulting mixture was heated at reflux for 20 hr, cooled to room temperature, concentrated in vacuo and acidified to pH 1 with 2N HCl. The separated solids were collected by filtration to give 5.2 g (100%) of 2.6-dichloro-4-methoxybenzoic acid, which was treated with 60 mL of a 1M solution of boron tribromide (0.06 mol) in dichloroethane (100 ml) at reflux for 2 hr. The resulting mixture was cooled to room temperature and poured onto water/reethanol (50 mL of a 9:1 mixture). After stirring for 10 minutes, the mixture was extracted with ether (400 mL) and the organic phase washed with water, brine and dried. Removal of the solvent in vacuo gave 4.0 g (80%) of 2,6-dichloro-4-hydroxyhenzoic acid.

The latter (1.05 g, 0.005 mol) was dissolved in 595% ethanol (25 ml) and treated with benzyl chloride (0.71 g, 0.006 mol) and 1N NAOH (5 ml). After refluxing under nitrogen for 2 hr, the reaction mixture was cooled to room temperature and concentrated in vacuo. The residue was acidified with 2N HCl and extracted with ether. The organic phase was washed with saturated NaHCO$_3$, water and 10% NAOH. After discarding the organic phase, the NAOH washings were acidified with 2N HCl and reextracted with ether (2×50 mL). The ether extract was then dried and concentrated in vacuo to give 0.63 g (42%) of benzyl-2,6-dichloro-4-hydroxybenzoate.

Following a procedure similar to that described in Preparation 21A, 630 mg of benzyl 2,6-dichloro-4-hydroxybenzoate was converted to 350 mg of 2,6-dichloro-4[2-(4-morpholinyl)ethoxy]benzoic acid.

Preparation 24A

A solution of 1.9 g (0.01 mol) of 2,6-dichloro-3-hydroxybenzaldehyde in 10 mL dry DMF was flushed with nitrogen and 0.3 g of 97% sodium hydride was added with magnetic stirring. Hydrogen was evolved giving a clear red-brown solution. To this was added a solution of 2-dimethylaminoethylchloride (from 2.0 g of the hydrochloride) in 6 mL of t-butylmethyl ether. The solution was heated to reflux for ½ hr. Sodium chloride precipitated. The condenser was removed and heating was continued for ½ hr. The reaction mixture was concentrated to dryness, taken up in dilute HCl and extracted with methylene chloride. The aqueous layer was basified with 10% Na$_2$CO$_3$ solution, extracted 3× with CH$_2$Cl$_2$ and the extracts evaporated to a brown oil which was distilled in a Kugelrohr, bp 155°-160°/0.12 mm. The yellow distillate crystallized and was converted to the hydrochloride with ethereal HCl. Recrystallization from CH$_3$CN gave 661 mg of 2,6-dichloro-3-[2-dimethylamino)ethoxy]benzaldehyde hydrochloride, mp 177°-178°.

Freshly prepared silver oxide (from 1.7 g AgNO$_3$) was suspended in 1.0 mL of 10% sodium hydroxide solution which was then heated to 55°. The aldehyde (2.62 g, 0.01 mm) was added with magnetic stirring. The exothermic reaction raised the temperature to 65° and silver precipitated. Heating was continued at 60° for ¼ hr. The reaction was filtered and the filtrate extracted 2× with CH$_2$Cl$_2$. Evaporation of the CH$_2$Cl$_2$ gave 0.804 g of starting aldehyde. The aqueous phase was acidified with 3N HCl and evaporated in vacuo to a white solid which was recrystallized from 10 mL of water. There was obtained 1.065 g (34%) of 2,6-dichloro-3-[2-(dimethylamino)ethoxy]benzoic acid, mp 234°–236°.

Preparations 24B–24D

Following a procedure similar to that described in Preparation 24A above, the aldehydes and acids shown in Table D were prepared:

TABLE D

| Preparation | N=B | bp | yield | Acid HCl Salt mp | yield |
|---|---|---|---|---|---|
| 24B | 2-(1-pyrrolidinyl)-ethoxy | 130–140/0.1 mm | 41 | 253–255 | 10 |
| 24C | 2-(1-piperdinyl) ethoxy | 160–180/0.1 mm | 54 | 241–242 | 24 |
| 24D | 2-(diethylamino) ethoxy | not distilled | — | 220–222 | 15 |

Preparation 25

To a solution of chlorine (15.7 g, 0.22 mol) in glacial acetic acid (250 ml) at 0° C. was added methyl 3-hydroxybenzoate (15.2g, 0.1 mol). The resulting solution was warmed to room temperature and stirred for 1 hr and evaporated to dryness in vacuo to give 21.4 g of a yellow oil which was found to contain 75% of methyl 2,6-dichloro-3-hydroxybenzoate by NMR. The oil (21.4 g) was dissolved in acetone (600 mL), benzyl bromide 19.9 g, 0.12 mol) and potassium carbonate (22.7 g, 0.16 mol) were added and refluxed under nitrogen for 16 hr. The reaction mixture was cooled to room temperature and the solids filtered off. The filtrate was concentrated in vacuo and the residue taken up in 10% ethyl acetate in hexanes (100 mL) and chilled in an ice bath. The solids that emerged were collected by filtration and air dried to give 14.3 g (47%) of methyl 2,6-dichloro-3-benzyloxybenzoate.

A solution of methyl 2,6-dichloro-3-benzyloxybenzoate (2.1 g, 6.7 mmol) and 10% aqueous NAOH (25 mL) in methanol (25 mL) was refluxed under nitrogen for 24 hr and cooled to room temperature. The resulting mixture was concentrated to one-half the volume in vacuo and acidified to pH 1 with 2N HCl. the solids that precipitated were collected by filtration, washed with water, hexanes and air dried to give 2.0 g (100%) of 2,6-dichloro-3-benzyloxybenzoic acid as a white solid.

Preparation 26

A solution of 5 g of 2,6-dimethoxy-3-nitrobenzoic acid in THF was hydrogenated in the presence of 10% Pd on C and the resulting amine was acetylated in situ with acetic anhydride and pyridine to provide 0.9 g of 3-acetylamino-2,6-dimethoxybenzoic acid.

Preparation 27

To a suspension of 3.6 g (0.12 mol) of paraformaldehyde in 50 mL of 1,2-dichloroethane and 30 mL (26 g, 0.24 mol) of trimethylsilyl chloride under nitrogen was added 0.2 mL of stannic chloride and the resulting solution was stirred on a steam bath. After 30 min, 9.55 g (0.05 mol) of 2,6-dichlorobenzoic acid was added and the reaction heated for an additional 20 hours. Volatiles were removed, the residue dissolved in MDC and washed with NaHCO$_3$, dried and stripped to an oil which was triturated in hexane and filtered to obtain 8.5 g of chloromethyl-2,6-dichlorobenzoate.

Preparation of the Final Products

EXAMPLE 1A

A mixture of 0.5 g (0.0017 mol) of 2-chloromethyl-4,6-dimethoxysaccharin, 0.33 g (0.0017 mol) of 2,6-dichlorobenzoic acid and 17 g (0.25 ml, 0.0017 mol) of triethylamine in 15 ml of toluene was heated under reflux for about six hours, then cooled and concentrated to dryness in vacuo. The residue was chromatographed on silica gel, eluting with 40% ethyl acetate/hexane to give 0.44 g (53%) of 4,6-dimethoxy-2-saccharinylmethyl 2,6-dichlorobenzoate, m.p. 200°–201° C.

Following a procedure similar to that described in Example 1A above, the compounds of formula I listed in TABLE 1 below were similarly prepared. The reactions were carried out either in the presence of cesium carbonate, potassium carbonate, triethylamine (TEA), diisopropylethylamine (DIPEA), or 1,8-diazabicyclo-[5.4.0]undec-7-ene (DBU) as basic catalyst or by use of the cesium or thallium salt of the benzoic acid and optionally in the presence of tetrabutylammonium bromide (TBAB) in an appropriate organic solvent as indicated in the column headed "Solv./Cat". NMP is N-methylpyrrolidinone. In each of Examples 1D-1I, IN, IAI and 1AJ-1AN the products were prepared from the 4-R$^4$-R$^5$-2-bromomethylsaccharin. In all other examples the appropriate 4-R$^4$-R$^5$-2-chloromethylsaccharin was used as the starting material. Here and elsewhere in this specification various heterocyclic or other groups are abbreviated as follows:

| Ac | acetyl |
| Mor | morpholinyl |
| pip | piperazinyl |
| Bzl | benzyl |
| azet | azetidinyl |
| imidazol | imidazolyl |
| pyr | pyrrolidinyl |
| pid | piperidinyl |

TABLE 1

| Ex | R$^4$/R$^5$ | Ar | Solv/Cat | m.p./Solv | Yield |
|---|---|---|---|---|---|
| 1B | CH(CH$_3$)$_2$<br>6-CH$_3$O | 2,6-Cl$_2$C$_6$H$_3$ | DMF<br>K$_2$CO$_3$/TBAB | Foam | 77 |
| 1C | CH(CH$_3$)$_2$<br>6-HO | 2,6-Cl$_2$C$_6$H$_3$ | DMF<br>Cs$_2$CO$_3$ | 130–131 | 67 |
| 1D | H<br>H | 2,6-(CH$_3$O)$_2$C$_6$H$_3$ | acetone<br>K$_2$CO$_3$ | 155–156<br>i-PrOAc | 26 |
| 1E | H<br>H | 2,4-(CH$_3$O)$_2$C$_6$H$_3$ | CH$_3$CN<br>DBU | 147–148<br>CH$_3$CN | 67 |
| 1F | H<br>H | 1-naphthyl | xylene<br>TEA | 161–163<br>CH$_3$CN | 55 |
| 1G | H<br>H | 2-Cl-6-AcNHC$_6$H$_3$ | xylene<br>TEA | 164–165<br>CH$_3$CN | 49 |

TABLE 1-continued

| Ex | $R^4/R^5$ | Ar | Solv/Cat | m.p./Solv | Yield |
|---|---|---|---|---|---|
| 1H | H<br>H | 2,6-$Br_2C_6H_3$ | xylene<br>TEA | 196–197<br>$CH_3CN$ | 56 |
| 1I | $CH(CH_3)_2$<br>H | 1-naphthyl | xylene<br>TEA | 146–148<br>$CH_3CN$ | 56 |
| 1J | H<br>H | 2,6-$F_2C_6H_3$ | DMF<br>$Cs_2CO_3$ | 113–115 | 42 |
| 1K | $CH(CH_3)_2$<br>H | 2,6-$(CH_3)_2C_6H_3$ | DMF/$CH_3OH$<br>$Cs_2CO_3$ | 80–81 | 18 |
| 1L | $CH(CH_3)_2$<br>H | 9-anthryl | toluene<br>TEA | 184–185 | 46 |
| 1M | $CH(CH_3)_2$<br>H | 2,5-$Cl_2C_6H_3$ | DMF/$CH_3OH$<br>$Cs_2CO_3$ | 125–126 | 66 |
| 1N | H<br>H | $C_6H_5$ | DMF<br>Tl salt | 108–110<br>i-PrOH | 21 |
| 1-O | $CH_3$<br>H | 2,6-$Cl_2C_6H_3$ | DMF<br>Tl salt/TBAB | 167–168 | 87 |
| 1P | $C_2H_5$<br>H | 2,6-$Cl_2C_6H_3$ | DMF<br>Tl salt/TBAB | 113–115 | 83 |
| 1Q | $CH(CH_3)_2$<br>H | 2,6-$Cl_2C_6H_3$ | DMF<br>Tl salt/TBAB | 119–120 | 83 |
| 1R | $C_6H_5$<br>H | 2,6-$Cl_2C_6H_3$ | DMF<br>Tl salt/TBAB | 144–146 | 80 |
| 1S | H<br>H | 2,6-$Cl_2$-3-($SO_2$-Mor)$C_6H_2$ | DMF<br>Tl salt/TBAB | 148–150 | 38 |
| 1T | H<br>H | 2,6-$Cl_2$-3-($SO_2NHCH_2COOH)C_6H_2$ | acetone<br>$K_2CO_3$ | 205–207 | 54 |
| 1U | $CH(CH_3)_2$<br>H | 2,6-$Cl_2$-3-($SO_2$-4-Mor)$C_6H_2$ | acetone<br>$K_2CO_3$/TBAB | 139–141 | 81 |
| 1V | $CH(CH_3)_2$<br>H | 2,6-$Cl_2$-3-($SO_2$-4-$CH_3$-1-pip)$C_6H_2$ | DMF<br>$K_2CO_3$/TBAB | >180[b] | 94 |
| 1W | $CH(CH_3)_2$<br>H | 2,6-Cl-3-($SO_2NHCH_2COOH)C_6H_2$ | DMF<br>$K_2CO_3$/TBAB | >180[c] | 8 |
| 1X | $CH(CH_3)_2$<br>H | 3-BzlO$C_6H_4$[d] | DMF<br>$K_2CO_3$/TBAB | 65–68 | 16 |
| 1Y | $CH(CH_3)_2$<br>H | 2,6-$Cl_2$-3-BzlO$C_6H_2$[d] | DMF<br>$K_2CO_3$/TBAB | 80–83 | 12 |
| 1Z | $CH(CH_3)_2$<br>H | 2,6-$Cl_2$-3-($SO_2$-4-Bzl-1-pip)$C_6H_2$ | DMF<br>$K_2CO_3$/TBAB | 172–175[b] | 75 |
| 1AA | $CH(CH_3)_2$<br>H | 2,6-$Cl_2$-3-[$SO_2N(CH_3)CH_2CH_2N(CH_3)_2$]$C_6H_2$ | DMF<br>$K_2CO_3$/TBAB | 128–133[b] | 62 |
| 1AB | $CH(CH_3)_2$<br>H | 2,6-$Cl_2$-3-$CH_3OC_6H_2$ | DMF<br>$K_2CO_3$/TBAB | 166–168 | 46 |
| 1AC | $CH(CH_3)_2$<br>H | 2,6-$Cl_2$-4-$CH_3OC_6H_2$ | DMF<br>$K_2CO_3$/TBAB | 178–180 | 74 |
| 1AD | $CH(CH_3)_2$<br>H | 2,6-$Cl_2$-3-($OCH_2CH_2$-4-Mor)$C_6H_2$ | DMF<br>$K_2CO_3$/TBAB | 140–143[b] | 90 |
| 1AE | $CH(CH_3)_2$<br>H | 2,6-$Cl_2$-3-[$OCH_2CH_2N(CH_3)_2$]$C_6H_2$ | DMF<br>$K_2CO_3$/TBAB | 135–138[b] | 74 |
| 1AF | $CH(CH_3)_2$<br>H | 2,6-$Cl_2$-2-[$SO_2N(CH_3)(CH_2)_3N(CH_3)_2$]$C_6H_2$ | DMF<br>$K_2CO_3$/TBAB | 143–148[e] | 93 |
| 1AG | $CH(CH_3)_2$<br>H | 2,6-$F_2$-3-[$SO_2$-(4-$CH_3$-1-pip)]$C_6H_2$ | DMF<br>$K_2CO_3$/TBAB | >161[f] | 95 |
| 1AH | $CHCH_3C_2H_5$<br>H | 2,6-$Cl_2C_6H_3$ | DMF<br>$K_2CO_3$/TBAB | 110–113 | 26 |
| 1AI | H<br>H | 2,6-$Cl_2C_6H_3$ | DMF<br>Tl salt | 158–159<br>i-PrOH | 31 |
| 1AJ | H<br>H | 2,6-$F_2C_6H_3$ | EtOH<br>Tl salt | 126–127<br>i-PrOH | 28 |
| 1AK | H<br>H | 2,6-$(CH_3)_2C_6H_3$ | EtOH<br>Tl salt | 138–140<br>i-PrOH | 29 |
| 1AL | H<br>H | 2,3,6-$Cl_3C_6H_2$ | EtOH<br>Tl salt | 174–176<br>i-PrOH | 33 |
| 1AM | H<br>H | 9-anthryl | xylene<br>TEA | 208–210<br>$CH_3CN$ | 52 |
| 1AN | H<br>H | 2,6-$(CF_3)_2C_6H_3$ | DMF<br>Tl salt | 153–155 | 49 |
| 1AO | $CH(CH_3)_2$<br>H | 2,4-$Cl_2C_6H_3$ | DMF<br>$K_2CO_3$/TBAB | 130–131.5 | 62 |
| 1AP | $CH(CH_3)_2$<br>6-$CH_3O$ | 2,6-$Cl_2$-3-[$SO_2$-(4-$CH_3$-1-pip)]$C_6H_2$ | DMF<br>$K_2CO_3$/TBAB | 151[b] | 65 |
| 1AQ | $CH(CH_3)_2$<br>6-$CH_3O$ | 2,6-$Cl_2$-3-[$SO_2N(CH_3)CH_2CH_2N(CH_3)_2$] | DMF<br>$K_2CO_3$/TBAB | 145–155[b] | 23 |
| 1AR | $CH(CH_3)_2$<br>6-$CH_3O$ | 2,6-$Cl_2$-3-<br>[$SO_2N(CH_3)CH_2CH_2N(CH_3)_2$]-$C_6H_2$ | DMF<br>$K_2CO_3$/TBAB | 151[b] | 38 |
| 1AR | | | NMP<br>$K_2CO_3$ | 145–146 EtOH<br>166–167[g] EtOH | 69 |
| 1AS | $CH(CH_3)_2$<br>6-$CH_3O$ | 2,6-$Cl_2$-3-[$OCH_2CH_2N(CH_3)_2$]-$C_6H_2$ | DMF<br>$K_2CO_3$ (3 eq) | 190–191[b]<br>$CH_3CN/Et_2O$ | 31 |
| 1AT | $CH(CH_3)_2$<br>6-$CH_3O$ | 2,6-$Cl_2$-3-($OCH_2CH_2$-1-pyr)-$C_6H_2$ | DMF<br>$K_2CO_3$ (3 eq) | 165–167[b]<br>$CH_3CN/Et_2O$ | 36 |
| 1AU | $CH(CH_3)_2$ | 2,6-$Cl_2$-3-($OCH_2CH_2$-1-pid)-$C_6H_2$ | DMF | 181–184[b] | 38 |

TABLE 1-continued

| Ex | R⁴/R⁵ | Ar | Solv/Cat | m.p./Solv | Yield |
|---|---|---|---|---|---|
| 1AV | CH(CH₃)₂ 6-CH₃O | 2,6-Cl₂-3-(OCH₂CH₂NEt₂)-C₆H₂ | DMF K₂CO₃ (3 eq) | CH₃CN/Et₂O 165-167[b] | 63 |
| 1AW | CH(CH₃)₂ 6-CH₃O | 2,6-Cl₂-C₆H₃ | DMF K₂CO₃ (3 eq) Cs salt | CH₃CN/Et₂O 101-110 | 87 |
| 1AX | CH(CH₃)₂ 6-OH | 2,6-Cl₂-3-(OCH₂CH₂-4-Mor)-C₆H₂ | DMF Cs salt | amorphous | 87 |
| 1AY | C₂H₅ 6-OEt | 2,6-Cl₂C₆H₃ | DMF K₂CO₃/TBAB | 193-195 iPrOH | 71 |
| 1AZ | CH(CH₃)₂ 5,7-(CH₃O)₂ | 2,6-Cl₂-C₆H₃ | DMF K₂CO₃ | 183-185[b] EtOH/Et₂O | — |
| 1BA | n-C₃H₇ 6-(4-CH₃-1-pip) | 2,6-Cl₂-C₆H₃ | DMF K₂CO₃ | 138-140 iPrOH/hex | 79 |
| 1BB | CH(CH₃)₂ 5,6-(CH₃O)₂ | 2,6-Cl₂-C₆H₃ | DMF K₂CO₃ | 171-173 iPrOH | 75 |
| 1BC | CH(CH₃)₂ 5,6-(CH₃O)₂ | 2,6-Cl₂-C₆H₃ | DMF K₂CO₃ | 138-139 iPrOH/hex | 17 |
| 1BD | n-C₃H₇ 5,6-(CH₃O)₂ | 2,6-Cl₂-3-(OCH₂CH₂-4-Mor)-C₆H₂ | DMF K₂CO₃ | 183-185[b] iPrOH/ether | 48 |
| 1BE | CH(CH₃)₂ 6-CH₃O | 3-P(O)(OEt)₂-C₆H₄ | DMF K₂CO₃ | oil from chromatography SiO₂-EtOAc/hex | 56 |
| 1BF | CH(CH₃)₂ 6,7-(CH₃O)₂ | 2,6-Cl₂-C₆H₃ | CH₃CN DIPEA | 130-132 | 23 |
| 1BG | CH(CH₃)₂ 6,7-(—OCH₂O—) | 2,6-Cl₂-C₆H₃ | CH₃CN DIPEA | 160-162 SiO₂-MDC/Me₂CO | 61 |
| 1BH | CH(CH₃)₂ 6,7-(CH₃O)₂ | 2,6-Cl₂-3-[SO₂-(4-CH₃-1-pip)]-C₆H₂ | CH₃CN DIPEA | 176-182 ether | 67 |
| 1BI | CH(CH₃)₂ 6,7-(—OCH₂O—) | 2,6-Cl₂-3-[SO-(4-CH₃-1-pip)]-C₆H₂ | CH₃CN DIPEA | 198-200 ether/hexane | 51 |
| 1BJ | CH(CH₃)₂ 6,7-(—OCH₂O—) | 2,6-Cl₂-3(OCH₂CH₂-4-Mor)-C₆H₂ | CH₃CN DIPEA | 160-170[b] ether | 40 |
| 1BK | CH(CH₃)₂ 6-CH₃O | 2,6-(CH₃O)₂—C₆H₃ | CH₃CN DIPEA | 167-168 | 73 |
| 1BL | CH(CH₃)₂ 6-CH₃O | 2,6-F₂-C₆H₃ | CH₃CN DIPEA | 128-129 | 62 |
| 1BM | CH(CH₃)₂ 6-CH₃O | 2,6-(CH₃)₂—C₆H₃ | CH₃CN DIPEA | 157-158 | 81 |
| 1BN | CH(CH₃)₂ 6-CH₃O | 2,6-(CH₃O)₂-3-NO₂—C₆H₂ | CH₃CN DIPEA | 79-81 | 24 |
| 1BO | CH(CH₃)₂ 6-CH₃O | 2,4,6-(CH₃O)₃—C₆H₂ | CH₃CN DIPEA | 150-151 | 87 |
| 1BP | CH(CH₃)₂ 6-CH₃O | 2,6-(CH₃O)2-4-BzlO—C₆H₂ | CH₃CN DIPEA | 178-179 | 71 |
| 1BQ | CH(CH₃)₂ 6-CH₃O | 2,6-F₂-4-CH₃O—C₆H₂ | CH₃CN DIPEA | | |
| 1BR | CH(CH₃)₂ 6-CH₃O | 2,6-(CH₃O)₂-3-NHAc—C₆H₂ | CH₃CN DIPEA | 183-184 | 74 |
| 1BS | CH(CH₃)₂ 6-CH₃O | 2-CH(CH₃)₂—C₆H₄ | CH₃CN DIPEA | 144-146 | 63 |
| 1BT | CH(CH₃)₂ 6-N(CH₃)₂-7-Cl | 2,6-Cl₂—C₆H₃ | DMF TBAB/K₂CO₃ | foam | 9 |
| 1BU | CH(CH₃)₂ 6-CH₃O | 2,6-Cl₂-3-BzlO—C₆H₂ | DMF K₂CO₃ | 139-140 MDC/hex | 89 |
| 1BV | CH(CH₃)₂ 6-CH₃O | 2,6-Cl₂-3-(SO₂NHCH₂COOBzl)C₆H₂ | DMF K₂CO₃ | not crystallized | 53 |
| 1BW | CH(CH₃)₂ 6-OH | 2,6-Cl₂-3-[SO₂-(4-CH-1-pip)]C₆H₂ | DMF TBAB/K₂CO₃ | 208-211[b] | 47 |
| 1BX | C(CH₃)₃ H | 2,6-Cl₂—C₆H₃ | DMF K₂CO₃ | 162-163 MDC/ether/hex | 78 |
| 1BY | CH(CH₃)₂ H | 2,6-Cl₂-4-(OCH₂CH₂-4-Mor)C₆H₂ | DMF TBAB/K₂CO₃ | 138-140[b] | 65 |
| 1BZ | CH(CH₃)₂ 6-CH₃O | 2,6-(CH₃)₂-4-BzlO-C₆H₂ | | | |

[a]2-Chloromethylsaccharin reacted with 2,6-dichloro-3-carbo-t-butoxycarbonyl-methyl-aminosulfonylbenzoic acid and the product hydrolyzed with trifluoroacetic acid in MDC to give the corresponding 2-saccharinylmethyl carboxymethyl-amino-sulfonylbenozate in 76% yield.
[b]HCl salt.
[c]2-Chloromethyl-4-isopropylsaccharin reacted with 2,6-dichloro-3-benzyloxy-carbonylmethylaminosulfonylbenzoic acid and the product catalytically debenzylated under 1 atm. of hydrogen over palladium/charcoal in EtOAc with 17% acetic acid to give the corresponding acid in 80% yield.
[d]2-Chloromethyl-4-isopropylsaccharin reacted with 2,6-dichloro-3-benzyloxybenozoic acid, and two products were obtained, one in which the benzoic acid moiety had been dechlorinated.
[e]HCl.5/2 H₂O.
[f]HCl.3/2 H₂O.
[g]CH₃SO₃H salt.

EXAMPLE 1AW

The cesium salt of 2,6-dichlorobenzoic acid as prepared from 4.48 g (0.0235 mol) of 2,6-dichlorobenzoic acid and 3.82 g (0.0117 mol) of CsCO₃ in methanol. The salt was isolated by removing the solvent under reduced pressure and drying under high vacuum for ½ hr. The dried salt was suspended by stirring in 10-15 mL of DMF and 3.4 g (0.0117 mol) of 2-chloromethyl-6- hydroxy-4-isopropylsaccharin was added. The mixture was heated at 80° for 2-3 hr, cooled, diluted with water and extracted with 200 mL of 7:3 ether:ethyl acetate. The organic layer was washed with water and saturated NaCl and dried. The solvent was removed and the residue was purified by flash chromatography with ethyl acetate-hexane on silica gel to give 4.53 (87%) of 6-hydroxy-4-isopropyl-2-saccharinylmethyl-2,6-dichlorobenozic (no mp).

EXAMPLE 2A

A solution of 1.4 g (0.0026 mol) of 4-isopropyl-2-saccharinylmethyl 2,6-dichloro-3-benzyloxybenzoate in 50 ml of ethyl acetate was treated with 0.3 g of 10% palladium-on-charcoal and 0.5 ml of acetic acid and the mixture stirred under 1 atm. of hydrogen for sixteen hours. The catalyst was removed by filtration, and the filtrate was taken to dryness in vacuo to give 1.16 g (100%) of 4-isopropyl-2-saccharinylmethyl 2,6-dichloro-3-hydroxybenzoate, m.p. 78°-80° C.

EXAMPLE 2B

Following a procedure similar to that described in Example 2A above, 1.2 g (0.0018 mol) of 4-isopropyl-2-saccharinylmethyl 2,6-dichloro-3-(4-benzyl-1-piperazinylsulfonyl)benzoate (Example 1Z) was reduced with hydrogen in 50 ml of ethyl acetate and 2 ml of acetic acid over 0.3 g of 10% palladium-on-charcoal and the product converted to the hydrochloride salt to give 0.5 g (68%) of 4-isopropyl-2-saccharinylmethyl 2,6-dichloro-3-(1-piperazinylsulfonyl)benzoate hydrochloride, m.p. above 171° C.

EXAMPLE 2C

A mixture of 4-isopropyl-6-methoxy-2-sacchariny-lmethyl-2,6-dichloro-3-benzyloxybenzoate of Example 1BU (2.5 g, 4.4 mmol), 10% Pd on Carbon (0.7g) and glacial acetic acid (1 mL in ethyl acetate (100 mL) was stirred under 50 psi hydrogen in a Parr hydrogenator for 1.5 hr. The resulting mixture was filtered through a pad of super cel eluting with ethyl acetate (100 mL). The combined filtrate was washed with saturated NaHCO₃, water, brine and dried. Removal of the solvent in vacuo and crystallization from 1:1 ether/hexanes gave 2.1 g (100%) of 4-isolpropyl-6-methoxy-2-saccharinyl-methyl 2,6-dichloro-3-hydroxybenzoate, mp 152°-154°.

EXAMPLE 2D

By a process analogous to that of Example 2A, 0.41 g of 4-isopropyl-6-methoxy-2-saccharinylmethyl 2,6-dichloro-3-benzyloxycarbonylmethylaminosulfonyl-benzoate of Example 1BV was catalytically debenzylated under 1 atm. of hydrogen over palladium/charcoal in ethyl acetate with 20% acetic acid to give 0.16 g (45%) 4-isopropyl-6-methoxy-2-saccharinylmethyl 2,6-dichloro-3-carboxymethylaminosulfonylbenzoate, mp 204°-206°.

EXAMPLE 3A

A solution of 1.05 g (0.0024 mol) of 4-isopropyl-2-saccharinylmethyl 2,6-dichloro-3-hydroxybenzoate (Example 2A), 0.50 g (0.0026 mol) of t-butyl alpha-bromoacetate and 0.48 g (0.0035 mol) of potassium carbonate in 25 ml of acetone was heated under reflux for seven hours, then cooled to ambient temperature, filtered and the filtrate taken to dryness to give 0.32 g (24%) of 4-isopropyl-2-saccharinylmethyl 2,6-dichloro-3-t-butoxycarbonylmethoxybenzoate, which was dissolved in 10 ml of MDC containing 2 ml of trifluoroacetic acid. The solution was stirred at ambient temperature under nitrogen for two hours, taken to dryness and the residue triturated with hexane/ether. The resulting solid was collected by filtration to give 0.18 g (64%) of 4-isopropyl-2-saccharinylmethyl 2,6-dichloro-3-carboxymethoxybenzoate, m.p. 210°-212° C.

EXAMPLE 3B

A solution of 0.78 g (1.6 mmol) of 4-isopropyl-6-methoxy-2-saccharinylmethyl-2,6-dichloro-3-hydroxybenzoate, 0.38 g (2.0 mmol) of t-butyl α-bromoacetate and 0.3 g (2.1 mmol) of potassium carbonate in 50 mL acetone was heated under reflux for 16 h, then cooled to room temperature, filtered and the filtrate taken to dryness. Purification of the residue by flash chromatography on silica gel (4:2 hexanes:ethyl acetate) gave 0.65 g (67%) of 4-isopropyl-6-methoxy-2-saccharinylmethyl 2,6-dichloro-3-t-butoxycarbonylmethoxybenzoate. The t-butyl ester (0.55 g, 0.9 mmol) was dissolved in 15 mL MDC containing 5 mL of trifluoroacetic acid. The solution was stirred at room temperature under nitrogen for 2 hr, taken to dryness and the residue triturated with hexane/ether. The resulting solid was collected by filtration to give 0.4 (82%) of 4-isopropyl-6-methoxy-2-saccharinylmethyl 2,6-dichloro-3-carboxymethoxybenzoate, mp 206°-208°.

EXAMPLE 4

By reaction of an appropriate 4-$R^4$-$R^5$-2-halomethylsaccharin of formula IV with an appropriate arylcarboxylic acid using the procedure described above in Example 1A, or by reaction of the appropriate saccharin of formula II with the appropriate chloromethyl benzoate using the procedure described in Example 11 below, the compounds of formula I listed in TABLE 2 below can be prepared.

TABLE 2

| Example | $R^4$ | $R^5$ | Ar |
|---|---|---|---|
| 4A | Br | H | 2,6-Cl₂4-NH₂C₆H₂ |
| 4B | Cl | H | 2,6-Cl₂-3-(CONH₂)C₆H₂ |
| 4C | CH₃O | H | 2,6-Cl₂C₆H₃ |
| 4D | CH(C₂H₅)₂ | H | 2,6-Cl₂H₆H₃ |
| 4E | CH₃O | 6-CH₃O | 2,6-Cl₂H₆H₃ |
| 4F | H | 7-Cl | 2,6-Cl₂H₆H₃ |
| 4G | CH₃ | 5-CH₃O | 3-(CH₃NHCH₂CH₂)C₆H₄ |
| 4H | COOCH₃ | H | 2,6-Cl₂H₆H₃ |
| 4I | C₂H₅O | H | 2,6-Cl₂H₆H₃ |
| 4J | (CH₃)₂CHO | H | 2,6-Cl₂H₆H₃ |
| 4L | H | 6-NO₂ | 2,6-Cl₂H₆H₃ |
| 4M | H | 5-(CH₃)₃CCH₂C(CH₃)₂ | 2,6-Cl₂H₆H₃ |
| 4N | H | 4,7-(CH₃O)₂ | 2,6-Cl₂H₆H₃ |
| 4-O | C₂H₅O | 7-CH₃(OCH₂CH)₂O | 2,6-Cl₂H₆H₃ |
| 4P | CH₃O | 7-CH₃(OCH₂CH)₂O | 2,6-Cl₂H₆H₃ |

TABLE 2-continued

| Example | R⁴ | R⁵ | Ar |
|---|---|---|---|
| 4Q | n-C₃H₇ | H | 2,6-Cl₂H₆H₃ |
| 4R | CH₃ | 7-CH₃ | 3-[(CH₃)₂NCH₂CH₂OOC]C₆H₄ |
| 4T | CF₃ | H | 3-[(CH₃)₂NCH₂CH₂NH]C₆H₄ |
| 4U | CCl₃ | H | 2,6-Cl₂H₆H₃ |
| 4V | H | 6-cyclohexyl | 2,6-Cl₂H₆H₃ |
| 4W | H | 6-CH₃SO₂NH | 2,6-Cl₂H₆H₃ |
| 4X | H | 6-CF₃SO₂NH | 2,6-Cl₂H₆H₃ |
| 4Y | H | 6-CCl₃SO₂NH | 2,6-Cl₂H₆H₃ |
| 4Z | H | 6-CN | 2,6-Cl₂H₆H₃ |
| 4AA | H | 6-NH₂SO₂ | 2,6-Cl₂H₆H₃ |
| 4AB | H | 6-CH₃SO₂NHSO₂ | 2,6-Cl₂H₆H₃ |
| 4AC | H | 6-CH₃SO₂ | 2,6-Cl₂H₆H₃ |
| 4AD | H | 6-CF₃SO₂ | 2,6-Cl₂H₆H₃ |
| 4AE | H | 6-HOOC | 2,6-Cl₂H₆H₃ |
| 4AF | H | 6-HOCH₂ | 2,6-Cl₂C₆H₃ |
| 4AG | H | 6-OHC | 2,6-Cl₂H₆H₃ |
| 4AH | H | 6-NH₂CH₂ | 2,6-Cl₂H₆H₃ |
| 4AI | H | 6-CF₃ | 3-(1-azet)C₆H₄ |
| 4AJ | H | 6-CCl₃ | 2,6-Cl₂H₆H₃ |
| 4AK | CH=CH₂ | H | 2,6-Cl₂H₆H₃ |
| 4AL | C≡CH | H | 2,6-Cl₂H₆H₃ |
| 4AM | NH₂ | H | 2,6-Cl₂H₆H₃ |
| 4AN | CH₃NH | H | 1-(1-imidazol)C₆H₄ |
| 4AO | (CH₃)₂N | H | 2,6-Cl₂H₆H₃ |
| 4AP | CH(CH₃)₂ | 6-CH₃S | 2,6-Cl₂H₆H₃ |
| 4AQ | CH(CH₃)₂ | 6-CH₃SO | 2,6-Cl₂H₆H₃ |
| 4AR | CH(CH₃)₂ | 6-CH₃SO₂ | 2,6-Cl₂H₆H₃ |
| 4AS | CH(CH₃)₂ | 6-F | 3-(1-pyr.)C₆H₄ |
| 4AT | CH(CH₃)₂ | 6-C₆H₅S | 2,6-Cl₂H₆H₃ |
| 4AU | CH(CH₃)₂ | 6-(4-CH₃C₆H₄S) | 2,6-Cl₂H₆H₃ |
| 4AV | CH(CH₃)₂ | 6-(4-CH₃OC₆H₄S) | 2,6-Cl₂H₆H₃ |
| 4AW | CH(CH₃)₂ | 6-(4-ClC₆H₄S) | 2,6-Cl₂H₆H₃ |
| 4AX | CH(CH₃)₂ | 6-(4-ClC₆H₄S) | 2,6-Cl₂H₆H₃ |
| 4AY | CH(CH₃)₂ | 6-(1-naphthyl-S) | 2,6-Cl₂H₆H₃ |
| 4AZ | CH(CH₃)₂ | 6-C₆H₅SO | 2,6-Cl₂H₆H₃ |
| 4BA | CH(CH₃)₂ | 6-C₆H₅SO₂ | 2,6-Cl₂H₆H₃ |
| 4BB | CH(CH₃)₂ | 6-(4-CH₃C₆H₄SO) | 2,6-Cl₂H₆H₃ |
| 4BC | CH(CH₃)₂ | 6-(4-CH₃C₆H₄SO₂) | 2,6-Cl₂H₆H₃ |
| 4BD | CH(CH₃)₂ | 6-(4-CH₃OC₆H₄SO) | 2,6-Cl₂H₆H₃ |
| 4BE | CH(CH₃)₂ | 6-(4-CH₃OC₆H₄SO₂) | 2,6-Cl₂H₆H₃ |
| 4BF | CH(CH₃)₂ | 6-(4-ClC₆H₄SO) | 2,6-Cl₂H₆H₃ |
| 4BG | CH(CH₃)₂ | 6-(4-ClC₆H₄SO₂) | 2,6-Cl₂H₆H₃ |
| 4BH | CH(CH₃)₂ | 6-(4-CH₃-1-naphthyl-SO) | 2,6-Cl₂H₆H₃ |
| 4BI | CH(CH₃)₂ | 6-(4-CH₃-1-naphthyl-SO₂) | 2,6-Cl₂H₆H₃ |
| 4BJ | CH(CH₃)₂ | 6-(1-naphthyl-SO) | 2,6-Cl₂H₆H₃ |
| 4BK | CH(CH₃)₂ | 6-(1-naphthyl-SO₂) | 2,6-Cl₂H₆H₃ |
| 4BL | CH(CH₃)₂ | 6-CH₃COO | 2,6-Cl₂H₆H₃ |
| 4BM | CH(CH₃)₂ | 6-C₆H₅COO | 2,6-Cl₂H₆H₃ |
| 4BN | CH(CH₃)₂ | 6-(1-naphthyl-COO) | 2,6-Cl₂H₆H₃ |
| 4BO | CH(CH₃)₂ | 6-(1-azetidinyl) | 2,6-Cl₂H₆H₃ |
| 4BP | CH(CH₃)₂ | 6-(1-pyrrolidinyl) | 2,6-Cl₂H₆H₃ |
| 4BQ | CH(CH₃)₂ | 6-(1-piperidinyl) | 2,6-Cl₂H₆H₃ |
| 4BR | CH(CH₃)₂ | 6-(4-morpholinyl) | 2,6-Cl₂H₆H₃ |
| 4BS | CH(CH₃)₂ | 6-(4-benzyl-1-piperazinyl) | 2,6-Cl₂H₆H₃ |
| 4BT | CH(CH₃)₂ | 6-(4-methyl-1-piperazinyl) | 2,6-Cl₂H₆H₃ |
| 4BU | CH(CH₃)₂ | 6-(1-1H-imidazolyl) | 2,6-Cl₂H₆H₃ |
| 4BV | CH(CH₃)₂ | 6-(NHCH₂COOC₄H₉-t) | 2,6-Cl₂H₆H₃ |
| 4BW | CH(CH₃)₂ | 6-NH₂ | 2,6-Cl₂H₆H₃ |
| 4BX | CH(CH₃)₂ | 6-(1-piperazinyl) | 2,6-Cl₂H₆H₃ |
| 4BY | CH(CH₃)₂ | 6-(NHCH₂COOH) | 2,6-Cl₂H₆H₃ |
| 4BZ | CH(CH₃)₂ | 6-(CH₃CONH) | 2,6-Cl₂H₆H₃ |
| 4CA | CONH₂ | H | 2,6-Cl₂C₆H₃ |

EXAMPLE 4CB

According to the procedure of Example 4, 2-chloromethyl-4-spirocyclopropyl-4,5,6,7-tetrahydrosaccharin of preparation 19BI is coupled with 2,6-dimethylbenzoic acid to provide 4-spirocyclopropyl-4,5,6,7-tetrahydro-2-saccharinylmethyl 2,6-dimethylbenzoate.

EXAMPLE 4CC

According to the procedure of Example 4, 2-chloromethyl-4-isopropyl-6-methoxy-4,5,6,7-tetrahydrosaccharin of preparation 19BJ is coupled with 2,6-dimethylbenzoic acid to provide 4-isopropyl-6-methoxy-4,5,6,7-tetrahydro-2-saccharinylmethyl 2,6-dimethylbenzoate.

EXAMPLE 5A

To a solution of 500 mg (1.1 mmol) of 6-hydroxy-4-isopropyl-2-saccharinylmethyl 2,6-dichlorobenzoate in 10-15 ml of THF were added 298 mg (1.14 mmol) of triphenylphosphine, 52 mg (1.13 mmol) of ethanol and 198 mg (1.14 mmol) of diethyl azodicarboxylate at RT. The mixture was stirred for 1½ hr and then chromatographed on silica gel with 10% ethyl acetate in hexane to yield 370 mg (70%) of 6-ethoxy-4-isopropyl-2-saccharinylmethyl 2,6-dichlorobenzoate as a white powder, mp 140°-141° C.

Following the procedure of Example 5A, the compounds of Table 3 were prepared from the 6-hydroxy compound of Example 1AW.

TABLE 3

| Example | R5 | mp | yield (%) |
|---|---|---|---|
| 5B | 6-iPrO | 114–115 | 73 |
| 5C | 6-OCH₂—[O—C(CH₃)(CH₃)—O] (isopropylidene dioxolane) | 123–125 | 70 |
| 5D | 6-(OCH₂CH₂)₂OCH₃ | 119–120 | 74 |
| 5E | 6-OCH₂COOCH₃ | foam | 64 |
| 5F | 6-OCH₂CH(OCH₃)CH₂OCH₃ | gum | 53 |
| 5G | 6-O-cyclobutyl | 150–151 | 44 |

The protected glycerol used in the synthesis of Example 5F was obtained as follows:

A solution of 10.0 g (0.055 mol) of DL-α-O-benzylglycerol in a little THF was added to a suspension of 15.38 g (0.137 mol) of potassium tert-butoxide in 300 mL of THF. The mixture was stirred for 1 hr at RT and 18.72 (0.132 mol) of iodomethane was added. A white solid immediately separated. The reaction was stirred for 10 hr at RT, cooled, carefully diluted with sodium chloride solution and extracted with ether. The organic layer was washed with water, 5% HCl, water and saturated NaCl and dried. The solvent was removed and the residue was purified by flash chromatography to give 1-benzyloxy-2,3-dimethoxypropane, 9.16 g (79%), as an oil.

A solution of 8.8 g (0.042 mol) of this material in 200 ml of MEOH was hydrogenated using 1.1 g of 10% Pd/C at 50 psi. The catalyst was removed by filtration and the solvent under reduced pressure-to give 4.4 g (87%) of 2,3-dimethoxy-1-propanol.

EXAMPLE 5I

6-Ethoxy-4-isopropyl-2-phenylthiomethylsaccharin was prepared from the 6-hydroxy analog (Preparation 19) by the procedure of Example 5A in 85% yield as a solid, mp 111.5°–112.5° C., which was converted to 2-chloromethyl-6-ethoxy-4-isopropylsaccharin in 91% yield, mp 127°–128° C., following the procedure of Preparation 18A.

EXAMPLE 5J

To a solution of 4-isopropyl-6-hydroxysaccharinylmethyl 2,6-dichlorobenzoate of Example 1C (0.44 g, 1.0 mmol) in MDC (20 mL) was added at 0° C. triethylamine (0.3 g, 3.0 mmol) and trifluoromethanesulfonic anhydride (0.37 g, 1.3 mmol). After being stirred at 0° C. for 10 min, the reaction mixture was diluted with MDC (50 mL) and washed with saturated NaHCO₃, brine and dried. Removal of the solvent in vacuo and purification of the residue by chromatography on silica gel (5% ethyl acetate in MDC) gave 0.53 g (88%) of 4-isopropyl-6-trifluoromethanesulfonyloxysaccharinylmethyl 2,6-dichlorobenzoate as a colorless foam.

The trifluoromethanesulfonate (0.28 g, 0.49 mmol) was mixed with 1-methyl-2-trimethylstannyl-pyrrole (0.19 g, 0.78 mmol), tetrakis (triphenylphosphine) palladium (O) (0.012 g, 0.01 mmol), lithium chloride (0.062 g, 1.5 mmol) and 2,6-di-tert-butyl-4-methyl-phenol (0.01 g, 0.05 mmol) in p-dioxane (10 mL) and refluxed under nitrogen for 30 min. The resulting dark reaction mixture was cooled to room temperature, diluted with ether (50 mL) and filtered through a pad of super cel. The filtrate was washed with water, brine and dried. Removal of the solvent in vacuo and purification of the residue by flash chromatography on silica gel (7:2:1, hexanes:MDC:ether) gave 0.22 g (92%) of 4-isopropyl-6-[2-[1-methyl]pyrolyl]saccharinylmethyl 2,6-dichlorobenzoate as a pale yellow solid, mp 125°–127° C.

EXAMPLE 5K

4-Isopropyl-6-trifluoromethanesulfonyloxysaccharinylmethyl 2,6-dichlorobenzoate, prepared as in Example 5J, (0.7 g, 1.2 mmol) in THF (10 mL) was cooled to −5° C. and was treated with 40% aqueous dimethylamine (0.6 mL, 5.3 mmol) and stirred at room temperature overnight. The resulting mixture was diluted with saturated NaHCO₃ solution (20 mL) and MDC (250 mL). The layers were separated and the organic phase washed with water, brine and dried. Removal of the solvent in vacuo and purification of the residue by chromatography on silica gel (6:3:1, hexanes:MDC:ether) gave 0.2 g (35%) of 4-isopropyl-6-dimethylaminosaccharinylmethyl 2,6-dichlorobenzoate. mp 177°–179°.

EXAMPLE 5L

A solution of 42 mg of 4-isopropyl-6-hydroxysaccharinylmethyl 2,6-dichlorobenzoate of Example 1C, di-(sec-butoxymethyl)methylamine and toluene was heated at 80° for 1 hour, cooled and volatiles removed. Slurrying in hexane yielded 30 mg of 2-(2,6-dichlorobenzoyloxymethyl)-4-isopropyl-8-methyl-2,3,7-tetrahydro-9H-[1,3]oxazino[6,5-g]benzisothiazol-3-one-1,1-dioxide.

EXAMPLE 6

A solution of 600 mg (1.1 mmol) of the isopropylidene of Example 5C, Table 3, and 176 mg (0.9 mmol) of p-toluenesulfonic acid monohydrate in methanol-chloroform was stirred overnight. The mixture was chromatographed on silica gel to give 290 mg (53%) of 6-(2,3-dihydroxypropoxy)-4-isonpropylsaccharinylmethyl 2,6-dichlorobenzoate as a foam.

EXAMPLE 7A

To a solution of 1.0 g (2.3 mmol) of 6-hydroxy-4-isopropyl-2-saccharinylmethyl 2,6-dichlorobenzoate in 40 ml of acetone at RT were added 0.62 g (4.5 mmol) of anhydrous K₂CO₃ and 0.66 g (9/3.4 mmol) of t-butyl bromoacetate. The mixture was stirred for 4–5 hr and filtered. The filtrate was concentrated under reduced pressure and the residue was purified by flash chromatography to give 1.13 g (90%) of 6-(2-t-butoxy-2-oxoethoxy)-4-isopropyl-2-saccharinylmethyl 2,6-dichlobenzoate as a glass.

EXAMPLE 7B

In a similar manner 6-(2-benzyloxy-2-oxoethoxy)-4-isopropyl-2-saccharinylmethyl 2,6-dichlorobenzoate was obtained as a glass in 61% yield from the 6-hydroxy compound and benzyl bromoacetate.

EXAMPLE 8

To freshly distilled cyclopentadiene (25 mL) at 0° C. was added 4-bromo-2-(tert-butyl)isothiaziol-3(2H)-one 1,1-dioxide (Helv. Chim. Acta., 72, 1416, 1989) (7.9 g, 0.03 mol). After stirring at 0' C. under nitrogen for 16 hr, the reaction mixture was concentrated in vacuo. The residue was purified by filtering through silica gel, eluting with hexanes (500 mL) followed by 20% ethyl acetate in hexanes (500 mL). The latter eluents were concentrated in vacuo to give 9.8 g (100% of the norbornene adduct, 3a-bromo-2-t-butyl-3a,4,7,7a-tetrahydro-4,7-methano-1,2-benzisothiazol-3(2H)-one 1,1-dioxide, as a white solid.

The adduct (0.4 g, 1.2 mmol) in 25 mL of ethyl acetate containing 5% Pd on $CaCO_3$ (0.2 g) was stirred under one atmosphere of hydrogen for 4 hr, and the reaction mixture was filtered through a pad of silica gel, eluting with ethyl acetate (100 mL). The eluents were concentrated in vacuo and the residue crystallized from hexanes to give 0.4% (100%) of the bromo norbornane as a white crystalline solid.

To a solution of the bromo norbornane (3.7 g, 0.011 mol) in toluene (25 mL) at 0° C. was added diazabicyclononene (1.37 g, 0.011 mol) in toluene (10 mL), After stirring at 0° C. for 20 min, silica gel (25 g) was added to the reaction mixture. The resulting slurry was loaded on top of a 15 cm pad of silica gel and eluted with 20% ethyl acetate in hexanes (800 mL). The eluents were concentrated in vacuo to give 2.8 (100%) of the dehydrobrominated compound as a white solid.

The 2-t-butyl-4,5,6,7-tetrahydro-4,7-methano-1,2-benzisothiazol-3(2H)one 1,1-dioxide (2.8 g, 0.011 mol) in trifluoroacetic acid (30 mL) was heated at reflux for 48 hr and let stand at room temperature for 4 days. The resulting mixture was concentrated in vacuo, treated with methanol (20 mL) and evaporated to dryness. The residue was taken up in ether (100 mL) and washed with saturated $NaHCO_3$ (1×50 mL). The layers were separated, the aqueous phase acidified to pH 1 with 2N HCl and extracted with MDC (2×100 mL). The combined organic extracts were dried and concentrated in vacuo to give 0.9 g (42%) of the bicyclo (2.2.1) saccharin derivative as a white solid.

A mixture of the bicyclo (2,2,1) saccharin derivative (0.9 g, 5 mmol), chloromethyl phenylsulfide (0.07 g, 7 mmol) and tetrabutylammonium bromide (0.36 g, 0.16 mmol) in toluene (50 mL) was refluxed under nitrogen for 16 hr, cooled to room temperature and evaporated to dryness under vacuum. The residue was purified by flash chromatography on silica gel (100 g) using 100% MDC as the eluent to give 1.05 (72%) of the sulfide as a viscous oil.

The sulfide (1.05 g, 3 mmol) in dichloromethane (100 mL) was treated with sulfuryl chloride (0.66 g, 5 mmol) and stirred for 2 hr. The resulting yellow solution was diluted with MDC (100 mL), washed with saturated $NaHCO_3$ solution, dried and concentrated in vacuo. The residue was purified by flash chromatography on silica gel (33% MDC in hexanes) to give 0.66 g (81%) of 2-chloromethyl-4,5,6,7-tetrahydro-4,7-methano-1,2-benzisothiazol-3(2H)-one 1,1-dioxide.

The 2-chloromethyl compound (0.66 g, 2.7 mmol) was treated with 2,6-dichlorobenzoic acid (0.56 g, 2.9 mmol), anhydrous potassium carbonate (0.55 g, 4.0 mmol) and tetrabutylammonium bromide (0.2 g, 0.6 mmol) in DMF (2.5 mL) at 70° C. for 1 hr. The resulting mixture was concentrated in vacuo, diluted with ethyl acetate (100 mL) and filtered. The filtrate was washed with water, saturated $NaHCO_3$, water and brine. The organic phase was concentrated in vacuo, and the residue was purified by flash chromatography on silica gel (3:6:1, MDC:hexanes:ether) to give 0.5g (47%) of 2-(2,6-dichlorobenzoyloxymethyl)4,5,6,7-tetrahydro-4,7-methano-1,2-benzisothiazol-3(2H)-one 1,1-dioxide as a colorless foam.

EXAMPLES 8B AND 8C

By a process analagous to that of Example 8A, it is contemplated that cyclohexadiene and 1,1-dimethylcyclopentadiene may be converted respectively to 2-(2,6-dichlorobenzcyloxymethyl4,5,6,7-tetrahydro-4,7-ethano-1,2-benzisothiazol-3(2H)-one 1,1-dioxide and 2-(2,6-dichlorobenzoyloxymethyl)-8,8-dimethyl-4,5,6,7-tetrahydro-4,7-methano-1,2-benzoisothiazol-3(2H)-one 1,1-dioxide

EXAMPLE 9A–9D

General procedure for the preparation of methyl-2-alkycyclohexan-6-one caboxylate: To a suspension of anhydrous CuI (10 mmol) in anhydrous THF (100 mL) was added $Me_2S$ (100 mmol) and the resulting solution was cooled to −78° C. The Grignard reagent (20 mmol) was added over a period of 15 min. After being stirred at −78° C. for an hour, a solution of cyclohexenone (10 mmol) in THF was added and stirring continued for another 15 min. To the resulting mixture was added HMPA (5 mL) and, after 15 min, methyl cyanoformate (30 mmol) in THF (20 mL) and the reaction warmed to room temperature and stirred overnight. The reaction mixture was quenched with 2N HCl (50 mL). The layers were separated and the aqueous phase extracted with $Et_2O$ (1×100 mL). The combined organic extracts were washed with saturated $NH_4Cl$ solution (3×50 mL), water (2×50 mL), brine (1×50 mL) and dried ($Na_2SO_4$). Removal of the solvent in vacuo and purification by either Kugelrohr distillation or flash chromatography afforded the desired methyl 2-alkylcyclohexan-6-one caboxylate (Table E).

TABLE E

| Intermediate | Alkyl | Yield | b.p. |
|---|---|---|---|
| B | Me | 82 | — |
| C | Et | 70 | 100–110° C. (0.2 mm) |
| D | iPr | 74 | 106–109° C. (0.5 mm) |

General procedure for the preparation of methyl 2-benzylthio-6-alkylcyclohex-2-ene carboxylate and 2-benzylthio-6-alkylcyclohex-1-ene carboxylate: A mixture of methyl-2-alkylcyclohexan-6-one carboxylate (1 eq), benzylmercaptan (1.1 eq) and the acidic clay montmorillonite, KSF (1.5 times the weight of methyl-2-alkylcyclohexan-6-one carboxylate) in anhydrous toluene (50–100 mL) was refluxed under nitrogen with azeotropic removal of water for 12–14 hr and cooled to room temperature. The solids were filtered off and washed with ether. The combined filtrate was washed with 10% $Na_2CO_3$, water, brine and dried. Removal of the solvent in vacuo and purification of the residue by flash chromatography on silica gel (10% ether in hexanes) gave a mixture of methyl 2-benzylthio-6-alkylcyclohex-2-ene carboxylate and 2-benzylthio-6-alkylcyclohex-1-ene carboxylate (Table F) which was used in the next step as a mixture.

TABLE F

| Intermediate | Alkyl | 2Combined Yield of Mixture |
|---|---|---|
| A | H | 40 |
| B | Me | 44 |
| C | Et | 50 |
| D | iPr | 52 |

General procedure for the preparation of 4-alkyl-tetrahydrosaccharins: A solution of methyl 2-benzylthio-6-alkylcyclohex-2-ene-carboxylate and 2-benzylthio-6-alkylcyclohex-1-ene carboxylate (1-10 mmol of the mixture) in 10 mL of MDC was diluted with 20-50 mL of glacial acetic acid and 1-5 mL of water, the mixture cooled to −10° C., and chlorine gas was bubbled through the mixture until the exothermic reaction subsided. The mixture was then stirred for 10 minutes and taken to dryness to give a mixture of methyl 2-chlorosulfonyl-6-alkylcyclohex-2-ene carboxylate and 2-chlorosulfonyl-6-alkylcyclohex-1-ene carboxylate, which was dissolved in 10 mL of THF and added to 25 mL of a solution of concentrated ammonium hydroxide while cooling in an ice/acetone bath. After stirring for 2 hr, the reaction mixture was concentrated in vacuo, the residue taken up in water, acidified to pH 1 with 2N HCl, and extracted with MDC. The organic phase was dried and concentrated in vacuo to give a mixture of methyl 2-aminosulfonyl-6-alkylcyclohex-2-ene carboxylate and 2-aminosulfonyl-6-alkylcyclohex-1-ene carboxylate. The mixture was dissolved in methanol and added to a freshly prepared solution of sodium methoxide (10-50 mmol) and stirred at ambient temperature for 12 hr. The reaction mixture was concentrated in vacuo, diluted with water and extracted with ether. The organic phase was discarded, and the aqueous phase was acidified to pH 1 with concentrated HCl and extracted with MDC. The organic extracts, on washing with brine, drying and evaporation to dryness, afforded 4-alkyl-4,5,6,7-tetrahydrobenzisothiazol-3-one 1,1-dioxide or 4-alkyl-tetrahydro saccharins (Table G).

TABLE G

| Intermediates | Alkyl | Yield |
|---|---|---|
| A | H | 50 |
| B | Me | 85 |
| C | Et | 80 |
| D | iPr | 74 |

A mixture of 4-alkyl-4,5,6,7-tetrahydrobenzisothiazol-3-one 1,1-dioxide (4-alkyltetrahydro saccharin) (1.0 eq), chloromethyl phenyl sulfide (1.5 eq) and tetrabutylammonium bromide (0.2 eq) in toluene (25 mL/g of saccharin) was refluxed under nitrogen for 16-24 hr and then cooled to room temperature. The resulting mixture was evaporated to dryness and the residue chromatographed on silica gel eluting with hexanes/MDC (1:1 to 1:3) to give the corresponding 2-phenylthiomethyl-4-alkyl-4,5,6,7-tetrahydrobenzisothiazole -3-one 1,1-dioxide or 2-phenylthiomethyl-4-alkyl-tetrahydro saccharin (Table H).

TABLE H

| Example | Alkyl | Yield |
|---|---|---|
| A | H | 40 |
| B | Me | 55 |
| C | Et | 40 |
| D | iPr | 53 |

A solution of 2-phenylthiomethyl-4-alkyl-tetrahydro saccharin (1.0 eq) was treated with sulfuryl chloride (1.5 eq) and stirred for 2 hr. The resulting yellow solution was taken to dryness to give 2-chloromethyl-4-alkyl-tetrahydro saccharin, which was treated with 2,6-dichlorobenzoic acid (1.1 eq), anhydrous potassium carbonate (1.5 eq) and tetrabutylammonium bromide (0.2 eq) in DMF (25 mL) at 70° C. for 1 hr. The resulting mixture was concentrated in vacuo, diluted with ethyl acetate (100 mL) and filtered. The filtrate was washed with water, saturated NaHCO$_3$, water and brine. The organic phase was concentrated in vacuo, and the residue purified by flash chromatography on silica gel (2:1 MDC/hexanes) to give 4-alkyl-4,5,6,7-tetrahydro-2-saccharinylmethyl 2,6-dichlorobenzoate (Table J).

TABLE J

| Example | Alkyl | Yield | mp (°C.) |
|---|---|---|---|
| 9A | H | 63 | 93-95 |
| 9B | Me | 54 | 127-129 |
| 9C | Et | 50 | 86-89 |
| 9D | iPr | 48 | 108-110 |

EXAMPLE 9E

Following a procedure similar to that described for Example 1AA, 2-chloromethyl-4-isopropyl-4,5,6,7-tetrahydrobenzisothiazol-3-one 1,1-dioxide was treated with 2,6-dichloro-3-[[2-(N,N-dimethylamino)ethyl]-N-methylaminosulfonyl]benzoic acid (Preparation 20F) to give 4-isopropyl-4,5,6,7-tetrahydro-2-saccharinylmethyl 2,6-dichloro-3-[[2-(N,N-dimethylamino)ethyl]-N-methylaminosulfonyl]benzoate hydrochloride, mp 121 (dec).

EXAMPLE 10

Methyl 2,2-dimethylcyclohexan-6-one carboxylate: To a suspension of anhydrous CuI (70.0 g, 0.37 mol) in anhydrous ether (500 mL) at 0° C. was added halide-free methyl lithium (520 mL of 1.4 M solution in ether, 0.73 mol). After being stirred at 0' C. for 15 minutes, a solution of 3-methyl-2-cyclohexenone (20.0 g, 0.18 mol) in ether (50 mL) was added and stirring continued for another 1 hr. To the resulting mixture was aded THF (50 mL) and HMPA (25 mL) and after 15 min methyl cyanoformate (45.0 g, 0.53 mol) in THF (20 mL) and the reaction warmed to room temperature and stirred for 3 hr. The reaction mixture was quenched with 2N HCl (50 mL). The layers were separated and the aqueous phase extracted with Et$_2$O (1×500 mL). The combined organic extracts were washed with saturated NH$_4$Cl solution (3×50 mL), water (2×50 mL), brine (1×50 mL) and dried (Na$_2$SO$_4$). Removal of the solvent in vacuo and purification by Kugelrohr distillation afforded 34.0 g (99%) of methyl 2,2-dimethyl cyclohexane-6-one carboxylate, bp 80°-84° C./0.6 mm.

The cyclohexanone was converted to 4,4-dimethyl-4,5,6,7-tetrahydro-2-saccharinylmethyl 2,6-dichlorobenzoate, mp 121°-123° C., following the procedure described above for Example 9D.

EXAMPLE 11

Following the procedure of preparation 18A, 5 g of 2-bromo-N,N-dimethylaniline was converted to 3.5 g of N,N-diethyl-2-dimethylaminobenzamide. The amide was reacted by the method of preparation 18B to provide 65 mg of 4-dimethylaminosaccharin, mp 228°-229° from ether-hexane. A mixture of 11.1 g of 2,6-dichlorobenzoyl chloride, 1.9 g of paraformaldehyde and 0.1 g of fused zinc chloride were heated at 100° for 2 hr and then vacuum distilled to yield 3.5 g of chloromethyl 2,6-dichlorobenzoate collected above 145 ° at aspirator pressure which solidified on cooling, mp 70°-72°. To a solution of 4-dimethylaminosaccharin and 0.1 mL of diisopropylethylamine in 1 mL of dry acetonitrile was added 100 mg of chloromethyl 2,6-dichlorobenzoate.

The mixture was stirred at room temperature for 48 hrs and then at 50° for 24 hours, when tlc (MDC) showed complete reaction. The mixture was poured into EtOAc and extracted with saturated NaHCO$_3$ solution. The organic layer was dried and the solvent removed at reduced pressure. Chromatography in MDC yielded 15 mg of 4-dimethylamino-2-saccharinylmethyl 2,6-dichlorobenzoate.

BIOLOGICAL TEST RESULTS

Measurement of the inhibition constant, $K_i$, of a HLE-inhibitor complex has been described for "truly reversible inhibition constants" usually concerning competitive inhibitors. [Cha, Biochem. Pharmacol., 24, 2177-2185 (1975)]. The compounds of the present invention, however, do not form truly reversible inhibitor complexes but are consumed by the enzyme to some extent. Thus, instead of measuring a $K_i$, a $K_i^*$ is calculated which is defined as the ratio of the $k_{off}/k_{on}$, the rate of reactivation of the enzyme to the rate of inactivation of the enzyme. The values of $k_{off}$ and $k_{on}$ are measured and $K_i^*$ is then calculated.

The rate of inactivation, $k_{on}$, of enzymatic activity was determined for the compounds tested by measuring the enzyme activity of an aliquot of the respective enzyme as a function of time after addition of the test compound. By plotting the log of the enzyme activity against time, an observed rate of inactivation, $k_{obs}$, is obtained which can be represented as $k_{obs} = \ln 2/t_{\frac{1}{2}}$ where $t_{\frac{1}{2}}$ is the time required for the enzyme activity to drop by 50%. The rate of inactivation is then equal to $$k_{on} = \frac{k_{obs}}{[I]}$$

where [I] is the concentration of the inhibiting compound.

The reactivation constant, $k_{off}$, is similarly determined, and the inhibition constant, $K_i^*$, is then calculated as $$K_i^* = k_{off}/k_{on}$$

The values obtained for $k_{on}$ and $K_i^*$ for specific substituted saccharin derivatives are shown in TABLE 4, the compounds being identified by the Example numbers above where their preparations are described.

TABLE 4

| Example | $k_{on} \times 10^{-3}$ $M^{-1} sec^{-1}$ | $K^*_i$ (nM) |
|---|---|---|
| 1A | 375 | 0.08 |
| 1B | 522 | 0.023 |
| 1C | 28.9 | 0.40 |
| 1D | 6.3 | 8 |
| 1E | 3.1 | 18 |
| 1F | 14 | 3 |
| 1G | 3.7 | 18 |
| 1H | 9.3 | 8.5 |
| 1I | 46.0 | 0.48 |
| 1J | 670 | 0.03 |
| 1K | 250 | 0.09 |
| 1L | 77 | 0.30 |
| 1M | 92 | 0.25 |
| 1N | 3.4 | 31 |
| 1-O | 38 | 2 |
| 1P | 700 | 0.17 |
| 1Q | 900 | 0.03 |
| 1R | 460 | 1.0 |
| 1S | 30 | 2.0 |
| 1T | 15.3 | 4.0 |
| 1U | 2000 | 0.01 |
| 1V | 3000 | 0.007 |
| 1W | 2000 | 0.01 |
| 1X | 46 | 0.5 |
| 1Y | 192 | 0.12 |
| 1Z | 380 | 0.06 |
| 1AA | 2300 | 0.01 |
| 1AB | 1438 | 0.016 |
| 1AC | 920 | 0.025 |
| 1AD | 2875 | 0.008 |
| 1AE | 2556 | 0.009 |
| 1AF | 2300 | 0.01 |
| 1AG | 2300 | 0.01 |
| 1AH | 940 | 0.06 |
| 1AI | 24.5 | 2.7 |
| 1AJ | 10 | 8 |
| 1AK | 16 | 4 |
| 1AM | 45 | 2.1 |
| 1AN | 1.5 | 37.3 |
| 1AO | 23 | 1.0 |
| 1AP | 1100 | 0.011 |
| 1AQ | 923 | 0.013 |
| 1AR | 857 | 0.014 |
| 1AS | 769 | 0.013 |
| 1AT | 714 | 0.014 |
| 1AU | 333 | 0.030 |
| 1AV | 435 | 0.023 |
| 1AX | — | 0.033 |
| 1AY | 22.3 | 0.900 |
| 1AZ | 21.5 | 1.100 |
| 1BA | — | 0.078 |
| 1BB | 100 | 0.350 |
| 1BC | 1000 | 0.030 |
| 1BD | — | 0.070 |
| 1BE | 156 | 0.064 |
| 1BF | 5.4 | 2.000 |
| 1BG | 354 | 0.043 |
| 1BH | 15 | 0.600 |
| 1BI | 307 | 0.029 |
| 1BJ | 474 | 0.029 |
| 1BK | 129 | 0.088 |
| 1BL | 233 | 0.043 |
| 1BM | 125 | 0.080 |
| 1BN | 400 | 0.025 |
| 1BO | 200 | 0.050 |
| 1BP | 28.6 | 0.350 |
| 1BQ | 147 | 0.068 |
| 1BR | 175 | 0.057 |
| 1BS | 277 | 0.036 |
| 1BT | — | — |
| 1BU | — | — |
| 1BW | 51.3 | 0.200 |
| 1BX | 6.2 | 26.000 |
| 1BY | 920 | 0.025 |
| 1BZ | 33 | 0.300 |
| 2A | 575 | 0.04 |
| 2B | 1150 | 0.02 |
| 2C | — | — |
| 2D | 1500 | 0.008 |
| 3 | 2300 | 0.01 |
| 3B | 1091 | 0.011 |
| 5A | 200.00 | 0.050 |
| 5B | 281 | 0.057 |
| 5C | 583 | 0.030 |
| 5D | 333 | 0.030 |
| 5E | 880.5 | 0.017 |
| 5F | — | 0.027 |
| 5G | — | 0.054 |
| 5J | — | 0.200 |
| 5K | 12.3 | 2.200 |
| 5L | 0.70 | 30.000 |
| 6 | 583 | 0.016 |
| 7A | 320 | 0.080 |
| 7B | 331 | 0.056 |
| 8 | — | 0.600 |
| 9A | 3.3 | 18.000 |
| 9B | 36 | 1.000 |
| 9C | 83 | 0.700 |
| 9D | 10 | 1.000 |
| 9E | 13.3 | 2.000 |
| 10 | 18.5 | 1.000 |
| 11 | 35 | 0.200 |

We claim:
1. 2-(2,6-Dichlorobenzoyloxymethyl)-4,5,6,7-tetrahydro-4,7-methano-1,2-benzisothiazol-3(2H)-one 1,1-dioxide.

* * * * *